(12) United States Patent
Ritter et al.

(10) Patent No.: US 11,179,710 B2
(45) Date of Patent: Nov. 23, 2021

(54) DIRECT PALLADIUM-CATALYZED AROMATIC FLUORINATION

(71) Applicants: President and Fellows of Harvard College, Cambridge, MA (US); Studiengesellschaft Kohle mbH, Mülheim an der Ruhr (DE)

(72) Inventors: Tobias Ritter, Mülheim (DE); Jeffrey Garber, Muelheim an der Ruhr (DE); Kumiko Yamamoto, Tokyo (JP)

(73) Assignees: President and Fellows of Harvard College, Cambridge, MA (US); Studiengesellschaft Kohle mbH, Mülheim an der Ruhr (DE)

(*) Notice: Subject to any disclaimer, the term of this patent is extended or adjusted under 35 U.S.C. 154(b) by 73 days.

(21) Appl. No.: 16/083,160

(22) PCT Filed: Mar. 9, 2017

(86) PCT No.: PCT/US2017/021563
§ 371 (c)(1),
(2) Date: Sep. 7, 2018

(87) PCT Pub. No.: WO2017/156265
PCT Pub. Date: Sep. 14, 2017

(65) Prior Publication Data
US 2019/0099748 A1    Apr. 4, 2019

Related U.S. Application Data

(60) Provisional application No. 62/346,326, filed on Jun. 6, 2016, provisional application No. 62/305,711, filed on Mar. 9, 2016.

(51) Int. Cl.
*C07D 471/04* (2006.01)
*B01J 23/44* (2006.01)
(Continued)

(52) U.S. Cl.
CPC .............. *B01J 31/30* (2013.01); *B01J 23/44* (2013.01); *B01J 31/183* (2013.01); *C07C 17/12* (2013.01);
(Continued)

(58) Field of Classification Search
None
See application file for complete search history.

(56) References Cited

PUBLICATIONS

Chen et al. The Journal of Physical Chemistry, 118, 20791-20798 (Year: 2014).*
(Continued)

*Primary Examiner* — Yun Qian
(74) *Attorney, Agent, or Firm* — Wolf, Greenfield & Sacks, P.C.

(57) ABSTRACT

Provided herein are palladium complexes comprising a ligand of Formula (A') and a ligand of Formula (B), wherein $R^1$-$R^{18}$ are as defined herein. The palladium complexes are useful in methods of fluorinating aryl and heteroaryl substrates. Further provided are compositions and kits comprising the palladium complexes.

(A')

(Continued)

-continued (B)

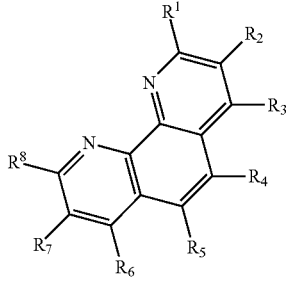

17 Claims, 12 Drawing Sheets

(51) Int. Cl.
B01J 31/30 (2006.01)
B01J 31/18 (2006.01)
C07C 17/12 (2006.01)
C07C 23/10 (2006.01)

(52) U.S. Cl.
CPC ............ *C07C 23/10* (2013.01); *C07D 471/04* (2013.01); *B01J 2231/4277* (2013.01); *B01J 2531/025* (2013.01); *B01J 2531/824* (2013.01)

(56) References Cited

PUBLICATIONS

Fujihara et al. (Dalton Trans., 3221-3226). (Year: 2003).*
International Search Report and Written Opinion, in connection with Application No. PCT/US2017/021563, dated Jun. 7, 2017.
International Preliminary Report on Patentability, in connection with Application No. PCT/US2017/021563, dated Sep. 20, 2018.
Bernhardt et al., Preparation of solid salt-stabilized functionalized organozinc compounds and their application to cross-coupling and carbonyl addition reactions. Angew Chem Int Ed Engl. Sep. 19, 2011;50(39):9205-9. doi: 10.1002/anie.201104291. Epub Aug. 24, 2011.
Burk et al., Preparation and use of C2-symmetric bis(phospholanes): production of alpha.-amino acid derivatives via highly enantioselective hydrogenation reactions. J. Am. Chem. Soc. 1993;115(22):10125-38. doi: 10.1021/ja00075a031.
Campbell et al., Modern carbon-fluorine bond forming reactions for aryl fluoride synthesis. Chem Rev. Jan. 28, 2015;115(2):612-33. doi: 10.1021/cr500366b. Epub Dec. 4, 2014.
Chambers, Fluorine in organic chemistry. Blackwell Publishing Ltd. Oxford, England. 2004. 420 pages.
Champagne et al., Monofluorination of Organic Compounds: 10 Years of Innovation. Chem Rev. Sep. 9, 2015;115(17):9073-174. doi: 10.1021/cr500706a. Epub Apr. 9, 2015.
Dmowski et al.,3-Chloro-4-fluorothiophene-1,1-dioxide. A new synthetically useful fluorodiene. J. Fluor. Chem. 1998;88(2):143-51. doi.org/10.1016/S0022-1139(98)00109-2.
Dubbaka et al., Silver-mediated fluorination of potassium aryltrifluoroborates with Selectfluor®. Tetrahedron. 2014;70(51): 9676-9681. doi.org/10.1016/j.tet.2014.10.055.
Fier et al., Selective C—H fluorination of pyridines and diazines inspired by a classic amination reaction. Science. Nov. 2, 20132;342(6161):956-60. doi: 10.1126/science.1243759.
Garber et al., Direct Palladium-Catalyzed Aryl C—H Fluorination. Author Manuscript. Mar. 9, 2016. 2 pages.
Hull et al., Palladium-catalyzed fluorination of carbon-hydrogen bonds. J Am Chem Soc. Jun. 7, 2006;128(22):7134-5.

Khusnutdinova et al., The conformational flexibility of the tetradentate ligand (tBu)N4 is essential for the stabilization of ((tBu)N4)Pd(III) complexes. Inorg Chem. Dec. 15, 2014;53(24):13112-29. doi: 10.1021/ic5023054. Epub Nov. 26, 2014.
Khusnutdinova et al., The aerobic oxidation of a Pd(II) dimethyl complex leads to selective ethane elimination from a Pd(III) intermediate. J Am Chem Soc. Feb. 1, 2012;134(4):2414-22. doi: 10.1021/ja210841f. Epub Jan. 20, 2012.
Lanci et al., Oxidatively induced reductive elimination from ((t)Bu2bpy)Pd(Me)2: palladium(IV) intermediates in a one-electron oxidation reaction. J Am Chem Soc. Nov. 4, 2009;131(43):15618-20. doi: 10.1021/ja905816q.
Liu et al., A fast and oxygen-promoted protocol for the ligand-free Suzuki reaction of 2-halogenated pyridines in aqueous media. Chem Commun (Camb). Nov. 7, 2009;(41):6267-9. doi: 10.1039/b912364d. Epub Sep. 3, 2009.
Mazzotti et al., Palladium(III)-catalyzed fluorination of arylboronic acid derivatives. J Am Chem Soc. Sep. 25, 2013;135(38):14012-5. doi: 10.1021/ja405919z. Epub Sep. 16, 2013. Author Manuscript.
Minami et al., Organoaluminum-mediated direct cross-coupling reactions. Angew Chem Int Ed Engl. Apr. 7, 2015;54(15):4665-8. doi: 10.1002/anie.201412249. Epub Feb. 20, 2015.
Mirica et al., Structure and electronic properties of Pd(III) complexes. Coord. Chem. Rev. 2012;257(2):299-314. doi.org/10.1016/j.ccr.2012.04.030.
Muller et al., The Catalytic Asymmetric Fischer Indolization. J. Am. Chem. Soc., 2011;133(46):18534-18537. DOI: 10.1021/ja2092163. Epub Nov. 1, 2011.
Powell et al., Stille cross-couplings of unactivated secondary alkyl halides using monoorganotin reagents. J Am Chem Soc. Jan. 19, 2005; 127(2):510-1.
Powers et al., Palladium(III) in Synthesis and Catalysis. Top Organomet Chem. Jan. 1, 2011;503:129-156.
Pryde et al., Novel selective inhibitors of neutral endopeptidase for the treatment of female sexual arousal disorder. Bioorg Med Chem. Jan. 1, 2007;15(1): 142-59. Epub Oct. 6, 2006.
Qiu et al., Palladium-catalyzed intermolecular aminofluorination of styrenes. J Am Chem Soc. Mar. 10, 2010;132(9):2856-7. doi: 10.1021/ja909716k.
Sandford, Elemental flourine in organic chemistry. J. Flourine Chemistry. 2007. 128(2): 90-104. doi.org/10.1016/j.jfluchem.2006.10.019.
Seo et al., Protodecarboxylation of benzoic acids under radical conditions. Chem Commun (Camb). Aug. 25, 2012;48(66):8270-2. doi:10.1039/c2cc33306f. Epub Jun. 15, 2012.
Tang et al., Structural and reactivity comparison of analogous organometallic Pd(III) and Pd(IV) complexes. Dalton Trans. Dec. 14, 2012;41(46):14046-50. doi: 10.1039/c2dt32127k. Epub Oct. 18, 2012.
Taylor et al., Recent advances in electrophilic fluorination. Tetrahedron. 1999. 55(43):12431-12477. doi.org/10.1016/S0040-4020(99)00748-6.
Urlam et al., Development of new N-Arylbenzamides as STAT3 Dimerization Inhibitors. Medchemcomm. Jun. 2013;4(6):932-941. Author Manuscript.
Wang et al., Versatile Pd(OTf)2×2 H2O-catalyzed orthofluorination using NMP as a promoter. J Am Chem Soc. Jun. 10, 2009;131(22):7520-1. doi: 10.1021/ja901352k.
Wu et al. Aerobic C—N bond activation: a simple strategy to construct pyridines and quinolines. The article was first published on Dec. 18, 2014. Chem. Commun., 2015;51:2286-2289. doi.org/10.1039/C4CC08074B.
Yamato et al., Metacyclophanes and related compounds. Part 16. Preparation of 8-fluoro-t-butyl[2.2]metacyclophanes and their treatment with aluminium chloride-nitromethane in benzene. J. Chem. Soc., Perkin Trans. 1, 1987;0:1-7. doi: 10.1039/P19870000001.
Yu et al., Palladium-catalyzed coupling of polyfluorinated arenes with heteroarenes via C—F/C—H activation. Org Lett. Feb. 15, 2013;15(4):940-3. doi: 10.1021/o1303567t. Epub Feb. 7, 2013.
Yuan et al., Highly selective Pd-catalyzed intermolecular fluorosulfonylation of styrenes. J Am Chem Soc. Feb. 25, 2015;137(7):2468-71. doi: 10.1021/ja5131676. Epub Feb. 11, 2015.

(56) References Cited

PUBLICATIONS

Zhou et al., Palladium-catalyzed desulfitative arylation by C—O bond cleavage of aryl triflates with sodium arylsulfinates. J Org Chem. Nov. 16, 2012;77(22): 10468-72. doi: 10.1021/jo302005s. Epub Nov. 7, 2012.

Yamamoto et al., Palladium-Catalyzed C($sp^2$)-H Fluorination. Abstract Only. Presented at the 96$^{th}$ Chemical Society of Japan Annual Meeting on Mar. 25, 2016. Epub Mar. 10, 2016. 1 page.

Yamamoto et al., Palladium-Catalyzed C($sp^2$)-H Fluorination. Presentation Slides. Presented at the 96$^{th}$ Chemical Society of Japan Annual Meeting on Mar. 25, 2016. 22 pages.

Yamamoto et al., Palladium-catalysed electrophilic aromatic C—H fluorination. Nature. Feb. 22, 2018;554:511-14. Doi: 10.1038/nature25749.

* cited by examiner

**EPR spectrum of *in situ* generated Pd(III) complex 5**

Figure 4A. DFT energy profile for Catalyst 1 with NFSI.
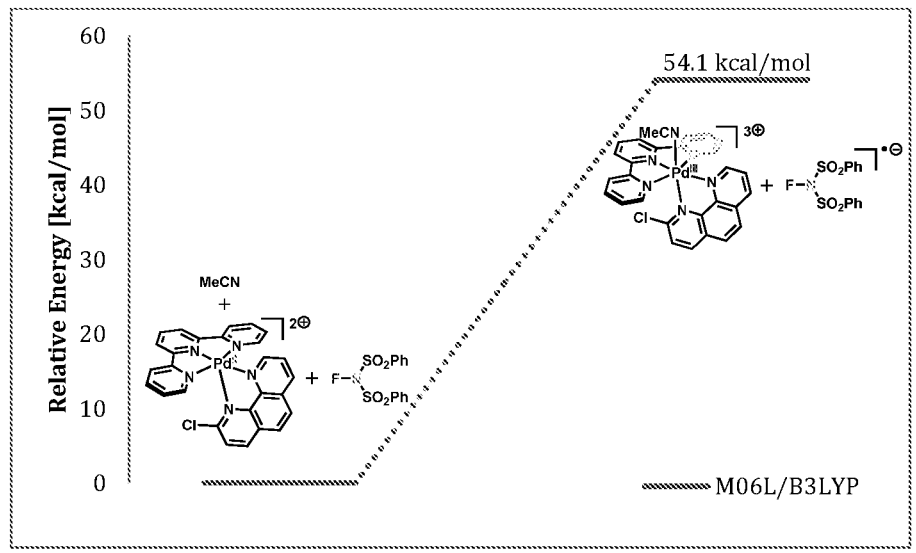
Sum substrates (Hartree): −3748.995466
Sum products (Hartree): −3748.909260
Figure 4B. Energy Profile for SET between Catalyst 1 and F-TEDA
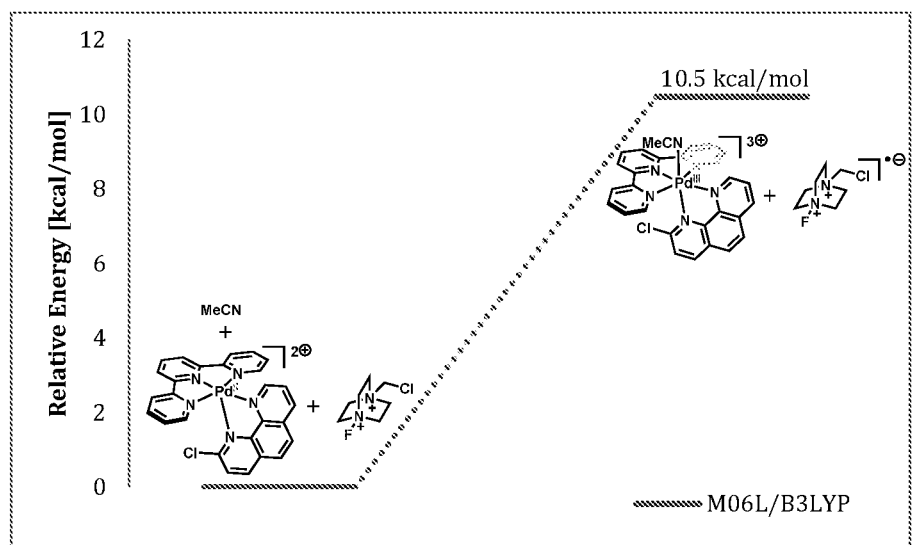
Sum substrates (Hartree): −2978.161708
Sum products (Hartree): −2978.145022

Figure 5A. Energy Profile for F-Atom Transfer with NFSI
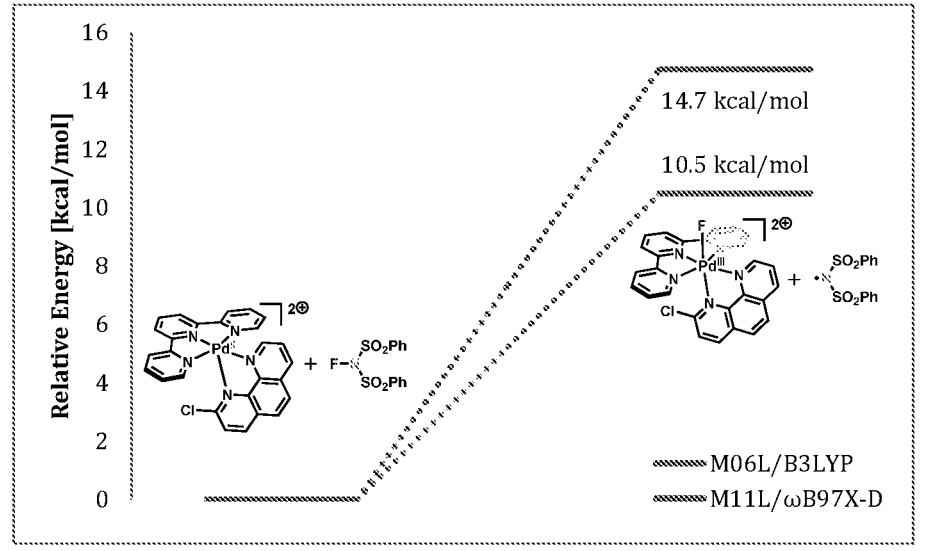
|  | M06L/B3LYP | M11L/ωB97X-D |
|---|---|---|
| Sum substrates (Hartree): | −3616.235918 | −3616.064622 |
| Sum products (Hartree): | −3616.219234 | −3616.041163 |
Figure 5B. Energy Profile for F-Atom Transfer with F-TEDA
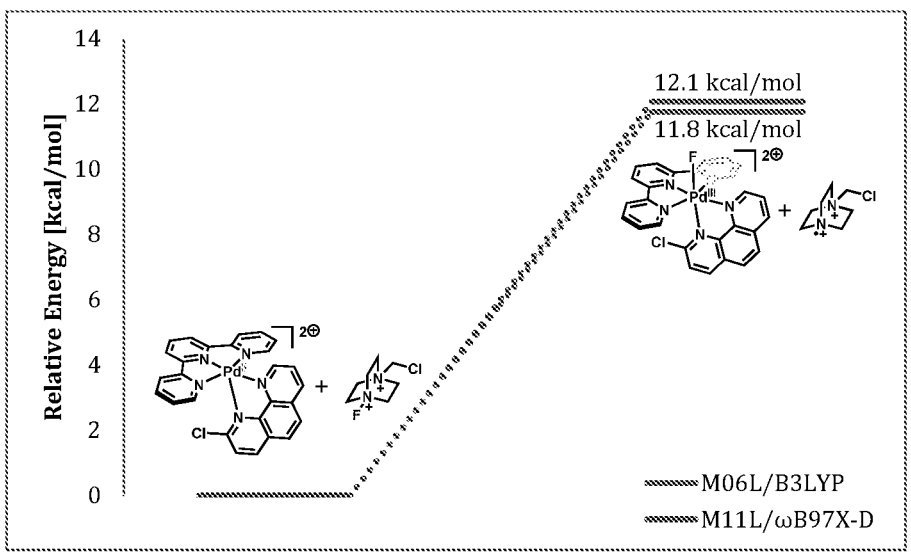
|  | M06L/B3LYP | M11L/ωB97X-D |
|---|---|---|
| Sum substrates (Hartree): | −2845.402161 | −2845.296293 |
| Sum products (Hartree): | −2845.383419 | −2845.277059 |

Figure 6A. Visualization of LUMO of F-TEDA (left) and NFSI (right) with isovalue 0.05.
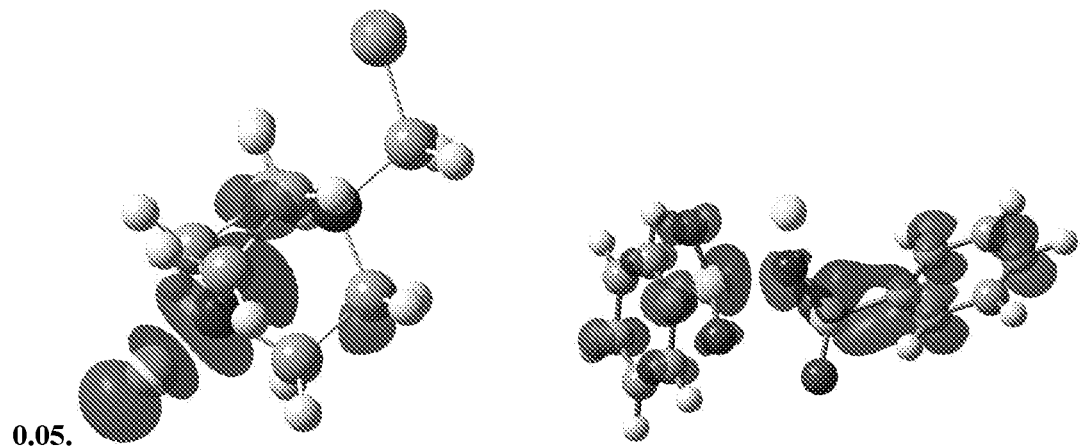
Figure 6B. Visualization of HOMO of 2-Cl-phen-Pd-terpy complex with isovalue 0.05.
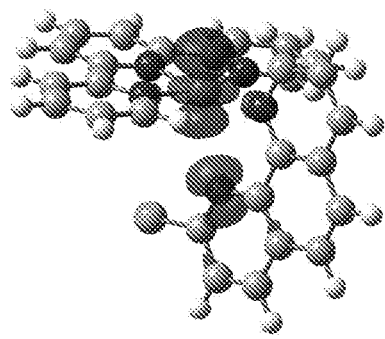
Figure 6C. SOMO of Pd(III)-F complex 5 with isovalue 0.05 and 0.02
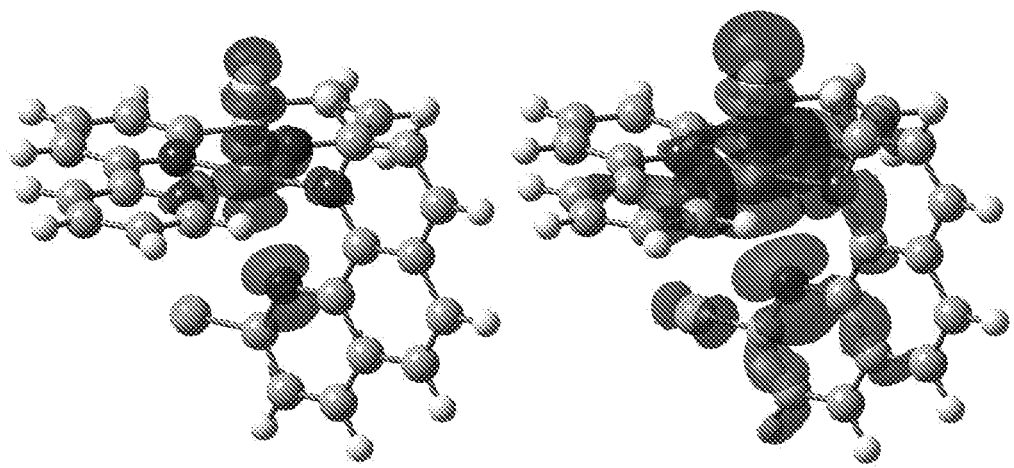

DIRECT PALLADIUM-CATALYZED AROMATIC FLUORINATION

RELATED APPLICATIONS

This application is a national stage filing under 35 U.S.C. § 371 of international PCT application, PCT/US2017/021563, filed Mar. 9, 2017, which claims priority under 35 U.S.C. § 119(e) to U.S. Provisional Application, U.S. Ser. No. 62/305,711, filed Mar. 9, 2016, and to U.S. Provisional Application, U.S. Ser. No. 62/346,326, filed Jun. 6, 2016, each of which is incorporated herein by reference.

BACKGROUND OF THE INVENTION

Substitution of fluoride for hydrogen can have dramatic effects on the physical properties of aromatic compounds' but direct replacement of a hydrogen with a fluoride remains challenging. See, e.g., Chambers, R. D. Fluorine in Organic Chemistry; Oxford: New York, 2004; Campbell, M. G.; Ritter, T. Chem. Rev. 2015, 115, 612. Currently, methods to accomplish aryl C—H to C—F substitution require either fluorine gas or similarly highly activated reagents, or combine high temperature and/or directing groups with milder electrophilic fluorinating reagents. See, e.g., Sandford, G. J. Fluorine Chem. 2007, 128, 90 and references therein; Champagne, P. A.; Desroches, J.; Hamel, J. D.; Vandamme, M.; Paquin, J. F. Chem. Rev. 2015, 115, 9073; Taylor, S. D.; Kotoris, C. C.; Hum, G. Tetrahedron 1999, 55, 12431. The existing methods either: provide uncontrolled di- or polyfluorination; have narrow substrate scope or functional group compatibility; or require multiple equivalents of arene relative to the fluorinating reagent.

Several methods for direct fluorination of C(sp$^3$)-H bonds have recently been disclosed but equivalent methods have not yet been demonstrated for aromatic rings. See, e.g., Champagne, P. A.; Desroches, J.; Hamel, J. D.; Vandamme, M.; Paquin, J. F. Chem. Rev. 2015, 115, 9073. Until now, only electrophilic fluorinating reagents such as F-TEDA-BF$_4$/Selectfluor, fluoropyridinium salts, or fluorinated imides (NFBS) are capable of direct fluorination of aromatic rings, but the reactions of aromatic rings with these reagents are typically successful only with simple, electron-rich substrates or with a large excess of the aryl or heteroaryl substrate. Approaches employing coordinating directing groups have provided access to aryl fluoride products via C—H activation as exemplified by the reports from Sanford and Yu, among others. See, e.g., Hull, K. L.; Anani, W. Q.; Sanford, M. S. J. Am. Chem. Soc. 2006, 128, 7134; Wang, X.; Mei, T. S.; Yu, J. Q. J. Am. Chem. Soc. 2009, 131, 7520. Another notable example of direct fluorination is Fier and Hartwig's 2-fluorination of pyridines and pyridine derivatives with silver fluoride. See, e.g., Fier, P. S.; Hartwig, J. F. Science 2013, 342, 956. These directed fluorination approaches have proven successful with specific motifs. However, there remains a need for a fluorination protocol for more diverse aromatic substrates that does not require a specific molecular substructure.

SUMMARY OF THE INVENTION

Provided herein are novel methods for palladium-catalyzed fluorination of aryl and heteroaryl C—H bonds. Further described herein are palladium complexes, as well as methods of using the palladium complexes to directly fluorinate aryl and heteroaryl compounds. Also described herein are compositions and kits containing the compounds and complexes described herein.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame Ind. 1972) The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and acyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (acyclic, substituted, unsubstituted, branched or unbranched) having 1-6 carbon atoms.

As used herein, "alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, and one or more carbon-carbon double bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, and one or more carbon-carbon triple bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkynyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, sulfur, boron, phosphorus, and silicon ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-14 membered heterocyclyl. In certain embodiments, the heterocyclyl group is substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-14 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. For purposes of this invention, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, NR$^{bb}$C(=O)R$^{aa}$, NR$^{bb}$CO$_2$R$^{aa}$, NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, NR$^{bb}$(=NR$^{bb}$)N(R$^{bb}$)$_2$, —C(=O) NR$^{bb}$SO$_2$R$^{aa}$, NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R is, independently, selected from hydrogen, C$_{1-10}$ alkyl, C$_{1-10}$ haloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O) R$^{ee}$, NR$^{ff}$CO$_2$R$^{ee}$, NR$^{ff}$C(=O)N(R$^{ff}$)$_2$, —C(=NR$^{ff}$) OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C (=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O) SR$^{ee}$, —C(=S)SR$^{ee}$, —SC(=S)SR$^{ee}$, C$_{1-6}$ alkyl, C$_{1-6}$ haloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ haloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ haloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$ X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC (=O)NH(C$_{1-6}$ alkyl), —NHC(=O)NH$_2$, —C(=NH) O(C$_{1-6}$ alkyl), —OC(=NH)(C$_{1-6}$ alkyl), —OC(=NH) OC$_{1-6}$ alkyl, —C(=NH)N(C$_{1-6}$ alkyl)$_2$, —C(=NH) NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH (C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, C$_{1-6}$ alkyl, C$_{1-6}$ haloalkyl, C$_{2-6}$ alkenyl, C$_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is an anionic counterion.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2R^{aa}$, —C(=O)N($R^{bb}$)$_2$, —C(=NR$^{bb}$)$R^{aa}$, —C(=NR$^{bb}$)O$R^{aa}$, —C(=NR$^{bb}$)N($R^{bb}$)$_2$, —C(=O)NR$^{bb}$SO$_2R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=NR$^{bb}$)$R^{aa}$, —C(=NR$^{cc}$)O$R^{aa}$, —C(=NR$^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=NR$^{cc}$)$R^{aa}$, —C(=NR$^{cc}$)O$R^{aa}$, —C(=NR$^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, R and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamante, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methyl sulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethyl silylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethyl silyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —$R^{aa}$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, and —$Si(R^{aa})_3$, wherein $R^{aa}$, $R^{bb}$, and $R^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethyl silyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethyl silylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, —$R^{aa}$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The invention is not intended to be limited in any manner by the above exemplary listing of substituents.

Other Definitions

The following definitions are more general terms used throughout the present application.

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{alkyl})_4^-$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, loweralkyl sulfonate, and aryl sulfonate.

The term "tautomers" or "tautomeric" refers to two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2 $H_2O$) and hexahydrates (R.6 $H_2O$)).

The term "polymorph" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "complex" or "coordination complex" refers to an association of at least one atom or ion (which is referred to as a "central atom," "central ion," or "acceptor," and is usually a metallic cation) and a surrounding array of bound ligands or donors). Ligands are generally bound to a central atom or central ion by a coordinate covalent bond (e.g., ligands may donate electrons from a lone electron pair into an empty orbital of the central atom or central ion) and are referred to as being "coordinated" to the central atom or central ion. There are also organic ligands such as alkenes whose π-bonds can coordinate to empty orbitals of an acceptor. A complex may include one or more donors, which can be the same or different. A complex may also include one or more acceptors, which can be the same or different.

The term "ligand" refers to an ion or molecule that binds to a central atom or ion (e.g., a central metal atom or ion) to form a coordination complex. Ligands are usually electron donors, and the central atom or ion is electron acceptors. The bonding between the central atom or ion and the ligand typically involves formal donation of one or more of the ligand's electron pairs. The nature of such bonding can range from covalent to ionic, and the bond order can range from one to three. One central atom or ion may bind to one or more ligands of the same or different type. A ligand may be capable of binding a central atom or ion through multiple sites, usually because the ligand includes lone pairs on more than one atom of the ligand. Ligands in a complex may affect the reactivity (e.g., ligand substitution rates and redox) of the central atom or ion. Exemplary ligands include charge-neutral ligands ("ligand molecules," e.g., $CH_3CN$, amides (e.g., N,N-dimethylformamide (DMF), N,N-dimethylacetamide (DMA), or N-methyl-2-pyrrolidone (NMP)), dimethyl sulfoxide (DMSO), amines (e.g., ammonia; ethylenediamine (en); pyridine (py); 2,2'-bipyridine (bipy); and 1,10-phenanthroline (phen)), phosphines (e.g., $PPh_3$), ethers (e.g., tetrahydrofuran (THF), 2-methly-tetrahydrofuran, tetrahydropyran, dioxane, diethyl ether, methyl t-butyl ether (MTBE), dimethoxyethane (DME), and diglyme), ketones (e.g., acetone and butanone), chlorohydrocarbons (e.g., dichloromethane (DCM), chloroform, carbon tetrachloride, and 1,2-dichloroethane (DCE)), esters (e.g., propylene carbonate and ethyl acetate), CO, $N_2$, water, and alkenes) and anionic ligands ("ligand ions," e.g., halides, hydride, alkyls, $S_2^-$, $S-CN^-$, $O-NO_2^-$, $N-N_2^-$, $O-H^-$, $[O-C(=O)-C(=O)-O]_2^-$, $O-N-O^-$, $N=C=S^-$, $CN^-$).

The term "transition metal" refers to elements that are in the d-block and f-block of the Periodic Chart of the Elements, which may exhibit a variety of oxidation states, and which may form numerous complex ions. The term "d-block" refers to those elements that have electrons filling the 3d, 4d, 5d, and 6d orbitals, and the term "f-block" refers to those elements (including lanthanides and the actinides) that have electrons filling the 4f and 5f orbitals. Exemplary transition metals include palladium, nickel, cobalt, copper, platinum, silver, manganese, zinc, iridium, rhodium, iron, and ruthenium. The term "transition metal" also includes alloys, metal/metal composites, metal ceramic composites, and metal polymer composites, as well as other metal composites.

The term "catalysis," "catalyze," or "catalytic" refers to the increase in rate of a reaction due to the participation of a substance called a "catalyst." In certain embodiments, the amount and nature of a catalyst remains essentially unchanged during a reaction. In certain embodiments, a catalyst is regenerated, or the nature of a catalyst is essentially restored after a reaction. A catalyst may participate in multiple chemical transformations. The effect of a catalyst may vary due to the presence of other substances known as inhibitors or poisons (which reduce the catalytic activity) or promoters (which increase the activity). Catalyzed reactions have a lower activation energy (rate-limiting free energy of activation) than the corresponding uncatalyzed reaction, resulting in a higher reaction rate at the same temperature. Catalysts may affect the reaction environment favorably, or bind to the reagents to polarize bonds, or form specific intermediates that are not typically produced by a uncatalyzed reaction, or cause dissociation of reagents to reactive forms.

A "anionic counterion" is a negatively charged group associated with a positively charged group in order to maintain electronic neutrality. A anionic counterion may carry one or more (e.g., two, three, or four) negative charges. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, ethanoate, propanoate, benzoate, glycerate, lactate, tartrate, glycolate, and the like), $BF_4^-$, $PF_4^-$, $PF_6^-$, $SbF_6^-$, $B[3,5-(CF_3)_2C_6H_3]_4^-$, $BPh_4^-$, $Al(OC(CF_3)_3)_4^-$, and a carborane anion (e.g., $CB_{11}H_{12}^-$ or $(HCB_{11}Me_5Br_6)^-$).

The term "cationic counterion" refers to a positively charged group associated with a negatively charged group in order to maintain electronic neutrality. A cationic counterion may carry one or more (e.g., two, three, four, five, six, or seven) positive charges. A cationic counterion may be an organic or inorganic counterion. A cationic counterion may be a metal or non-metal cation. In certain embodiments, a cationic counterion is a monovalent metal cation (e.g., a cationic alkali metal counterion, such as $Li^+$, $Na^+$, $K^+$, $Rb^+$, or $Cs^+$). In other embodiments, a cationic counterion is a divalent (e.g., cationic alkaline earth metal counterion, such as $Be^{2+}$, $Mg^{2+}$, $Ca^{2+}$, $Sr^{2+}$, or $Ba^{2+}$), trivalent, tetravalent, pentavalent, hexavalent, or heptavalent metal cation. In certain embodiments, a cationic counterion is a cationic, quaternary amine counterion, such as an ammonium ion, tetramethylammonium ion, tetraethylammonium ion, tetrapropylammonium ion, tetrabutylammonium ion, or pyridinium ion.

The term "non-coordinating anionic counterion" refers to an anion that interacts weakly with cations. Exemplary non-coordinating anions include, but are not limited to, $ClO_4^-$, $OTf^-$, $BF_4^-$, $PF_4^-$, $PF_6^-$, and $SbF_6^-$. Other examples of non-coordinating anions include, but are not limited to, $B[3,5-(CF_3)_2C_6H_3]_4^-$, $BPh_4^-$, $Al(OC(CF_3)_3)_4^-$, or a carborane anion (e.g., $CB_{11}H_{12}^-$ or $(HCB_{11}Me_5Br_6)^-$).

The term "isotopes" refers to variants of a particular chemical element such that, while all isotopes of a given element share the same number of protons in each atom of the element, those isotopes differ in the number of neutrons. The term "radioactivity" or "radioactive decay" refers to the process by which a nucleus of an unstable isotope (e.g., $^{18}F$) loses energy by emitting particles or rays (e.g., alpha particles, beta particles, and gamma rays) of ionizing radiation. Such an unstable isotope or a material including the unstable isotope is referred to as "radioactive." The Curie (Ci) is a non-SI (non-International System of Units) unit of radioactivity and is defined as 1 $Ci=3.7\times10^{10}$ decays per second. The term "specific activity" refers to the unit radioactivity of a material (e.g., a compound of Formula (I), or a salt, tautomer, stereoisomer, or isotopically labeled derivative (e.g., $^{18}F$ labeled derivative) thereof). In certain embodiments, the term "specific activity" refers to the radioactivity of a material per micromole (µmol) of the material.

BRIEF DESCRIPTION OF THE DRAWINGS

FIG. 4A shows the Density Functional Theory (DFT) energy profile for compound 1 (Catalyst) with N-fluorobenzenesulfonimide (NFSI). FIG. 4B shows the DFT energy profile for single-electron-transfer (SET.) between Catalyst and Selectfluor (F-Teda).

FIG. 5A shows the DFT energy profile for F-Atom Transfer with NFSI. FIG. 5B shows the DFT energy profile for F-Atom Transfer with F-Teda.

FIGS. 6A-6C show a spin density plot for compound 1. FIG. 6A shows a visualization of LUMO of F-TEDA (left) and NFSI (right) with isovalue 0.05, for compound 1. FIG. 6B shows a visualization of HOMO of 2-Cl-phen-Pd-terpy complex with isovalue 0.05. FIG. 6C shows a visualization of SOMO of Pd(III)-F complex 5 with isovalue 0.05 and 0.02.

DETAILED DESCRIPTION OF CERTAIN EMBODIMENTS

Figure 1:
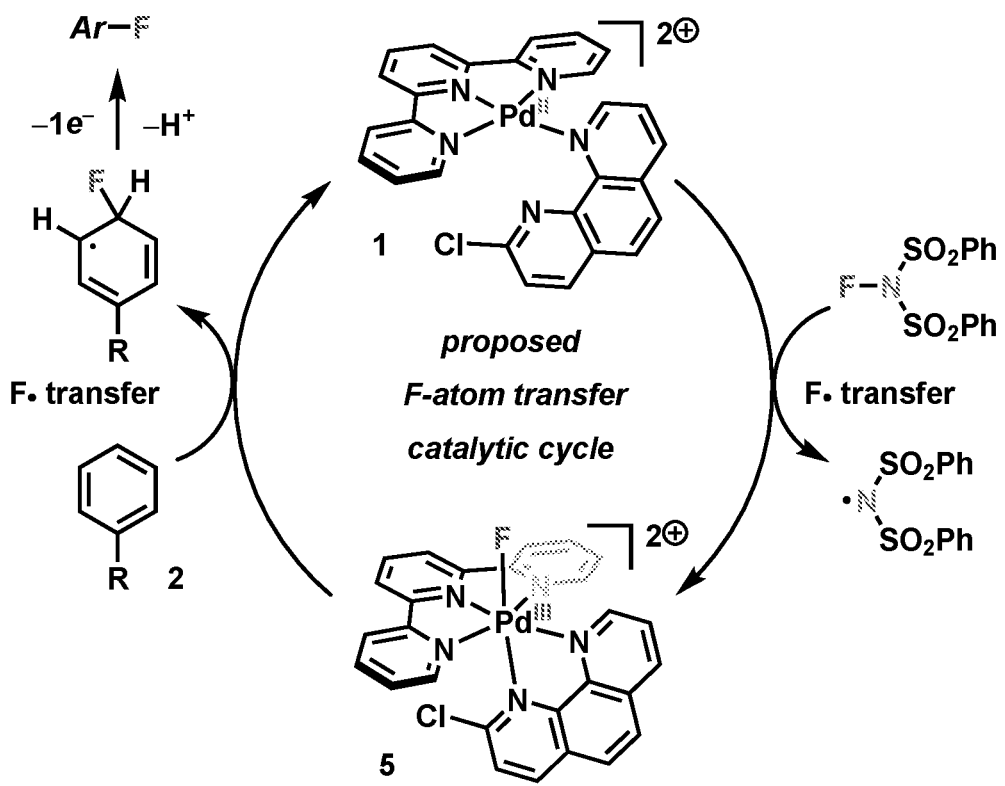
FIG. 1 shows the proposed F-atom transfer catalytic cycle for exemplary compounds described herein.

Described herein is a palladium-catalyzed process for the preparation of aryl and heteroaryl fluorides, such as compounds of Formula (I), (II), and (III), from aryl and heteroaryl substrates, such as compounds of Formula (D), (E), and (F):

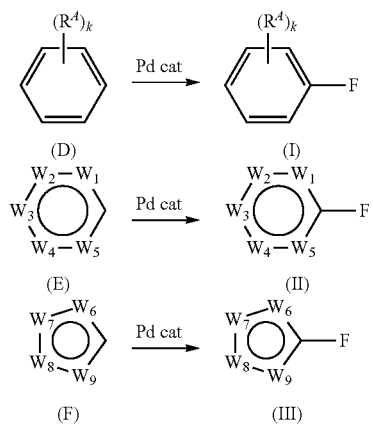

wherein:

$W_1$, $W_2$, $W_3$, $W_4$, and $W_5$ is CH, $CR^A$, or N, provided at least one of $W_1$, $W_2$, $W_3$, $W_4$, and $W_5$ is N;

$W_6$, $W_7$, $W_8$, and $W_9$ is CH, $CR^A$, N, NH, $NR^A$, O, or S, provided at least one of $W_6$, $W_7$, $W_8$, and $W_9$ is N, NH, $NR^A$, O, or S;

each instance of $R^A$ is independently halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{41}$, —$N(R^{41})_2$, —$SR^{41}$, —CN, —SCN, —C(=$NR^{41}$)$R^{41}$, —C(=$NR^{41}$)$OR^{41}$, —C(=$NR^{41}$)N($R^{41}$)$_2$, —C(=O)$R^{41}$, —C(=O)$OR^{41}$, —C(=O)N($R^{41}$)$_2$, —$NO_2$, —$NR^{41}$C(=O)$R^{41}$, —$NR^{41}$C(=O)$OR^{41}$, —$NR^{41}$C(=O)N($R^{41}$)$_2$, —OC(=O)$R^{41}$, —OC(=O)$OR^{41}$, or —OC(=O)N($R^{41}$)$_2$, or two vicinal $R^A$ groups (groups attached to two adjacent carbon atoms) are joined to form a substituted or unsubstituted carbocyclyl, substituted or unsubstituted heterocyclyl, substituted or unsubstituted aryl, or substituted or unsubstituted heteroaryl ring;

each instance of $R^{41}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{41}$ attached the same nitrogen atom are joined to form a substituted or unsubstituted heterocyclic or substituted or unsubstituted heteroaryl ring; and k is 0, 1, 2, 3, 4, or 5.

In one aspect, provided herein is a method of preparing a compound of Formula (I), (II), or (III), comprising contacting an aryl substrate of Formula (D), or a heteroaryl substrate of Formula (E) or (F), with a palladium complex, wherein the palladium complex comprises a bidentate ligand of Formula (B) and a tridentate ligand of Formula (A'):

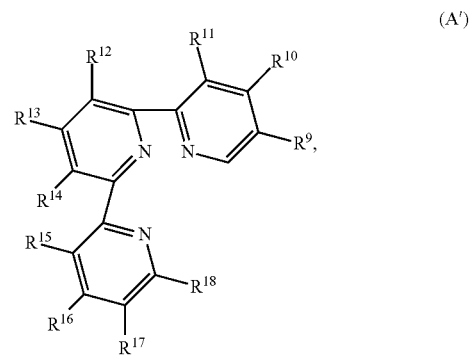

(B)

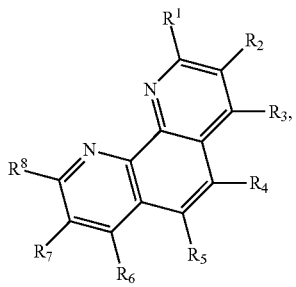

wherein R¹ to R¹⁸ are described herein.

In certain embodiments, the method further comprises a fluorinating agent as described herein. Also provided herein is a palladium complex comprising a ligand of Formula (B) and a ligand of Formula (A') and compositions thereof. In certain embodiments, the palladium of the complex is palladium (II). In certain embodiments, the palladium of the complex is palladium (III). In certain embodiments, the palladium complex further comprises a fluoro (F) ligand. In certain embodiments, the palladium complex comprises palladium (III) and a fluoro (F) ligand.

In one aspect, provided herein is a method of preparing a compound of Formula (I) comprising:

contacting a palladium(II) complex of formula (A) with a phenanthroline ligand of formula (B) to form a palladium(II) catalyst of formula (C); and contacting an aryl substrate of Formula (D), or a heteroaryl substrate of formula (E) or (F), with a fluorinating agent in the presence of the palladium (II) catalyst of Formula (C) to provide the compound of Formula (I), (II), or (III).

Formula A, B, and C are as follows:

(A)

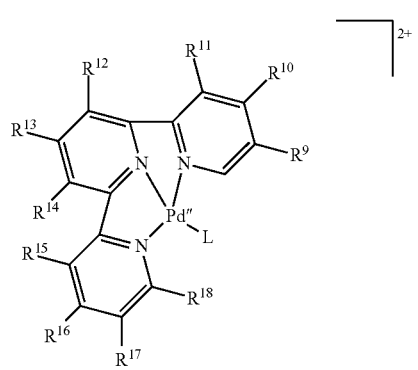

(B)

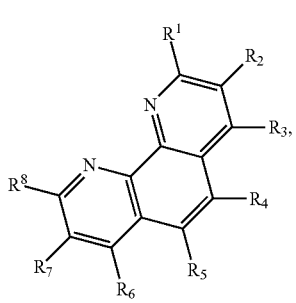

(C)

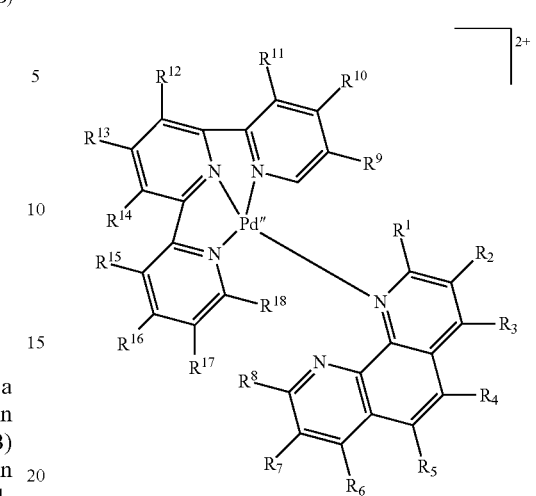

wherein:
each instance of $R^A$ is independently halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{41}$, $-N(R^{41})_2$, $-SR^{41}$, $-CN$, $-SCN$, $-C(=NR^{41})R^{41}$, $-C(=NR^A)OR^{41}$, $-C(=NR^{41})N(R^{41})_2$, $-C(=O)R^{41}$, $-C(=O)OR^{41}$, $-C(=O)N(R^{41})_2$, $-NO_2$, $-NR^{41}C(=O)R^{41}$, $-NR^{41}C(=O)OR^{41}$, $-NR^{41}C(=O)N(R^{41})_2$, $-OC(=O)R^{41}$, $-OC(=O)OR^{41}$, or $-OC(=O)N(R^{41})_2$, or two vicinal $R^A$ groups (groups attached to two adjacent carbon atoms) are joined to form a substituted or unsubstituted carbocyclyl, substituted or unsubstituted heterocyclyl, substituted or unsubstituted aryl, or substituted or unsubstituted heteroaryl ring;

each instance of $R^{41}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{41}$ attached the same nitrogen atom are joined to form a substituted or unsubstituted heterocyclic or substituted or unsubstituted heteroaryl ring;

k is 0, 1, 2, 3, 4, or 5;

Y is an anionic counterion or Y is an alkenyl or alkynyl moiety;

L is an uncharged, monodentate ligand selected from the group consisting of carbon monoxide, an isonitrile (e.g., tert-butylisonitrile, cyclohexylisonitrile, adamantylisonitrile), an acetonitrile (e.g., —NCMe), an amine (e.g., trimethylamine, trimethylamine), morpholine, phosphines (e.g., trifluorophosphine), aliphatic, aromatic or heteroaromatic phosphines (e.g, trimethylphoshine, tricyclohexylphosphine, dicyclohexylphenylphosphine, tri-o-tolylphosphine, tri-tert-butylphosphine, tri-phenylphosphine, tris(pentafluorophenyl)phosphine), phosphites (e.g., trimethyl phosphite, triethyl phosphite), arsines (e.g., trifluoroarsine, trimethylarsine, tricyclohexylarsine, tri-tert-butylarsine, triphenylarsine, tris(pentafluorophenyl)-arsine), stibines (e.g., trifluorostibine, trimethylstibine, tricyclohexylstibine, tri-tert-butylstibine, triphenylstibine, tris(pentafluoro-phenyl) stibine, or a nitrogen-containing heterocycle (e.g., pyridine, pyridazine, pyrazine, triazine);

$R^1$, $R^2$, $R^3$, $R^4$, $R^5$, $R^6$, $R^7$, and $R^8$ are independently selected from the group consisting of hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N(R)$_2$, —SR, —CN, —SCN, —C(=NR)R, —C(=NR)OR, —C(=NR)N(R)$_2$, —C(=O)R, —C(=O)OR, —C(=O)N(R)$_2$, —NO$_2$, —NRC(=O)R, —NRC(=O)OR, —NRC(=O)N(R)$_2$, —OC(=O)R, —OC(=O)OR, —OC(=O)N(R)$_2$, —SO$_3$H, and —NR$_3^+$Y' wherein Y' is an anionic counterion;

each instance of R is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R attached the same nitrogen atom are joined to form a substituted or unsubstituted heterocyclic or substituted or unsubstituted heteroaryl ring;

$R^9$, $R^{10}$, $R^{11}$, $R^{12}$, $R^{13}$, $R^{14}$, $R^{15}$, $R^{16}$, $R^{17}$, and $R^{18}$ are independently selected from the group consisting of hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N(R)$_2$, —SR, —CN, —SCN, —C(=NR)R, —C(=NR)OR, —C(=NR)N(R)$_2$, —C(=O)R, —C(=O)OR, —C(=O)N(R)$_2$, —NO$_2$, —NRC(=O)R, —NRC(=O)OR, —NRC(=O)N(R)$_2$, —OC(=O)R, —OC(=O)OR, —OC(=O)N(R)$_2$, —SO$_3$H, and —NR$_3^+$Y' wherein Y' is an anionic counterion.

In another aspect, the method of preparing a compound of Formula (I), (II), or (II), comprises contacting an aryl substrate of Formula (D), or a heteroaryl substrate of Formula (E) or (F), with a fluorinating agent in the presence of a palladium (II) catalyst of Formula (C) to provide the compound of Formula (I), (II), or (III).

In certain embodiments, the fluorination method is performed at a temperature ranging from about 0-10° C., 10-20° C., 20-30° C., 30-40° C., or 40-50° C., 60-70° C., or 70-80° C.

Provided herein is a palladium catalyst of Formula (C) and compositions thereof.

As shown below by the black arrows (structures herein are not drawn to scale), the three nitrogens of the terpyridine derived ligand and one nitrogen of the phenanthroline derived ligand form a Pd complex of square planar geometry. The other nitrogen of the phenanthroline derived ligand has an antibonding interaction with the dz2-based orbital on palladium. This interaction likely facilitates oxidation to a high valent palladium complex such as a palladium(III) complex of Formula (G) with an octahedral geometry (or distorted octahedral due to Jahn Teller distortion) because in the high valent state of Pd, the interaction from Pd to the nitrogen becomes bonding.

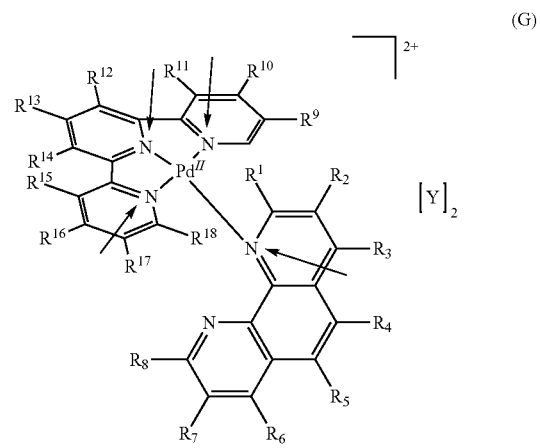

In certain embodiments of Formula (C), $R^9$ to $R^{18}$ are hydrogen; $R^1$ to $R^7$ are hydrogen; and $R^8$ is hydrogen, halogen, —COR, —COOR —CN, —SO$_3$H, —NO$_2$, haloalkyl, or —NR$_3^+$Y' In certain embodiments, $R^9$ to $R^{18}$ are hydrogen; $R^1$ to $R^7$ are hydrogen; and $R^8$ is halogen. In certain embodiments of Formula (C), $R^8$ is halogen. In certain embodiments, $R^8$ is Br or Cl. In certain embodiments, $R^8$ is Cl.

In certain embodiments, the compound of formula (C) is a compound of formula (C-1):

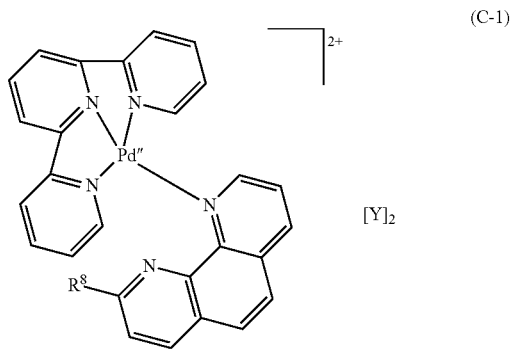

wherein $R^8$ is halogen and Y is BF$_4^-$ or OTf$^-$. In certain embodiments of C-1, $R^8$ is Cl and Y is BF$_4^-$.

In certain embodiments, the palladium catalyst of Formula (C) is formed in situ. For example, Pd(OAc)$_2$ is reacted with terpyridine or a derivative thereof in an appropriate solvent, such as acetonitrile (MeCN), in the presence of a reagent, such as HBF$_4$.OEt$_2$. Other solvents are known in the art and include, but not limited to, MeCN, acetone, acetic anhydride (Ac$_2$O), propylene carbonate, chloroform, diglyme, dimethoxyethane (DME), tetrahydrofuan (THF), butanone, and tert-butyl methyl ether (TBME). In certain embodiments, the palladium catalyst is prepared prior to the fluorination reaction. For example, a commercially available palladium source such as Pd(MeCN)$_4$(BF$_4$)$_2$ and ligands (e.g., terpyrdine or derivatives thereof, such as those of Formula A', and/or phenanthroline or derivatives thereof, such as those of Formula B) can be used to prepare the palladium catalyst of Formula (C).

Without wishing to be bound by theory, the catalytic cycle for direct C—H fluorination using the palladium complexes described herein is thought to involve a Pd(III)-F complex of Formula (G). Therefore, provided herein is a palladium catalyst of Formula (G):

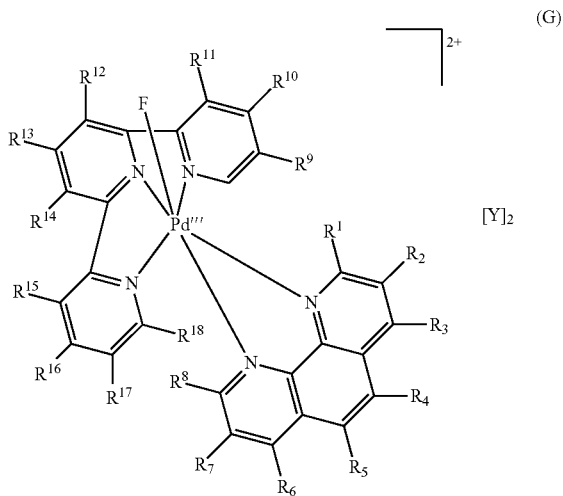

(G)

wherein $R^1$ to $R^{18}$ and Y are as described herein. The various general and specific embodiments described for Formula C are applicable to Formula E.

In certain embodiments, the compound of Formula E is a compound of Formula G-1:

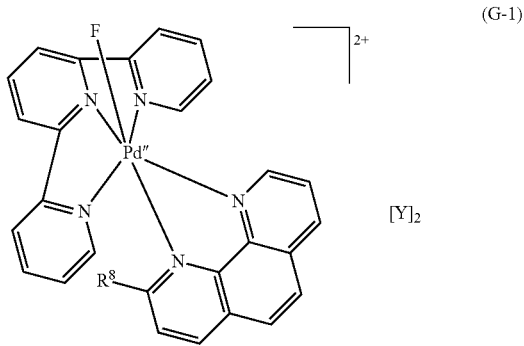

(G-1)

wherein $R^8$ is halogen and Y is $BF_4^-$ or $OTf^-$. In certain embodiments of Formula E-1, $R^8$ is Cl and Y is $BF_4^-$.

The proposed mechanism of aryl or heteroaryl fluorination is exemplified by the mechanism depicted in FIG. 1. Based on mechanistic experiments, it is proposed that a catalytic cycle proceeds whereby Pd(III)-F is formed via F atom transfer from the N—F oxidant to a dicationic Pd(II). For reviews of Pd(III) complexes, see Powers, D. C.; Ritter, T. Top. Organomet. Chem. 2011, 503, 129; andMirica, L. M.; Khusnutdinova, J. R. Coord. Chem. Rev. 2012, 257, 299. For references describing mononuclear Pd(III) complexes, seeLanci, M. P.; Remy, M. S.; Kaminsky, W.; Mayer, J. M.; Sanford, M. S. J. Am. Chem. Soc. 2009, 131, 15618; Khusnutdinova, J. R.; Rath, N. P.; Mirica, L. M. J. Am. Chem. Soc. 2012, 134, 2414; andKhusnutdinova, J. R.; Rath, N. P.; Mirica, L. M. Inorg. Chem. 2014, 53, 13112. Fluorine atom transfer from the Pd(III)-F to the aryl or heteroaryl substrate then forms the carbon-fluorine bond. Subsequent oxidation and deprotonation steps can then provide the aryl or heteroaryl fluoride product.

Variables $R^1$, $R^2$, $R^3$, $R^4$, $R^5$, $R^6$, $R^7$, $R^8$

As generally defined herein, $R^1$, $R^2$, $R^3$, $R^4$, $R^5$, $R^6$, $R^7$, and $R^8$ are independently selected from the group consisting of hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N(R)$_2$, —SR, —CN, —SCN, —C(=NR)R, —C(=NR)OR, —C(=NR)N(R)$_2$, —C(=O)R, —C(=O)OR, —C(=O)N(R)$_2$, —NO$_2$, —NRC(=O)R, —NRC(=O)OR, —NRC(=O)N(R)$_2$, —OC(=O)R, —OC(=O)OR, —OC(=O)N(R)$_2$, —SO$_3$H, and —NR$_3^+$Y' wherein Y' is an anionic counterion, and wherein each instance of R is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R attached the same nitrogen atom are joined to form a substituted or unsubstituted heterocyclic or substituted or unsubstituted heteroaryl ring.

In certain embodiments, the phenanthroline ligand of Formula B is electron deficient. For example, in certain embodiments, $R^1$, $R^2$, $R^3$, $R^4$, $R^5$, $R^6$, $R^7$, and $R^8$ are independently selected from the group consisting of hydrogen, halogen, —COR, —COOR —CN, —SO$_3$H, —NO$_2$, haloalkyl, or —NR$_3^+$Y', wherein each instance of R is independently hydrogen or substituted or unsubstituted alkyl. In certain embodiments, $R^1$, $R^2$, $R^3$, $R^4$, $R^5$, $R^6$, $R^7$, and $R^8$ are hydrogen. In certain embodiments, $R^1$, $R^2$, $R^3$, $R^4$, $R^5$, $R^6$, $R^7$ are hydrogen and $R^8$ is halogen, —COR, —COOR —CN, —SO$_3$H, —NO$_2$, haloalkyl, or —NR$_3^+$Y', wherein each instance of R is independently hydrogen or substituted or unsubstituted alkyl. In certain embodiments, $R^8$ is halogen. In certain embodiments, $R^1$, $R^2$, $R^3$, $R^4$, $R^5$, $R^6$, and $R^8$ are hydrogen and $R^7$ is halogen, —COR, —COOR —CN, —SO$_3$H, —NO$_2$, haloalkyl, or —NR$_3$+Y', wherein each instance of R is independently hydrogen or substituted or unsubstituted alkyl. In certain embodiments, $R^7$ is halogen. In certain embodiments, $R^1$, $R^2$, $R^3$, $R^4$, $R^5$, $R^7$, and $R^8$ are hydrogen and $R^6$ is halogen, —COR, —COOR —CN, —SO$_3$H, —NO$_2$, haloalkyl, or —NR$_3^+$Y', wherein each instance of R is independently hydrogen or substituted or unsubstituted alkyl. In certain embodiments, $R^6$ is halogen. In certain embodiments, $R^1$, $R^2$, $R^3$, $R^4$, $R^6$, $R^7$, and $R^8$ are hydrogen and $R^5$ is halogen, —COR, —COOR —CN, —SO$_3$H, —NO$_2$, haloalkyl, or —NR$_3^+$Y', wherein each instance of R is independently hydrogen or substituted or unsubstituted alkyl. In certain embodiments, $R^5$ is halogen. In certain embodiments, $R^1$, $R^2$, $R^3$, $R^5$, $R^6$, $R^7$, and $R^8$ are hydrogen and $R^4$ is halogen, —COR, —COOR —CN, —SO$_3$H, —NO$_2$, haloalkyl, or —NR$_3^+$Y', wherein each instance of R is independently hydrogen or substituted or unsubstituted alkyl. In certain embodiments, $R^4$ is halogen. In certain embodiments, $R^1$, $R^2$, $R^4$, $R^5$, $R^6$, $R^7$, and $R^8$ are hydrogen and $R^3$ is halogen, —COR, —COOR —CN, —SO$_3$H, —NO$_2$, haloalkyl, or —NR$_3^+$Y', wherein each instance of R is independently hydrogen or substituted or unsubstituted alkyl. In certain embodiments, $R^3$ is halogen. In certain embodiments, $R^1$, $R^3$, $R^4$, $R^5$, $R^6$, $R^7$, and $R^8$ are hydrogen and $R^2$ is halogen, —COR, —COOR —CN, —SO$_3$H, —NO$_2$, haloalkyl, or —NR$_3^+$Y', wherein each instance of R is independently hydrogen or substituted or unsubstituted alkyl. In certain embodiments, $R^2$ is halogen. In certain embodiments, $R^2$, $R^3$, $R^4$, $R^5$, $R^6$, $R^7$, and $R^8$ are hydrogen and $R^1$ is halogen, —COR, —COOR —CN, —SO$_3$H, —NO$_2$, haloalkyl, or —NR$_3^+$Y', wherein each instance of R is independently hydrogen or substituted or unsubstituted alkyl. In certain embodiments, $R^1$ is halogen.

In certain embodiments, two of $R^1$, $R^2$, $R^3$, $R^4$, $R^5$, $R^6$, $R^7$, and $R^8$ are each independently halogen, —COR, —COOR —CN, —SO$_3$H, —NO$_2$, haloalkyl, or —NR$_3^+$Y', wherein each instance of R is independently hydrogen or substituted or unsubstituted alkyl. In certain embodiments, three of $R^1$, $R^2$, $R^3$, $R^4$, $R^5$, $R^6$, $R^7$, and $R^8$ are each independently halogen, —COR, —COOR —CN, —SO$_3$H, —NO$_2$, haloalkyl, or —NR$_3^+$Y', wherein each instance of R is independently hydrogen or substituted or unsubstituted alkyl. In certain embodiments, four of $R^1$, $R^2$, $R^3$, $R^4$, $R^5$, $R^6$, $R^7$, and $R^8$ are each independently halogen, —COR, —COOR —CN, —SO$_3$H, —NO$_2$, haloalkyl, or —NR$_3^+$Y', wherein each instance of R is independently hydrogen or substituted or unsubstituted alkyl. In certain embodiments, five of $R^1$, $R^2$, $R^3$, $R^4$, $R^5$, $R^6$, $R^7$, and $R^8$ are each independently halogen, —COR, —COOR —CN, —SO$_3$H, —NO$_2$, haloalkyl, or —NR$_3^+$Y', wherein each instance of R is independently hydrogen or substituted or unsubstituted alkyl. In certain embodiments, six of $R^1$, $R^2$, $R^3$, $R^4$, $R^5$, $R^6$, $R^7$, and $R^8$ are each independently halogen, —COR, —COOR —CN, —SO$_3$H, —NO$_2$, haloalkyl, or —NR$_3^+$Y', wherein each instance of R is independently hydrogen or substituted or unsubstituted alkyl. In certain embodiments, seven of $R^1$, $R^2$, $R^3$, $R^4$, $R^5$, $R^6$, $R^7$, and $R^8$ are each independently halogen, —COR, —COOR —CN, —SO$_3$H, —NO$_2$, haloalkyl, or —NR$_3^+$Y', wherein each instance of R is independently hydrogen or substituted or unsubstituted alkyl. In certain embodiments, all of $R^1$, $R^2$, $R^3$, $R^4$, $R^5$, $R^6$, $R^7$, and $R^8$ are each independently halogen, —COR, —COOR —CN, —SO$_3$H, —NO$_2$, haloalkyl, or —NR$_3^+$Y', wherein each instance of R is independently hydrogen or substituted or unsubstituted alkyl.

Variables $R^9$, $R^{10}$, $R^{11}$, $R^{12}$, $R^{13}$, $R^{14}$, $R^{15}$, $R^{16}$, $R^{17}$, $R^{18}$ As generally defined herein, $R^9$, $R^{10}$, $R^{11}$, $R^{12}$, $R^{13}$, $R^{14}$, $R^{15}$, $R^{16}$, $R^{17}$, and $R^{18}$ are independently selected from the group consisting of hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N(R)$_2$, —SR, —CN, —SCN, —C(=NR)R, —C(=NR)OR, —C(=NR)N(R)$_2$, —C(=O)R, —C(=O)OR, —C(=O)N(R)$_2$, —NO$_2$, —NRC(=O)R, —NRC(=O)OR, —NRC(=O)N(R)$_2$, —OC(=O)R, —OC(=O)OR, —OC(=O)N(R)$_2$, —SO$_3$H, and —NR$_3^+$Y' wherein Y' is an anionic counterion, wherein each instance of R is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R attached the same nitrogen atom are joined to form a substituted or unsubstituted heterocyclic or substituted or unsubstituted heteroaryl ring.

In certain embodiments, $R^{10}$, $R^{11}$, $R^{12}$, $R^{13}$, $R^{14}$, $R^{15}$, $R^{16}$, $R^{17}$, and $R^{18}$ are hydrogen and $R^9$ is selected from the foregoing non-hydrogen groups. In certain embodiments, $R^9$, $R^{11}$, $R^{12}$, $R^{13}$, $R^{14}$, $R^{15}$, $R^{16}$, $R^{17}$, and $R^{18}$ are hydrogen and $R^{10}$ is selected from the foregoing non-hydrogen groups. In certain embodiments, $R^9$, $R^{10}$, $R^{12}$, $R^{13}$, $R^{14}$, $R^{15}$, $R^{16}$, $R^{17}$, and $R^{18}$ are hydrogen and $R^{11}$ is selected from the foregoing non-hydrogen groups. In certain embodiments, $R^9$, $R^{10}$, $R^{11}$, $R^{13}$, $R^{14}$, $R^{15}$, $R^{16}$, $R^{17}$, and $R^{18}$ are hydrogen and $R^{12}$ is selected from the foregoing non-hydrogen groups. In certain embodiments, $R^9$, $R^{10}$, $R^{11}$, $R^{12}$, $R^{14}$, $R^{15}$, $R^{16}$, $R^{17}$, and $R^{18}$ are hydrogen and $R^{13}$ is selected from the foregoing non-hydrogen groups. In certain embodiments, $R^9$, $R^{10}$, $R^{11}$, $R^{12}$, $R^{13}$, $R^{15}$, $R^{16}$, $R^{17}$, and $R^{18}$ are hydrogen and $R^{14}$ is selected from the foregoing non-hydrogen groups. In certain embodiments, $R^9$, $R^{10}$, $R^{11}$, $R^{12}$, $R^{13}$, $R^{14}$, $R^{16}$, $R^{17}$, and $R^{18}$ are hydrogen and $R^{15}$ is selected from the foregoing non-hydrogen groups. In certain embodiments, $R^9$, $R^{10}$, $R^{11}$, $R^{12}$, $R^{13}$, $R^{14}$, $R^{15}$, $R^{17}$, and $R^{18}$ are hydrogen and $R^{16}$ is selected from the foregoing non-hydrogen groups. In certain embodiments, $R^9$, $R^{10}$, $R^{11}$, $R^{12}$, $R^{13}$, $R^{14}$, $R^{15}$, $R^{16}$, and $R^{18}$ are hydrogen and $R^{17}$ is selected from the foregoing non-hydrogen groups. In certain embodiments, $R^9$, $R^{10}$, $R^{11}$, $R^{12}$, $R^{13}$, $R^{14}$, $R^{15}$, $R^{16}$, and $R^{17}$ are hydrogen and $R^{18}$ is selected from the foregoing non-hydrogen groups.

In certain embodiments, two of $R^9$, $R^{10}$, $R^{11}$, $R^{12}$, $R^{13}$, $R^{14}$, $R^{15}$, $R^{16}$, $R^{17}$, and $R^{18}$ are independently selected from the foregoing non-hydrogen groups. In certain embodiments, three of $R^9$, $R^{10}$, $R^{11}$, $R^{12}$, $R^{13}$, $R^{14}$, $R^{15}$, $R^{16}$, $R^{17}$, and $R^{18}$ are independently selected from the foregoing non-hydrogen groups. In certain embodiments, four of $R^9$, $R^{10}$, $R^{11}$, $R^{12}$, $R^{13}$, $R^{14}$, $R^{15}$, $R^{16}$, $R^{17}$, and $R^{18}$ are independently selected from the foregoing non-hydrogen groups. In certain embodiments, five of $R^9$, $R^{10}$, $R^{11}$, $R^{12}$, $R^{13}$, $R^{14}$, $R^{15}$, $R^{16}$, $R^{17}$, and $R^{18}$ are independently selected from the foregoing non-hydrogen groups.

In certain embodiments, $R^9$, $R^{10}$, $R^{11}$, $R^{12}$, $R^{13}$, $R^{14}$, $R^{15}$, $R^{16}$, $R^{17}$, and $R^{18}$ are hydrogen. In certain embodiments, one of $R^9$, $R^{10}$, $R^{11}$, $R^{12}$, $R^{13}$, $R^{14}$, $R^{15}$, $R^{16}$, $R^{17}$, and $R^8$ is halogen. In certain embodiments, one of $R^9$, $R^{10}$, $R^{11}$, $R^{12}$, $R^{13}$, $R^{14}$, $R^{15}$, $R^{16}$, $R^{17}$, and $R^{18}$ is acyl. In certain embodiments, one of $R^9$, $R^{10}$, $R^{11}$, $R^{12}$, $R^{13}$, $R^{14}$, $R^{15}$, $R^{16}$, $R^{17}$, and $R^{18}$ is substituted or unsubstituted alkyl. In certain embodiments, one of $R^9$, $R^{10}$, $R^{11}$, $R^{12}$, $R^{13}$, $R^{14}$, $R^{15}$, $R^{16}$, $R^{17}$, and $R^{18}$ is substituted or unsubstituted alkenyl. In certain embodiments, one of $R^9$, $R^{10}$, $R^{11}$, $R^{12}$, $R^{13}$, $R^{14}$, $R^{15}$, $R^{16}$, $R^{17}$, and $R^{18}$ is substituted or unsubstituted alkynyl. In certain embodiments, one of $R^9$, $R^{10}$, $R^{11}$, $R^{12}$, $R^{13}$, $R^{14}$, $R^{15}$, $R^{16}$, $R^{17}$, and $R^{18}$ is substituted or unsubstituted carbocyclyl. In certain embodiments, one of $R^9$, $R^{10}$, $R^{11}$, $R^{12}$, $R^{13}$, $R^{14}$, $R^{15}$, $R^{16}$, $R^{17}$, and $R^{18}$ is substituted or unsubstituted heterocyclyl. In certain embodiments, one of $R^9$, $R^{10}$, $R^{11}$, $R^{12}$, $R^{13}$, $R^{14}$, $R^{15}$, $R^{16}$, $R^{17}$, and $R^{18}$ is substituted or unsubstituted aryl. In certain embodiments, one of $R^9$, $R^{10}$, $R^{11}$, $R^{12}$, $R^{13}$, $R^{14}$, $R^{15}$, $R^{16}$, $R^{17}$, and $R^{18}$ is substituted or unsubstituted heteroaryl.

Variable Y

Palladium complexes of Formula (C) and (E) are typically electrically neutral compounds and include two anionic counterions Y to counterbalance the positive charge on the palladium compounds. In certain embodiments, Y is a non-coordinating anionic counterion or Y is a non-coordinating alkenyl or alkynyl moiety. In certain embodiments, Y is a monovalent anionic counterion. In certain embodiments, Y is ClO$_4^-$, OTf$^-$, BF$_4^-$, PF$_4^-$, PF$_6^-$, or SbF$_6^-$. In certain embodiments, Y is BF$_4^-$ or OTf$^-$. In certain embodiments, Y is BF$_4^-$. In certain embodiments, Y is OTf$^-$. In certain embodiments. Y is B[3,5-(CF$_3$)$_2$C$_6$H$_3$]$_4^-$, BPh$_4^-$, Al(OC(CF$_3$)$_3$)$_4^-$, or a carborane anion (e.g., CB$_{11}$H$_{12}^-$ or ($HCB_{11}Me_5Br_6$)$^-$). In certain embodiments, Y is a non-coordinating alkenyl or alkynyl moiety. In certain embodiments, Y is substituted or unsubstituted acetylene. In certain embodiments, Y is substituted or unsubstituted ethylene.

Fluorinating Agents

A variety of fluorinating agents can be used in the methods described herein. In certain embodiments, the fluorinating agent is an N-fluorinated amine or N-fluorinated quaternary amine salt. In certain embodiments, the fluorinating agent is 1-(chloromethyl)-4-fluoro-1,4-diazoniabicyclo[2.2.2]octane bis(tetrafluoroborate) (F-TEDA-BF$_4$/Selectfluor®). In certain embodiments, the fluorinating agent is N-fluorobenzenesulfonimide (NFBS). In certain embodiments, the fluorinating agent is 1-fluoro-4-methyl-1,4-diazoniabicyclo[2.2.2]octane bis(tetrafluoroborate), N-fluoro-N'-methyl-triethylenediamine bis(tetrafluoroborate), N-fluoro-o-benzenedisulfonimide (NFOBS), N-fluorobenzenesulfonimide (NFSI or NFBS), 1-fluoro-4-hydroxy-1,4-diazoniabicyclo[2,2,2]octane bis(tetrafluoroborate) (NFTh), N-fluoropyridinium pyridine heptafluorodiborate (NFPy), N-fluoropyridinium trifluoromethanesulfonate, N-fluoro-2,4,6-trimethylpyridinium trifluoromethanesulfonate, N-fluoro-2,4,6-trimethylpyridinium tetrafluoroborate, or 2,6-dichloro-1-fluoropyridinium trifluoromethanesulfonate. In certain embodiments, the fluorinating agent is F-TEDA-BF4 or NFBS.

In certain embodiments, the fluorinating agent comprises a fluorine isotope. A compound of Formula (I), (II), or (III) may be enriched with a particular isotope of fluorine, such as $^{18}$F. e.g. e.g. $^{18}$F-fluorinated organic compounds are particularly useful for imaging technology, such as positron-emission tomography (PET) imaging. PET is a noninvasive imaging technology that is currently used in the clinic to image cancers and neurological disorders at an early stage of illness. PET tracers are molecules which incorporate a PET-active nucleus and can therefore be visualized by their positron emission in the body. The fluorine isotope $^{18}$F is the most common nucleus for PET imaging because of its superior properties to other nuclei. The $^{18}$F isotope is radioactive and has a half-life of about 109.77 minutes. The short half-life dictates restrictions on chemical synthesis of PET tracers, because introduction of the fluorine atom has to take place at a very late stage of the synthesis to avoid the unproductive decay of $^{18}$F before it is injected into the body. Fluoride ion is the most common reagent to introduce $^{18}$F but the specific chemical properties of the fluoride ion currently limit the available pool of PET tracers. Due to the narrow functional group compatibility of the strongly basic fluoride ion, only a limited set of chemical reactions can be employed for fluorination, and hence the synthesis of PET tracers is limited to fairly simple molecules. The field of PET imaging would benefit from the availability of a new method that is capable of introducing radiolabeled fluoride into structurally more complex organic molecules. An easy access to drug-based PET tracers would simplify determining the fate of such drugs in the body and thereby help to identify and understand their mode of action, bioavailability, and time-dependent biodistribution.

The described methods are useful in preparing aryl and heteroaryl compounds labeled with $^{18}$F. In certain embodiments, one or more fluorine atoms of a compound of Formula (I), (II), or (III) are enriched with $^{18}$F, e.g., for example, the compound of Formula (I), (II), or (III) encompass compounds of Formula (I*), (II*), or (III*):

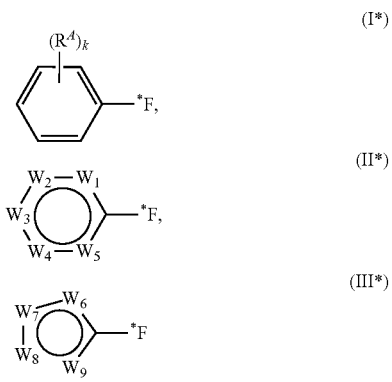

wherein the fluorine atom marked with an asterix (*) is enriched with $^{18}$F.

In certain embodiments, the compound of Formula (I*), (II*), or (III*) is at least 0.01%, at least 0.03%, at least 0.1%, at least 0.3%, or at least 1% mole:mole enriched with $^{18}$F, or the specific activity of the fluorine in a compound of Formula (I*), (II*), or (III*) is at least 0.01, at least 0.03, at least 0.1, at least 0.3, at least 1, at least 3, or at least 10 Ci/µmol. An aryl substrate (e.g., a compound of Formula (D)) or heteroaryl substrated (e.g., a compound of Formula (E) or (F)) may be labeled with $^{18}$F using a fluorinating agent that is enriched with $^{18}$F. In certain embodiments, the fluorinating agent is enriched with $^{18}$F, e.g., at least 0.01%, at least 0.03%, at least 0.1%, at least 0.3%, or at least 1% mole:mole of the fluorine in a fluorinating agent is $^{18}$F, or the specific activity of the fluorine in a compound of Formula (I*), (II*), or (III*) is at least 0.01, at least 0.03, at least 0.1, at least 0.3, at least 1, at least 3, or at least 10 Ci/µmol. In certain embodiments, the fluorinating agent is an N-*fluorinated amine or N-*fluorinated quaternary amine salt, wherein the fluorine atom marked with an asterix (*) is enriched with $^{18}$F. In certain embodiments, the fluorinating agent is 1-(chloromethyl)-4-*fluoro-1,4-diazoniabicyclo[2.2.2]octane bis(tetrafluoroborate), wherein the fluorine atom marked with * is enriched with $^{18}$F. In certain embodiments, the fluorinating agent is 1-*fluoro-4-methyl-1,4-diazoniabicyclo[2.2.2]octane bis(tetrafluoroborate), N-*fluoro-N'-methyl-triethylenediamine bis(tetrafluoroborate), N-*fluoro-o-benzenedisulfonimide, N-*fluorobenzenesulfonimide, 1-*fluoro-4-hydroxy-1,4-diazoniabicyclo[2,2,2]octane bis(tetrafluoroborate), N-*fluoropyridinium pyridine heptafluorodiborate, N-*fluoropyridinium trifluoromethanesulfonate, N-*fluoro-2,4,6-trimethylpyridinium trifluoromethanesulfonate, N-*fluoro-2,4,6-trimethylpyridinium tetrafluoroborate, or 2,6-dichloro-1-*fluoropyridinium trifluoromethanesulfonate, wherein each one of the fluorine atom marked with an asterix (*) is enriched with $^{18}$F.

Aromatic Substrates and Variables $R^A$, k, and $W_1$ to $W_9$

A variety of aryl and heteroaryl substrates, e.g., (D), (E), and (F), can be fluorinated using the methods and palladium complexes described herein, to provide fluorinated compounds (I), (II), and (III).

The methods provided herein do not require directing groups on the substrate for C—H fluorination. In certain embodiments, the aryl and heteroaryl substrate is electron rich. Non-limiting examples of an electron rich aryl substrate is the substrate for compounds 3aa and 3ab in the Examples. In certain embodiments, the aryl and heteroaryl substrate is electron neutral. Non-limiting examples of an electron neutral aryl substrate is the substrate for compound 3fa and 3fb in the Examples. In certain embodiments, the aryl and heteroaryl substrate is electron deficient. Non-limiting examples of an electron deficient aryl substrate is the substrate for compounds 3ba, 3bb, 3ca, 3cb, 3da, 3db, 3ea, 3eb in the Examples. In certain embodiments, the aryl or heteroaryl substrate comprises one aryl ring such as the substrate for compounds 3b and 3c. In certain embodiments, the aryl or heteroaryl substrate comprise an aryl ring (e.g., phenyl) substituted with one or more aryl groups (e.g., phenyl), heteroaryl groups (e.g., pyrimidine, pyridinyl), cyclic groups (e.g., cyclohexyl, cyclohexanone), or alkyl substituted with heterocyclic groups (e.g., the substrate for compounds 3na and 3nb).

In certain embodiments, heteroaryl substituents on the aryl substrate are tolerated as stable spectators for the fluorination of more activated aryl C—H bonds on the aryl substrate (e.g., see substrates for compounds 3g, 3i, 3j, 3n).

In certain embodiments, for substrates with multiple aryl or heteroaryl rings, the more electron rich aryl or heteroaryl ring is preferentially fluorinated, albeit with low regioselectivity between electronically similar positions (e.g., see substrates for compounds 3d, 3e, 3g, 3i, 3j).

In certain embodiments, many types of functional groups are compatible with the reactions conditions, including esters (e.g., see substrate for compounds 3h, 3k, 3o), amides (e.g., see substrates for compounds 3k, 3n, 3o), fully-substituted sulfonamides (e.g., see substrate for compound 3g), carbamates (s e.g., ee substrate for compound 3n), aryl bromides (e.g., see substrate for compound 3b) and chlorides (e.g., see substrate for compound 3c), alkyl bromides (e.g., see substrate for compound 3f), alcohols (e.g., see substrate for compound 3l), ketones (e.g., see substrates for compounds 3g, 3n) and nitriles (e.g., see substrates for compound 3d).

In certain embodiments, the aryl or heteroaryl substrate does not comprise fluorine atoms, and only a single fluorine is inserted from the reaction, to provide a fluorinated product with one fluorine atom. In certain embodiments, the aryl or heteroaryl substrate comprises 1, 2, 3, or 4 fluorine atoms, and only a single fluorine is inserted from the reaction to provide the fluorinated product comprising 2, 3, 4, or 5 fluorine atoms, respectively.

In certain embodiments, the fluorine is added to a mono-substituted aryl or heteroaryl ring ortho to the point of substitution. In certain embodiments, the fluorine is added to a monosubstituted aryl or heteroaryl ring para to the point of substitution. In certain embodiments, the fluorine is added to a monosubstituted aryl or heteroaryl meta to the point of substitution.

In certain embodiments, the fluorine is added to a di or tri substituted aryl or heteroaryl ring at a more sterically hindered position on the substrate, e.g., at a position on the substrate which is adjacent to (on either side of) two non-hydrogen groups. In certain embodiments, the fluorine is added to a di or tri substituted aryl or heteroaryl ring at a less sterically hindered position on the substrate, e.g., at a position on the substrate which is not adjacent to (on either side of) non-hydrogen groups.

As generally defined herein, $W_1$, $W_2$, $W_3$, $W_4$, and $W_5$ (of compounds of Formula (E) and (II)) is CH, $CR^A$, or N, provided at least one of $W_1$, $W_2$, $W_3$, $W_4$, and $W_5$ is N. In certain embodiments, $W_1$ is N and the remainder of the W groups are CH or $CR^A$. In certain embodiments, $W_2$ is N and the remainder of the W groups are CH or $CR^A$. In certain embodiments, $W_3$ is N and the remainder of the W groups are CH or $CR^A$. In certain embodiments, $W_1$ and $W_2$ are each N and the remainder of the W groups are CH or $CR^A$. In certain embodiments, $W_2$ and $W_3$ are each N and the remainder of the W groups are CH or $CR^A$. In certain embodiments, $W_2$ and $W_4$ are each N and the remainder of the W groups are CH or $CR^A$. In certain embodiments, $W_1$ and $W_3$ are each N and the remainder of the W groups are CH or $CR^A$. In certain embodiments, $W_1$ and $W_4$ are each N and the remainder of the W groups are CH or $CR^A$. In certain embodiments, $W_1$ and $W_5$ are each N and the remainder of the W groups are CH or $CR^A$. In certain embodiments, $W_1$, $W_3$, and $W_5$ are each N and the remainder of the W groups are CH or $CR^A$. In certain embodiments, $W_1$, $W_2$, and $W_4$ are each N and the remainder of the W groups are CH or $CR^A$. In certain embodiments, $W_1$, $W_2$, and $W_5$ are each N and the remainder of the W groups are CH or $CR^A$. In certain embodiments, $W_1$, $W_2$, $W_4$, and $W_5$ are each N and $W_3$ is CH or $CR^A$.

As generally defined herein, $W_6$, $W_7$, $W_8$, and $W_9$ (of compounds of Formula (F) and (III)) is CH, $CR^A$, N, NH, $NR^A$, O, or S, provided at least one of $W_6$, $W_7$, $W_8$, and $W_9$ is N, NH, $NR^A$, O, or S. In certain embodiments, $W_6$ is $NR^A$, O, or S, and the remainder of the W groups are CH or $CR^A$. In certain embodiments, $W_7$ is $NR^A$, O, or S, and the remainder of the W groups are CH or $CR^A$. In certain embodiments, $W_6$ is N, $W_7$ is $NR^A$, O, or S, and the remainder of the W groups are CH or $CR^A$. In certain embodiments, $W_7$ is N, $W_6$ is $NR^A$, O, or S, and the remainder of the W groups are CH or $CR^A$. In certain embodiments, $W_6$ is N, $W_8$ is $NR^A$, O, or S, and the remainder of the W groups are CH or $CR^A$. In certain embodiments, $W_8$ is N, $W_6$ is $NR^A$, O, or S, and the remainder of the W groups are CH or $CR^A$.

As generally defined herein, each instance of $R^A$ is independently halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —CN, —SCN, —C(=$NR^{A1}$)$R^{A1}$, —C(=$NR^{A1}$)$OR^{A1}$, —C(=$NR^{A1}$)N($R^{A1}$)$_2$, —C(=O)$R^{A1}$, —C(=O)$OR^{A1}$, —C(=O)N($R^{A1}$)$_2$, —NO$_2$, —$NR^{A1}$C(=O)$R^{A1}$, —$NR^{A1}$C(=O)$OR^{A1}$, —$NR^{A1}$C(=O)N($R^{A1}$)$_2$, —OC(=O)$R^{A1}$, —OC(=O)$OR^{A1}$, or —OC(=O)N($R^{A1}$)$_2$, or two vicinal $R^A$ groups (groups attached to two adjacent carbon atoms) are joined to form a substituted or unsubstituted carbocyclyl, substituted or unsubstituted heterocyclyl, substituted or unsubstituted aryl, or substituted or unsubstituted heteroaryl ring; and each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1}$ attached the same nitrogen atom are joined to form a substituted or unsubstituted heterocyclic or substituted or unsubstituted heteroaryl ring.

In certain embodiments, the aryl or heteroaryl substrate is not electron deficient (e.g., such as methyl benzoate

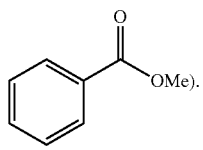

In certain embodiments, $R^A$ is not a reactive functional group, such as tertiary amines or carboxylic acids. For example, $R^A$ is not —C(=O)OH or —N($R^Z$)$_3^+$, wherein each instance of $R^Z$ is independently acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. In certain embodiments, $R^A$ is not a benzylic heteroatom (e.g., a benzylic amide). For example, the aryl or heteroaryl substrate is not ArCH$_2$N($R^{Z1}$)$_2$, ArCH$_2$OR$^{Z2}$, or ArCH$_2$SR$^{Z2}$, wherein Ar is aryl or heteroaryl, and each instance of $R^{Z1}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl; and wherein each instance of $R^{Z2}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl.

In certain embodiments, compounds of Formula (I), (II), (III), (D), (E), or (F) are unsubstituted, wherein k is 0 or wherein the non-hydrogen group $R^A$ is not present. For example, In certain embodiments, compounds of Formula (I), (II), (III), (D), (E), or (F) include one to five substituents $R^A$, as valency permits.

In certain embodiments, at least one instance of $R^A$ is halogen. In certain embodiments, at least one instance of $R^A$ is F. In certain embodiments, at least one instance of $R^A$ is Cl. In certain embodiments, at least one instance of $R^A$ is Br. In certain embodiments, at least one instance of $R^A$ is I (iodine).

In certain embodiments, at least one instance of $R^A$ is acyl.

In certain embodiments, at least one instance of $R^A$ is substituted alkyl. In certain embodiments, at least one instance of $R^A$ is unsubstituted alkyl. In certain embodiments, at least one instance of $R^A$ is $C_{1-12}$ alkyl. In certain embodiments, at least one instance of $R^A$ is substituted $C_{1-6}$ alkyl. In certain embodiments, at least one instance of $R^A$ is unsubstituted $C_{1-6}$ alkyl. In certain embodiments, at least one instance of $R^A$ is substituted methyl. In certain embodiments, at least one instance of $R^A$ is —CH$_2$F. In certain embodiments, at least one instance of $R^A$ is —CHF$_2$. In certain embodiments, at least one instance of $R^A$ is —CF$_3$. In certain embodiments, at least one instance of $R^A$ is Bn. In certain embodiments, at least one instance of $R^A$ is —(CH$_2$)$_3$OH, —CH$_2$CO$_2$H, —CH$_2$CO$_2$Me, or

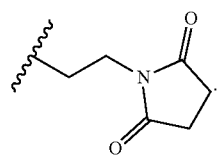 [SMILES: *CCN1C(=O)CCC1=O]

In certain embodiments, at least one instance of $R^A$ is unsubstituted methyl. In certain embodiments, at least one instance of $R^A$ is ethyl. In certain embodiments, at least one instance of $R^A$ is propyl. In certain embodiments, at least one instance of $R^A$ is i-propyl. In certain embodiments, at least one instance of $R^A$ is butyl. In certain embodiments, at least one instance of $R^A$ is t-butyl. In certain embodiments, at least one instance of $R^A$ is pentyl. In certain embodiments, at least one instance of $R^A$ is hexyl.

In certain embodiments, at least one instance of $R^A$ is substituted alkenyl. In certain embodiments, at least one instance of $R^A$ is unsubstituted alkenyl. In certain embodiments, at least one instance of $R^A$ is substituted or unsubstituted $C_{1-6}$ alkenyl. In certain embodiments, at least one instance of $R^A$ is vinyl. In certain embodiments, at least one instance of $R^A$ is of the formula:

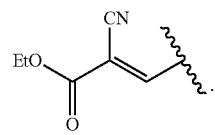 [SMILES: */C=C(\C#N)C(=O)OCC]

In certain embodiments, at least one instance of $R^A$ is substituted alkynyl. In certain embodiments, at least one instance of $R^A$ is unsubstituted alkynyl. In certain embodiments, at least one instance of $R^A$ is ethynyl.

In certain embodiments, at least one instance of $R^A$ is substituted carbocyclyl. In certain embodiments, at least one instance of $R^A$ is unsubstituted carbocyclyl. In certain embodiments, at least one instance of $R^A$ is saturated carbocyclyl. In certain embodiments, at least one instance of $R^A$ is unsaturated carbocyclyl. In certain embodiments, at least one instance of $R^A$ is carbocyclyl including zero, one, two, or three double bonds in the carbocyclic ring system. In certain embodiments, at least one instance of $R^A$ is monocyclic carbocyclyl. In certain embodiments, at least one instance of $R^A$ is 3- to 7-membered, monocyclic carbocyclyl. In certain embodiments, at least one instance of $R^A$ is cyclopropyl. In certain embodiments, at least one instance of $R^A$ is cyclobutyl. In certain embodiments, at least one instance of $R^A$ is cyclopentyl. In certain embodiments, at least one instance of $R^A$ is cyclohexyl. In certain embodiments, at least one instance of $R^A$ is cycloheptyl. In certain embodiments, at least one instance of $R^A$ is bicyclic carbocyclyl. In certain embodiments, at least one instance of $R^A$ is 5- to 13-membered, bicyclic carbocyclyl.

In certain embodiments, at least one instance of $R^A$ is substituted heterocyclyl. In certain embodiments, at least one instance of $R^A$ is unsubstituted heterocyclyl. In certain embodiments, at least one instance of $R^A$ is saturated heterocyclyl. In certain embodiments, at least one instance of $R^A$ is unsaturated heterocyclyl. In certain embodiments, at least one instance of $R^A$ is heterocyclyl including zero, one, two, or three double bonds in the heterocyclic ring system. In certain embodiments, at least one instance of $R^A$ is heterocyclyl, wherein one, two, or three atoms in the heterocyclic ring system are independently selected from the group consisting of nitrogen, oxygen, and sulfur. In certain embodiments, at least one instance of $R^A$ is monocyclic heterocyclyl. In certain embodiments, at least one instance of $R^A$ is 3- to 7-membered, monocyclic heterocyclyl. In certain embodiments, at least one instance of $R^A$ is bicyclic heterocyclyl. In certain embodiments, at least one instance of $R^A$ is 5- to 13-membered, bicyclic heterocyclyl.

In certain embodiments, at least one instance of $R^A$ is substituted aryl. In certain embodiments, at least one instance of $R^A$ is unsubstituted aryl. In certain embodiments, at least one instance of $R^A$ is 6- to 14-membered aryl. In certain embodiments, at least one instance of $R^A$ is 6- to 10-membered aryl. In certain embodiments, at least one instance of $R^A$ is substituted phenyl. In certain embodiments, at least one instance of $R^A$ is unsubstituted phenyl. In certain embodiments, at least one instance of $R^A$ is substituted naphthyl. In certain embodiments, at least one instance of $R^A$ is unsubstituted naphthyl.

In certain embodiments, at least one instance of $R^A$ is substituted heteroaryl. In certain embodiments, at least one instance of $R^A$ is unsubstituted heteroaryl. In certain embodiments, at least one instance of $R^A$ is heteroaryl, wherein one, two, three, or four atoms in the heteroaryl ring system are independently selected from the group consisting of nitrogen, oxygen, and sulfur. In certain embodiments, at least one instance of $R^A$ is monocyclic heteroaryl. In certain embodiments, at least one instance of $R^A$ is 5-membered, monocyclic heteroaryl. In certain embodiments, at least one instance of $R^A$ is 6-membered, monocyclic heteroaryl. In certain embodiments, at least one instance of $R^A$ is substituted pyridyl. In certain embodiments, at least one instance of $R^A$ is unsubstituted 2-pyridyl, unsubstituted 3-pyridyl, or unsubstituted 4-pyridyl. In certain embodiments, at least one instance of $R^A$ is bicyclic heteroaryl, wherein the point of attachment may be on any atom of the bicyclic heteroaryl ring system, as valency permits. In certain embodiments, at least one instance of $R^A$ is 9-membered, bicyclic heteroaryl. In certain embodiments, at least one instance of $R^A$ is 10-membered, bicyclic heteroaryl.

In certain embodiments, at least one instance of $R^A$ is —$OR^{A1}$. In certain embodiments, at least one instance of $R^A$ is —OMe. In certain embodiments, at least one instance of $R^A$ is —OEt. In certain embodiments, at least one instance of $R^A$ is —OPr. In certain embodiments, at least one instance of $R^A$ is —OBu. In certain embodiments, at least one instance of $R^A$ is —O(pentyl). In certain embodiments, at least one instance of $R^A$ is —O(hexyl). In certain embodiments, at least one instance of $R^A$ is —OBn. In certain embodiments, at least one instance of $R^A$ is —$OR^{A1}$, wherein $R^{A1}$ is acyl or substituted or unsubstituted aryl. In certain embodiments, at least one instance of $R^A$ is —O(Boc). In certain embodiments, at least one instance of $R^A$ is —OPh. In certain embodiments, at least one instance of $R^A$ is —OH.

In certain embodiments, at least one instance of $R^A$ is —$SR^{A1}$. In certain embodiments, at least one instance of $R^A$ is —SMe. In certain embodiments, at least one instance of $R^A$ is —SH. In certain embodiments, no instance of $R^A$ is —$SR^{A1}$.

In certain embodiments, at least one instance of $R^A$ is —$N(R^{A1})_2$. In certain embodiments, at least one instance of $R^A$ is —$NMe_2$. In certain embodiments, at least one instance of $R^A$ is —$NH_2$.

In certain embodiments, at least one instance of $R^A$ is —CN. In certain embodiments, at least one instance of $R^A$ is —SCN.

In certain embodiments, at least one instance of $R^A$ is —$C(=NR^{A1})R^{A1}$, —$C(=NR^{A1})OR^{A1}$, or —$C(=NR^{A1})N(R^{A1})_2$.

In certain embodiments, at least one instance of $R^A$ is —$C(=O)R^{A1}$ or —$C(=O)OR^{A1}$. In certain embodiments, at least one instance of $R^A$ is —$C(=O)N(R^{A1})_2$. In certain embodiments, at least one instance of $R^A$ is —$C(=O)N(R^{A1})_2$, wherein each instance of $R^{A1}$ is independently selected from the group consisting of hydrogen, substituted or unsubstituted alkyl, or a nitrogen protecting group. In certain embodiments, at least one instance of $R^A$ is —$C(=O)N(R^{A1})_2$, wherein each instance of $R^{A1}$ is independently selected from the group consisting of hydrogen, unsubstituted $C_{1-6}$ alkyl, Bn, Boc, Cbz, Fmoc, trifluoroacetyl, triphenylmethyl, acetyl, or Ts. In certain embodiments, at least one instance of $R^A$ is —$C(=O)NH_2$.

In certain embodiments, at least one instance of $R^A$ is —$NO_2$.

In certain embodiments, at least one instance of $R^A$ is —$NR^{A1}C(=O)R^{A1}$, —$NR^{A1}C(=O)OR^{A1}$, or —$NR^{A1}C(=O)N(R^{A1})_2$.

In certain embodiments, at least one instance of $R^A$ is —$OC(=O)R^{A1}$, —$OC(=O)OR^{A1}$, or —$OC(=O)N(R^{A1})_2$.

In certain embodiments, at least one instance of $R^A$ is halogen or substituted or unsubstituted alkyl. In certain embodiments, at least one instance of $R^A$ is halogen or unsubstituted alkyl. In certain embodiments, at least one instance of $R^A$ is halogen or unsubstituted $C_{1-6}$ alkyl.

In certain embodiments, two vicinal $R^A$ groups (groups attached to two adjacent carbon atoms) are joined to form a substituted or unsubstituted carbocyclyl.

In certain embodiments, two vicinal $R^A$ groups (groups attached to two adjacent carbon atoms) are joined to form a substituted or unsubstituted heterocyclyl.

In certain embodiments, two vicinal $R^A$ groups (groups attached to two adjacent carbon atoms) are joined to form a substituted or unsubstituted aryl.

In certain embodiments, two vicinal $R^A$ groups (groups attached to two adjacent carbon atoms) are joined to form a substituted or unsubstituted heteroaryl.

In certain embodiments, at least one instance of $R^{A1}$ is hydrogen.

In certain embodiments, at least one instance of $R^{A1}$ is acyl (e.g., acetyl, —$C(=O)CH_3$).

In certain embodiments, at least one instance of $R^{A1}$ is substituted alkyl. In certain embodiments, at least one instance of $R^{A1}$ is unsubstituted alkyl. In certain embodiments, at least one instance of $R^{A1}$ is $C_{1-12}$ alkyl. In certain embodiments, at least one instance of $R^{A1}$ is $C_{1-6}$ alkyl. In certain embodiments, at least one instance of $R^{A1}$ is methyl. In certain embodiments, at least one instance of $R^{A1}$ is ethyl. In certain embodiments, at least one instance of $R^{A1}$ is propyl. In certain embodiments, at least one instance of $R^{A1}$ is butyl. In certain embodiments, at least one instance of $R^{A1}$ is pentyl. In certain embodiments, at least one instance of $R^{A1}$ is hexyl.

In certain embodiments, at least one instance of $R^{A1}$ is substituted alkenyl. In certain embodiments, at least one instance of $R^{A1}$ is unsubstituted alkenyl. In certain embodiments, at least one instance of $R^{A1}$ is vinyl.

In certain embodiments, at least one instance of $R^{A1}$ is substituted alkynyl. In certain embodiments, at least one instance of $R^{A1}$ is unsubstituted alkynyl. In certain embodiments, at least one instance of $R^{A1}$ is ethynyl.

In certain embodiments, at least one instance of $R^{A1}$ is substituted carbocyclyl. In certain embodiments, at least one instance of $R^{A1}$ is unsubstituted carbocyclyl. In certain embodiments, at least one instance of $R^{A1}$ is saturated carbocyclyl. In certain embodiments, at least one instance of $R^{A1}$ is unsaturated carbocyclyl. In certain embodiments, at least one instance of $R^{A1}$ is carbocyclyl including zero, one, two, or three double bonds in the carbocyclic ring system. In certain embodiments, at least one instance of $R^{A1}$ is 3- to 7-membered, monocyclic carbocyclyl. In certain embodiments, at least one instance of $R^{A1}$ is cyclopropyl. In certain embodiments, at least one instance of $R^{41}$ is cyclobutyl. In certain embodiments, at least one instance of $R^{41}$ is cyclopentyl. In certain embodiments, at least one instance of $R^{41}$ is cyclohexyl. In certain embodiments, at least one instance of $R^{41}$ is cycloheptyl. In certain embodiments, at least one instance of $R^{41}$ is 5- to 13-membered, bicyclic carbocyclyl.

In certain embodiments, at least one instance of $R^{41}$ is substituted heterocyclyl. In certain embodiments, at least one instance of $R^{41}$ is unsubstituted heterocyclyl. In certain embodiments, at least one instance of $R^{41}$ is saturated heterocyclyl. In certain embodiments, at least one instance of $R^{41}$ is unsaturated heterocyclyl. In certain embodiments, at least one instance of $R^{41}$ is heterocyclyl including zero, one, two, or three double bonds in the heterocyclic ring system. In certain embodiments, at least one instance of $R^{41}$ is heterocyclyl, wherein one, two, or three atoms in the heterocyclic ring system are independently selected from the group consisting of nitrogen, oxygen, and sulfur. In certain embodiments, at least one instance of $R^{41}$ is 3- to 7-membered, monocyclic heterocyclyl. In certain embodiments, at least one instance of $R^{41}$ is 5- to 13-membered, bicyclic heterocyclyl.

In certain embodiments, at least one instance of $R^{41}$ is substituted or unsubstituted aryl. In certain embodiments, at least one instance of $R^{41}$ is 6- to 14-membered aryl. In certain embodiments, at least one instance of $R^{41}$ is 6- to 10-membered aryl. In certain embodiments, at least one instance of $R^{41}$ is monocyclic aryl. In certain embodiments, at least one instance of $R^{41}$ is phenyl. In certain embodiments, at least one instance of $R^{41}$ is bicyclic aryl. In certain embodiments, at least one instance of $R^{41}$ is naphthyl.

In certain embodiments, at least one instance of $R^{41}$ is substituted or unsubstituted heteroaryl. In certain embodiments, at least one instance of $R^{41}$ is heteroaryl, wherein one, two, three, or four atoms in the heteroaryl ring system are independently selected from the group consisting of nitrogen, oxygen, and sulfur. In certain embodiments, at least one instance of $R^{41}$ is monocyclic heteroaryl. In certain embodiments, at least one instance of $R^{41}$ is 5-membered, monocyclic heteroaryl. In certain embodiments, at least one instance of $R^{41}$ is 6-membered, monocyclic heteroaryl. In certain embodiments, at least one instance of $R^{41}$ is pyridyl. In certain embodiments, at least one instance of $R^{41}$ is bicyclic heteroaryl, wherein the point of attachment may be on any atom of the bicyclic heteroaryl ring system, as valency permits. In certain embodiments, at least one instance of $R^{41}$ is 9-membered, bicyclic heteroaryl. In certain embodiments, at least one instance of $R^{41}$ is 10-membered, bicyclic heteroaryl.

In certain embodiments, at least one instance of $R^{41}$ is a nitrogen protecting group when attached to a nitrogen atom. In certain embodiments, at least one instance of $R^{41}$ is Bn, Boc, Cbz, Fmoc, trifluoroacetyl, triphenylmethyl, acetyl, or Ts when attached to a nitrogen atom.

In certain embodiments, $R^{41}$ is an oxygen protecting group when attached to an oxygen atom. In certain embodiments, $R^{41}$ is silyl, TBDPS, TBDMS, TIPS, TES, TMS, MOM, THP, t-Bu, Bn, allyl, acetyl, pivaloyl, or benzoyl when attached to an oxygen atom.

In certain embodiments, $R^{41}$ is a sulfur protecting group when attached to a sulfur atom. In certain embodiments, $R^{41}$ is acetamidomethyl, t-Bu, 3-nitro-2-pyridine sulfenyl, 2-pyridine-sulfenyl, or triphenylmethyl when attached to a sulfur atom.

In certain embodiments, two instances of $R^{41}$ on the same nitrogen atom are joined to form a substituted or unsubstituted heterocyclic ring. In certain embodiments, two instances of $R^{41}$ on the same nitrogen atom are joined to form a saturated or unsaturated heterocyclic ring. In certain embodiments, two instances of $R^{41}$ on the same nitrogen atom are joined to form a heterocyclic ring including zero, one, two, or three double bonds in the heterocyclic ring system. In certain embodiments, two instances of $R^{41}$ on the same nitrogen atom are joined to form a heterocyclic ring, wherein one, two, or three atoms in the heterocyclic ring system are independently selected from the group consisting of nitrogen, oxygen, and sulfur. In certain embodiments, two instances of $R^{41}$ on the same nitrogen atom are joined to form a 3- to 7-membered, monocyclic heterocyclic ring. In certain embodiments, two instances of $R^{41}$ on the same nitrogen atom are joined to form a 5- to 13-membered, bicyclic heterocyclic ring.

As generally defined herein, k is 0, 1, 2, 3, 4, or 5. In certain embodiments, k is 0. In certain embodiments, k is 1. In certain embodiments, k is 2. In certain embodiments, k is 3. In certain embodiments, k is 4. In certain embodiments, k is 5.

In certain embodiments, k is 1 and/or one $R^A$ non-hydrogen substituent is present on the aryl or heteroaryl ring selected from the group consisting of halogen, acyl, substituted or unsubstituted alkyl, substituted or unsubstituted alkenyl, substituted or unsubstituted aryl, substituted or unsubstituted heteroaryl, and substituted or unsubstituted carbocyclyl. In certain embodiments, k is 1 and/or one $R^A$ non-hydrogen substituent is present on the aryl or heteroaryl ring selected from the group consisting of halogen, substituted or unsubstituted $C_{1-6}$ alkyl, substituted or unsubstituted $C_{1-6}$ alkenyl, substituted or unsubstituted phenyl, substituted or unsubstituted pyridyl, substituted or unsubstituted pyrimidinyl, and substituted or unsubstituted $C_{1-6}$ carbocyclyl. In certain embodiments, k is 2 and/or two $R^A$ non-hydrogen substituents are present on the aryl or heteroaryl ring selected from the group consisting of substituted or unsubstituted alkyl. In certain embodiments, k is 3 and/or three $R^A$ non-hydrogen substituents are present on the aryl or heteroaryl ring selected from the group consisting of substituted or unsubstituted alkyl. In certain embodiments, k is 3 and/or three $R^A$ non-hydrogen substituents are present on the aryl or heteroaryl ring selected from the group consisting of substituted or unsubstituted $C_{1-6}$ alkyl.

In certain embodiments, k is 1 and/or one $R^A$ non-hydrogen substituent is present on the aryl or heteroaryl ring selected from the group consisting of substituted or unsubstituted $C_{1-3}$ alkyl. In certain embodiments, the alkyl is substituted with —COOR, wherein R is a $C_{1-6}$ alkyl; with —NHR, wherein R is acetyl; with —NHCOR, wherein R is a $C_{1-6}$ alkyl or substituted or unsubstituted carbocyclyl; or with substituted or unsubstituted heterocyclyl. In certain embodiments, the $C_{1-3}$ alkyl is substituted with a halogen. In certain embodiments, k is 1 and/or one $R^A$ non-hydrogen substituent is present on the aryl or heteroaryl ring selected from the group consisting of halogen. In certain embodiments, $R^A$ is Br or Cl. In certain embodiments, k is 1 and/or one $R^A$ non-hydrogen substituent is present on the aryl or heteroaryl ring selected from the group consisting of substituted or unsubstituted phenyl. In certain embodiments, the phenyl is substituted with one or more —CN, —CF_3, —SO_2NR_2, wherein R is joined to form a substituted or unsubstituted carbocyclic, substituted or unsubstituted heterocyclic, substituted or unsubstituted aryl, or substituted or unsubstituted heteroaryl ring. In certain embodiments, k is 1 and/or one $R^A$ non-hydrogen substituent is present on the aryl or heteroaryl ring selected from the group consisting substituted or unsubstituted pyridyl. In certain embodiments, k is 1 and/or one $R^A$ non-hydrogen substituent is present on the aryl or heteroaryl ring selected from the group consisting of substituted or unsubstituted pyrimidinyl. In certain embodiments, k is 1 and/or one $R^A$ non-hydrogen substituent is present on the aryl or heteroaryl ring selected from the group consisting of substituted or unsubstituted cyclohexanone. In certain embodiments, k is 1 and/or one $R^A$ non-hydrogen substituent is present on the aryl or heteroaryl ring selected from the group consisting of substituted or unsubstituted $C_{3-6}$ carbocyclyl. In certain embodiments, the carbocyclyl is substituted with —OR or —COOR, wherein R is a H or $C_{1-6}$ alkyl. In certain embodiments, k is 1 and/or one $R^A$ non-hydrogen substituent is present on the aryl or heteroaryl ring selected from the group consisting of substituted or unsubstituted heterocyclyl (e.g., substituted or unsubstituted bicyclic heterocyclyl, such as nortropinone).

In certain embodiments, a substrate of formula:

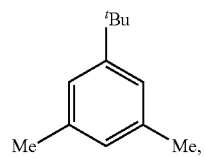

is fluorinated following the procedures and methods described herein to provide a compound of formula:

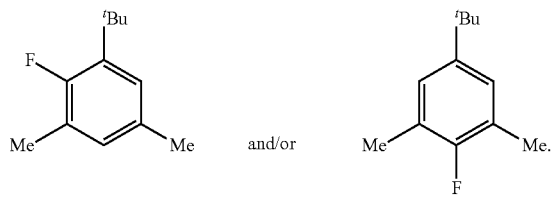 [SMILES: Cc1cc(C)c(F)c(C(C)(C)C)c1 ; Cc1cc(C(C)(C)C)cc(C)c1F]

In certain embodiments, a substrate of formula:

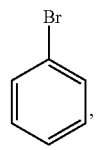

is fluorinated following the procedures and methods described herein to provide a compound of formula:

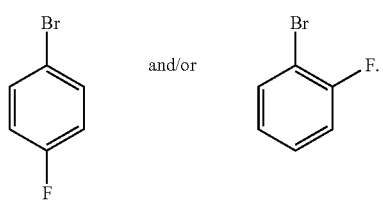 [SMILES: Fc1ccc(Br)cc1 ; Fc1ccccc1Br]

In certain embodiments, a substrate of formula:

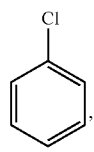

is fluorinated following the procedures and methods described herein to provide a compound of formula:

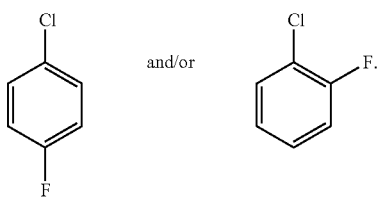 [SMILES: Fc1ccc(Cl)cc1 ; Fc1ccccc1Cl]

In certain embodiments, a substrate of formula:

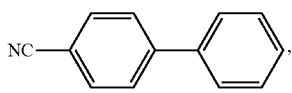

is fluorinated following the procedures and methods described herein to provide a compound of formula:

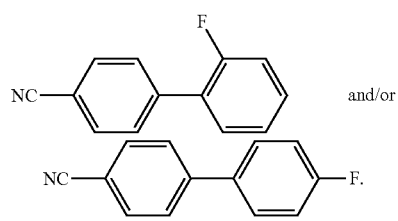

In certain embodiments, a substrate of formula:

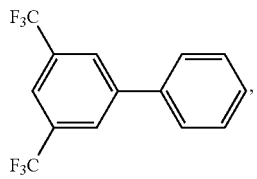

is fluorinated following the procedures and methods described herein to provide a compound of formula:

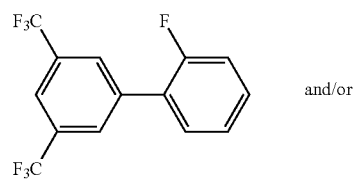

-continued

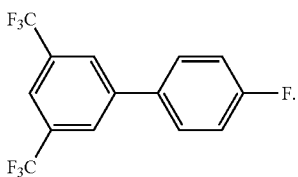

In certain embodiments, a substrate of formula:

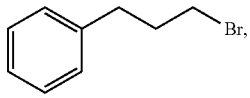

is fluorinated following the procedures and methods described herein to provide a compound of formula:

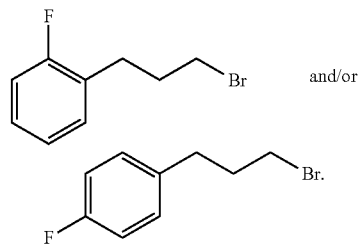

In certain embodiments, a substrate of formula:

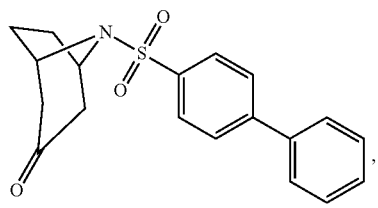 [SMILES: O=C1CC2CCC(C1)N2S(=O)(=O)c1ccc(-c2ccccc2)cc1]

is fluorinated following the procedures and methods described herein to provide a compound of formula:

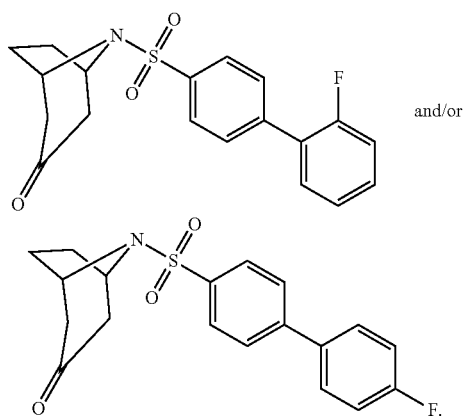

In certain embodiments, a substrate of formula:

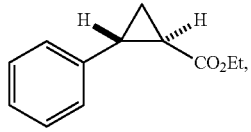 [SMILES: CCOC(=O)[C@@H]1C[C@H]1c1ccccc1]

is fluorinated following the procedures and methods described herein to provide a compound of formula:

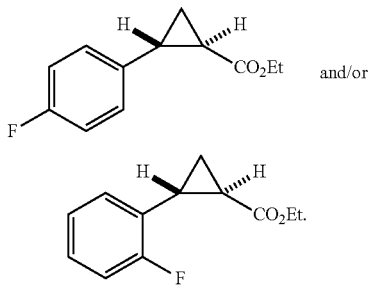

In certain embodiments, a substrate of formula:

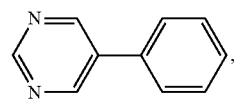

is fluorinated following the procedures and methods described herein to provide a compound of formula:

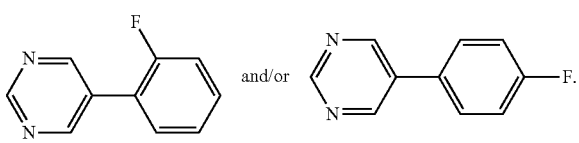 [SMILES: Fc1ccccc1-c1cncnc1 ; Fc1ccc(-c2cncnc2)cc1]

In certain embodiments, a substrate of formula:

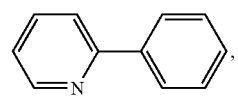

is fluorinated following the procedures and methods described herein to provide a compound of formula:

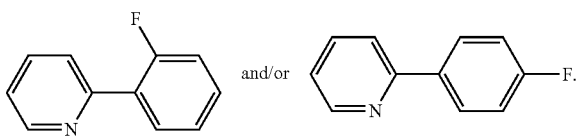 [SMILES: Fc1ccccc1-c1ccccn1 ; Fc1ccc(-c2ccccn2)cc1]

In certain embodiments, a substrate of formula:

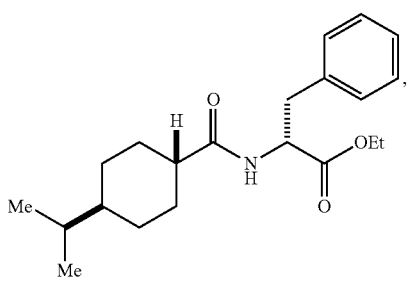 [SMILES: CCOC(=O)[C@@H](Cc1ccccc1)NC(=O)[C@H]1CC[C@H](C(C)C)CC1]

is fluorinated following the procedures and methods described herein to provide a compound of formula:

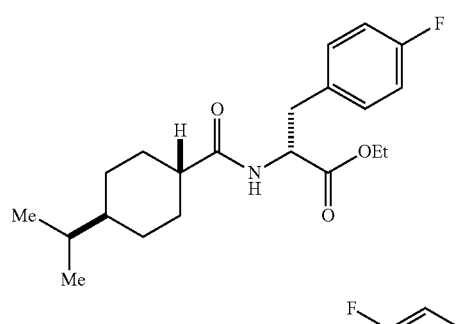
and/or

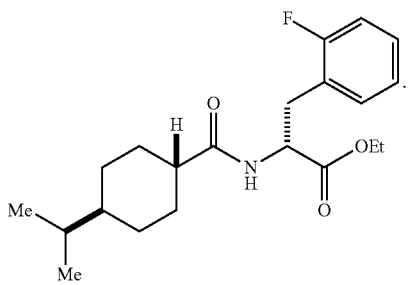

In certain embodiments, a substrate of formula:

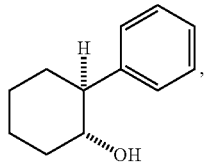 [SMILES: O[C@@H]1CCCC[C@H]1c1ccccc1]

is fluorinated following the procedures and methods described herein to provide a compound of formula:

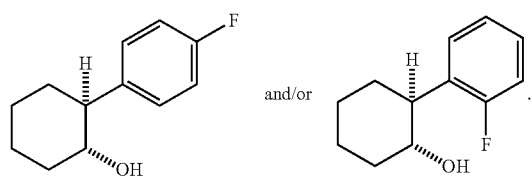 [SMILES: O[C@@H]1CCCC[C@H]1c1ccc(F)cc1 ; O[C@@H]1CCCC[C@H]1c1ccccc1F] and/or 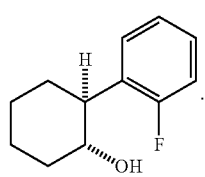

In certain embodiments, a substrate of formula:

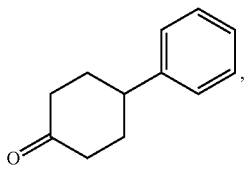 [SMILES: O=C1CCC(c2ccccc2)CC1]

is fluorinated following the procedures and methods described herein to provide a compound of formula:

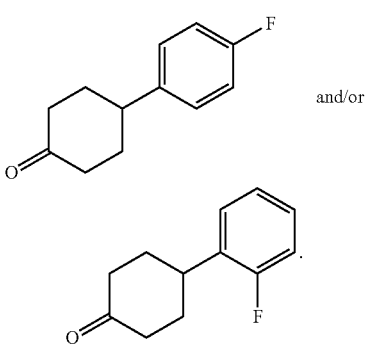 and/or

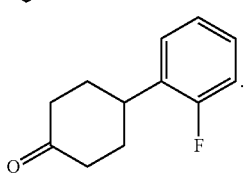

In certain embodiments, a substrate of formula:

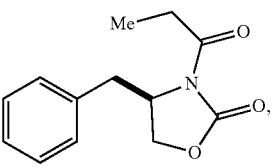

is fluorinated following the procedures and methods described herein to provide a compound of formula:

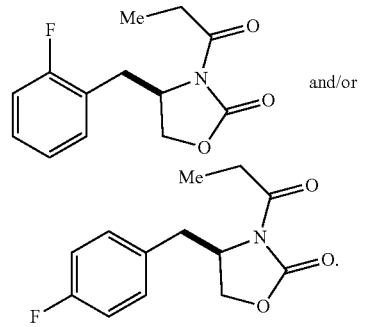

In certain embodiments, a substrate of formula:

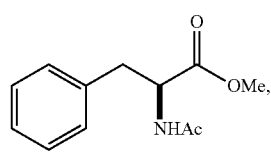 [SMILES: COC(=O)[C@H](Cc1ccccc1)NC(C)=O]

is fluorinated following the procedures and methods described herein to provide a compound of formula:

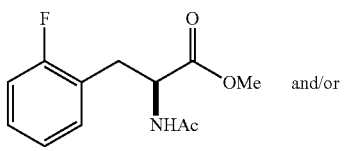

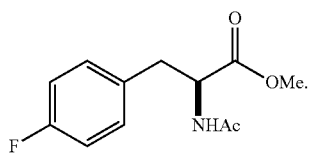

In certain embodiments, a substrate of formula:

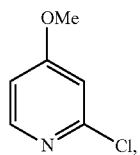

is fluorinated following the procedures and methods described herein to provide a compound of formula:

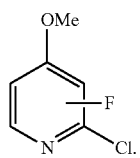

In certain embodiments, a substrate of formula:

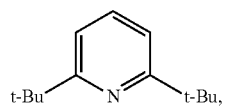

is fluorinated following the procedures and methods described herein to provide a compound of formula:

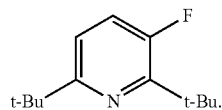

In certain embodiments, a substrate of formula:

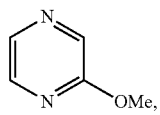

is fluorinated following the procedures and methods described herein to provide a compound of formula:

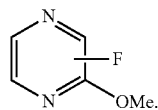

In certain embodiments, a substrate of formula:

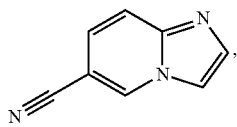 [SMILES: N#Cc1ccc2nccn2c1]

is fluorinated following the procedures and methods described herein to provide a compound of formula:

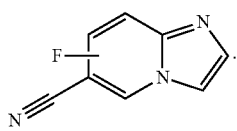

In certain embodiments, a substrate of formula:

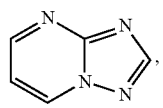

is fluorinated following the procedures and methods described herein to provide a compound of formula:

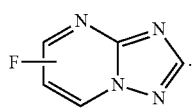

In certain embodiments, a substrate of formula:

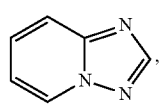

is fluorinated following the procedures and methods described herein to provide a compound of formula:

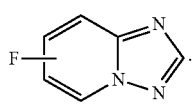

In certain embodiments, a substrate of formula:

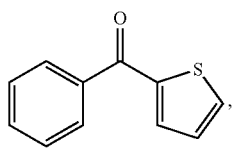 [SMILES: O=C(c1ccccc1)c1cccs1]

is fluorinated following the procedures and methods described herein to provide a compound of formula:

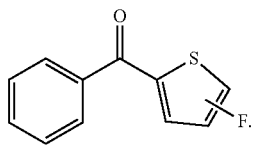

In certain embodiments, a substrate of formula:

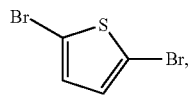

is fluorinated following the procedures and methods described herein to provide a compound of formula:

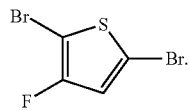

In certain embodiments, a substrate of formula:

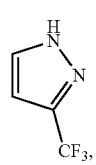

is fluorinated following the procedures and methods described herein to provide a compound of formula:

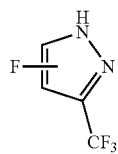

In certain embodiments, a substrate of formula:

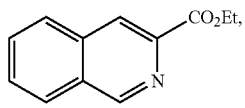 [SMILES: CCOC(=O)c1cc2ccccc2cn1]

is fluorinated following the procedures and methods described herein to provide a compound of formula:

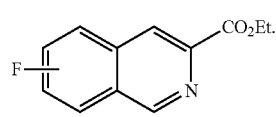

In certain embodiments, a substrate of formula:

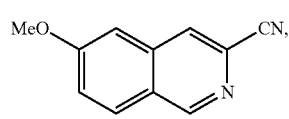

is fluorinated following the procedures and methods described herein to provide a compound of formula:

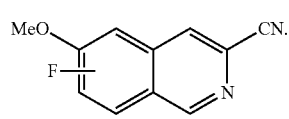

In certain embodiments, a substrate of formula:

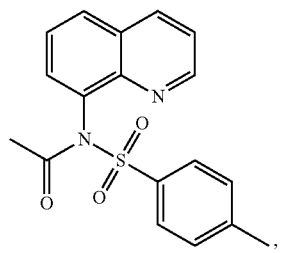 [SMILES: CC(=O)N(c1cccc2cccnc12)S(=O)(=O)c1ccc(C)cc1]

is fluorinated following the procedures and methods described herein to provide a compound of formula:

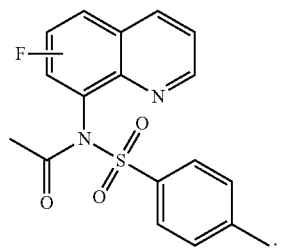

In certain embodiments, a substrate of formula:

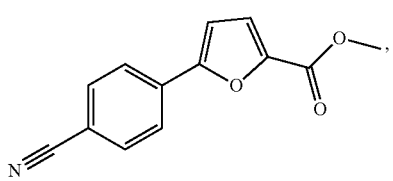 [SMILES: COC(=O)c1ccc(-c2ccc(C#N)cc2)o1]

is fluorinated following the procedures and methods described herein to provide a compound of formula:

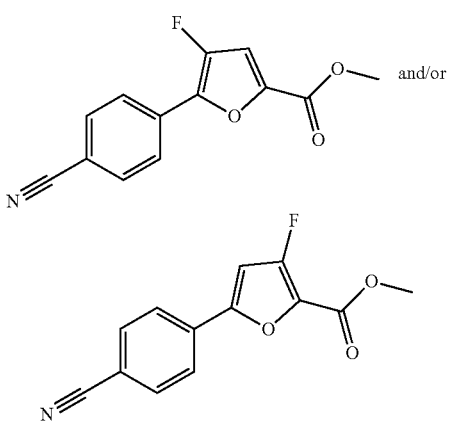

and/or

In certain embodiments, a substrate of formula:

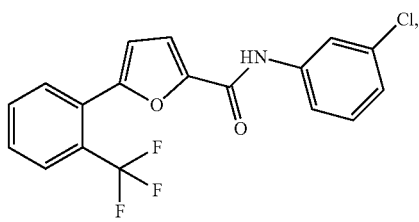 [SMILES: O=C(Nc1cccc(Cl)c1)c1ccc(-c2ccccc2C(F)(F)F)o1]

is fluorinated following the procedures and methods described herein to provide a compound of formula:

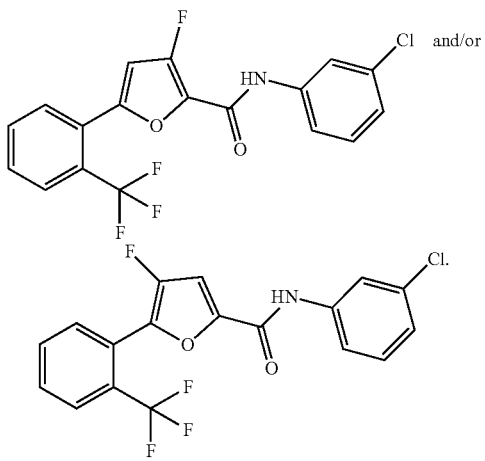

Kits

Provided herein are kits (e.g., packs). In certain embodiments, the kits are useful for preparing the fluorinated compounds described herein (e.g., aryl fluorides fluorides). In certain embodiments, the kits are useful for preparing compounds of Formula (I), (II), or (III).

In certain embodiments, a kit of the invention includes a palladium(II) complex of Formula (C); and optionally a fluorinating agent described herein. In certain embodiments, a kit of the invention includes a palladium(II) complex of Formula (C-1); and optionally a fluorinating agent described herein. In certain embodiments, a kit of the invention includes a palladium(III) complex of Formula (G); and a fluorinating agent described herein. In certain embodiments, a kit of the invention includes a palladium(III) complex of Formula (G-1); and a fluorinating agent described herein. In certain embodiments, the fluorinating agent is an N-fluorinated amine or N-fluorinated quaternary amine salt. In certain embodiments, the fluorinating agent is 1-(chloromethyl)-4-fluoro-1,4-diazoniabicyclo[2.2.2]octane bis(tetrafluoroborate) (F-TEDA-BF$_4$/Selectfluor®). In certain embodiments, the fluorinating agent is enriched with $^{18}$F.

In certain embodiments, a kit of the invention further includes an aryl or heteroaryl substrate of Formula (D), (E), or (F).

The kits provided may further include a container (e.g., a vial, ampule, bottle, syringe, flask, tube, beaker, dish, microtiter plate, and/or dispenser package, or other suitable container), a solvent (e.g., a suitable solvent described herein), or an organic or inorganic agent (e.g., a phase-transfer agent, a solubilizing agent, a stabilizing agent, an anti-oxidative agent, protecting agent, deprotecting agent, and/or a preservative agent). In some embodiments, the kits further include instructions for using the kits of the invention. In certain embodiments, the kits and instructions provide for preparing the compounds described herein (e.g., aryl or heteroaryl fluorides). In certain embodiments, the kits and instructions provide for preparing the compounds of Formula (I), (II), or (III). In certain embodiments, the kits and instructions provide for preparing the compounds of Formula (I), (II), or (III) and isotopically labeled derivatives (e.g., $^{18}$F-labeled derivatives) thereof.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Materials and Methods

Reactions were carried out under ambient atmosphere unless otherwise noted. Purified compounds were further dried under high vacuum (0.01-0.05 Torr). Yields refer to purified and spectroscopically pure compounds. Thin layer chromatography (TLC) was performed using EMD TLC plates pre-coated with 250 μm thickness silica gel 60 F$_{254}$ plates and visualized by fluorescence quenching under UV light and KMnO$_4$ stain. Flash chromatography was performed using silica gel (230-400 mesh) purchased from Silicycle Inc. Melting points were measured on a Thomas Scientific Uni-Melt capillary melting point apparatus. All melting points were measured in open capillaries and are uncorrected. NMR spectra were recorded on either a Varian Unity/Inova 600 spectrometer operating at 600 MHz for $^1$H acquisitions, a Varian Unity/Inova 500 spectrometer operating at 500 MHz and 125 MHz for $^1$H and $^{13}$C acquisitions, respectively, or a Varian Mercury 400 spectrometer operating at 400 HMz and 375 MHz for $^1$H and $^{19}$F acquisitions, respectively. Chemical shifts are reported in ppm with the solvent resonance as the internal standard ($^1$H: CDCl$_3$, δ 7.26; (CD$_3$)$_2$SO, δ2.50; CD$_3$CN, δ1.94; (CD$_3$)$_2$CO, δ2.05), ($^{13}$C: CDCl$_3$, δ77.16; CD$_3$CN, δ81.32, (CD$_3$)$_2$SO, δ39.52; (CD$_3$)$_2$CO, δ29.84, 206.26) (Fulmer, G. R.; Miller, A. J. M.; Sherden, N. H.; Gottlieb, H. E.; Nudelman, A.; Stoltz, B. M.; Bercaw, J. E.; Goldberg, K. I. *Organometallics* 2010, 29, 2176-2179). Data is reported as follows: s=singlet, br=broad, d=doublet, t=triplet, q=quartet, quin=quintet, m=multiplet; coupling constants in Hz; integration. All deuterated solvents were purchased from Cambridge Isotope Laboratories. Solution-state magnetic susceptibility measurements were obtained using the Evans method (Evans, D. F. *J. Chem. Soc.* 1959, 2003-2005) and are reported as follows: (field strength, solvent, temperature): μeff (concentration in mg/mL). EPR spectra were recorded on a Bruker ElexSys E500 EPR spectrometer operating at X-band frequency (9 GHz). UV-vis/NIR spectra were measured on a PerkinElmer Lambda 750 spectrophotometer. Electrochemical measurements were made using a CH Instruments Model 600E Series Electrochemical Analyzer/Workstation. High-resolution mass spectra were obtained using an Agilent ESI-TOF (6210) mass spectrometer or a Bruker q-TOF Maxis Impact mass spectrometer. LC/MS data were obtained using a Shimadzu LCMS-2020. Pd(OAc)$_2$ was purchased from Strem. HBF$_4$·OEt$_2$ was purchased from Alfa Aesar. 1-Chloromethyl-4-fluoro-1,4-diazoniabicyclo[2.2.2] octane bis(tetrafluoroborate) (Selectfluor®) and 2,2':6',2''-terpyridine (terpy) were purchased from Strem or SigmaAldrich. All chemicals were used as received. DMF was ACS Reagent grade, purchased from SigmaAldrich; MeCN was ACS grade, purchased from BDH. These solvents were used as received without further purification.

Representative Procedure for Evaluation of C—H Fluorination Reaction Using Selectfluor and Catalyst 1

Under N$_2$ atmosphere, an oven-dried 4 mL vial was charged 3,5-bis(trifluoromethyl)biphenyl (29.0 mg, 100 μmol, 1.0 equiv.), Selectfluor (71 mg, 200 μmol, 2.0 equiv.) and acetonitrile (0.5 mL). To a separate 4 mL vial, a solution of the given Pd(II) complex was formed from the appropriate Pd(II) source and ligands (5 mol % Pd(II) per 0.5 mL). The catalyst solution was then added to the reaction mixture (final c=0.1 M) and the resulting reaction mixture was stirred at 25, 50 or 80° C. for 24 h. After cooling to room temperature, 1,4-bistrifluoromethylbenzene (3.6 mg, 2.6 μl, 17 μmol, 0.17 equiv.) was added to the reaction mixture, stirred and a sample (approx. 0.1 mL) was diluted with CD$_3$CN (0.5 mL) and a yield was determined by $^{19}$F NMR using 1,4-bis(trifluoromethyl)benzene as an internal standard (standard: δ −63.4 ppm, 6 F; compared with product peaks at δ −113.8 and −118.2 ppm; first relaxation time of 10 s to ensure accurate integration.

Experimental Procedures and Compound Characterization

I. Preparation of Substrates for Fluorination

Nortropinone (4-biphenyl))sulfonamide (2q)

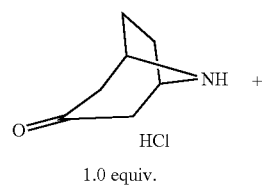

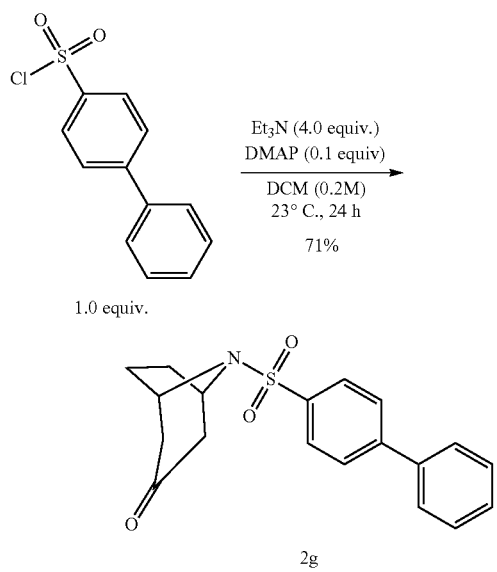

A 50 mL round bottom flask was charged with nortropinone hydrochloride (0.808 g, 5.00 mmol, 1.00 equiv.), dichloromethane (25 mL, c=0.2 M), 4-biphenyl sulfonyl chloride (1.27 g, 5.00 mmol, 1.00 equiv.), triethylamine (2.0 g, 2.8 mL, 20 mmol, 4.0 equiv.) and 4-dimethylamino pyridine (61 mg, 0.50 mmol, 0.10 equiv.) were added. After 24 h the reaction mixture was diluted with dichloromethane (100 mL) and washed with 0.5 M HCl (150 mL). The aqueous layer was extracted with dichloromethane (3×50 mL) and the combined organic phases were dried over sodium sulfate, filtered and concentrated under reduced pressure. The resulting residue was purified by silica gel column chromatography, eluting with dichloromethane and ethyl acetate (90:10 (v/v)) to afford nortropinone (4-biphenyl))sulfonamide 2q (1.12 g, 3.27 mmol, 65%) as a colorless solid. R$_f$=0.40 (ethyl acetate/dichloromethane, 10:90 (v/v)).

NMR Spectroscopy: $^1$H NMR (500 MHz, CDCl$_3$, 23° C., δ): 7.97 (d, J=8.8 Hz, 2H), 7.74 (d, J=8.8 Hz, 2H), 7.63-7.59 (m, 2H), 7.52-7.46 (m, 2H), 7.45-7.41 (m, 1H), 4.55 (tt, J=3.9, 2.1 Hz, 2H), 2.83 (dd, J=16.4, 4.6 Hz, 2H), 2.48-2.27 (m, 2H), 1.84-1.74 (m, 2H), 1.66-1.59 (m, 2H) ppm. $^{13}$C NMR (126 MHz, CDCl$_3$, 23° C., δ): δ 206.9, 146.2, 139.1, 138.4, 129.2, 128.8, 127.9 (d, J=1.6 Hz), 127.4, 56.2, 50.4, 29.5 ppm. HRMS-ESI (m/z) calculated for C$_{19}$H$_{19}$S$_1$NO$_3$Na [M+Na]$^+$, 364.0978; found, 364.0981.

II. Preparation of Palladium Precursor [(Terpy)Pd(MeCN)][BF$_4$]$_2$ (S1)

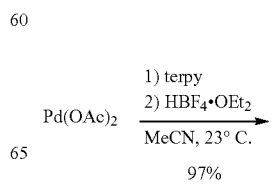

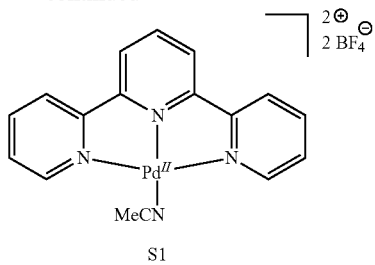

S1

To Pd(OAc)$_2$ (4.49 g, 20.0 mmol, 1.00 equiv) in MeCN (300 mL) at 23° C. was added 2,2':6',2''-terpyridine (4.67 g, 20.0 mmol, 1.00 equiv). The reaction mixture was stirred for 20 minutes, affording a pink/orange slurry. To this slurry was added HBF$_4$.OEt$_2$ (5.63 mL, 6.64 g, 41.0 mmol, 2.05 equiv.) via syringe. The reaction mixture was stirred vigorously for 30 min, at which point a suspension of tan solids was observed and Et$_2$O (250 mL) was added. The solids were collected by filtration and washed with Et$_2$O (200 mL). The combined solids were then dried under vacuum to afford 9.07 g of the title compound as a pale tan solid (97% yield). Spectra matched that previously reported. This procedure was adapted from the previously published procedure from Mazzotti et al., *J. Am. Chem. Soc.*, 2013, 135, 14012-14015.

III. Palladium Catalyzed Fluorination of Arenes (i) Representative Procedure A: C—H Fluorination Reaction Using NFSI or

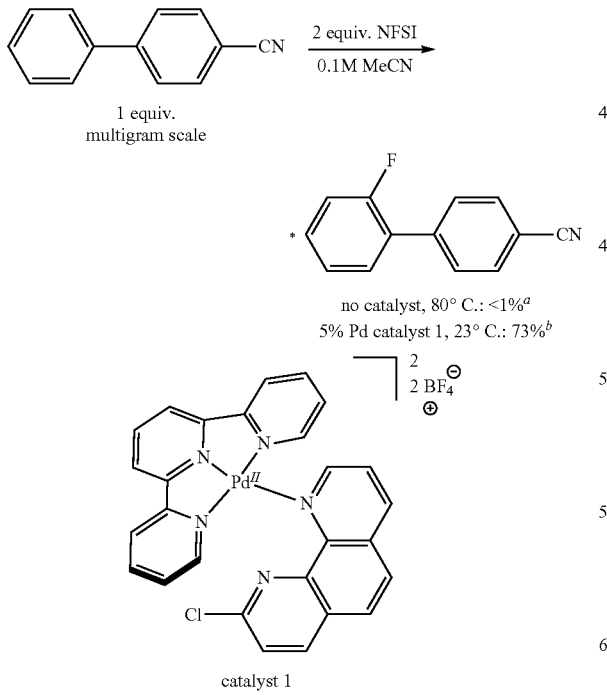

catalyst 1

[a] Yield based on $^{19}$F NMR. [b] Yield and ortho/para ration (73:27) was determined by $^{19}$F and $^1$H NMR.

Under N$_2$ atmosphere, an oven-dried 20 mL vial was charged with arene (1.00 mmol, 1.00 equiv.), either NFBS or NFSI (631 mg, 2.00 mmol, 2.00 equiv.) or Selectfluor (709 mg, 2.00 mmol, 2.00 equiv.), and acetonitrile (5.0 mL). To a separate 20 mL vial, Pd(II) terpyridine acetonitrile tetrafluoroborate complex (Pd(terpy)(MeCN)(BF$_4$)$_2$, [Si]) (27.7 mg, 50.0 μmol, 5.00 mol %) and 2-chloro-phenanthroline (10.7 mg, 50.0 μmol, 5.00 mol %) were added and dissolved in acetonitrile (5.0 mL). The catalyst-containing solution was added to the mixture of (hetero)arene and oxidant (final c=0.10 M). The resulting reaction mixture was stirred at 25° C. for 24 h and was then transferred to a separatory funnel. Chloroform (75 mL) was added and the organic layer was washed water (50 mL) with added brine (10 mL). The aqueous layer was extracted with chloroform (4×75 mL) and the combined organic layers were dried over sodium sulfate, filtered, and concentrated in vacuo. The residue was dissolved in dichloromethane (2 mL), loaded onto a short plug of silica (20 g) and eluted with an appropriate solvent (50 mL). A mixture of the fluorinated product isomers, remaining starting material, and minor inseparable impurities was obtained and a yield was determined by $^{19}$F NMR using 1,4-bis(trifluoromethyl)benzene (δδ−63.4 ppm, 6 F) as an internal standard with a first relaxation time of 10 s to ensure accurate integration.

(ii) Representative Procedure B: C—H Fluorination Reaction without Palladium Catalyst Under N$_2$ atmosphere, an oven-dried 4 mL vial was charged with arene (100.0 μmol, 1.00 equiv.), Selectfluor (70.8 mg, 200.0 μmol, 2.00 equiv.) and acetonitrile (1.0 mL, c=0.10 M). The resulting reaction mixture was stirred at 80° C. for 24 h. After cooling to room temperature, 1,4-bistrifluoromethylbenzene (3.6 mg, 2.6 μl, 17 μmol, 0.17 equiv.) was added to the reaction mixture, stirred and a sample (approx. 0.1 mL) was diluted with CD$_3$CN (0.5 mL) and a yield was determined by $^{19}$F NMR using 1,4-bis(trifluoromethyl)benzene (δ −63.4 ppm, 6 F) as an internal standard with a first relaxation time of 10 s to ensure accurate integration.

Example 1. 1-tert-Butyl-2-fluoro-3,5-dimethylbenzene (3aa) and 1-tert-butyl-2-fluoro-3,5-dimethylbenzene (3ab)

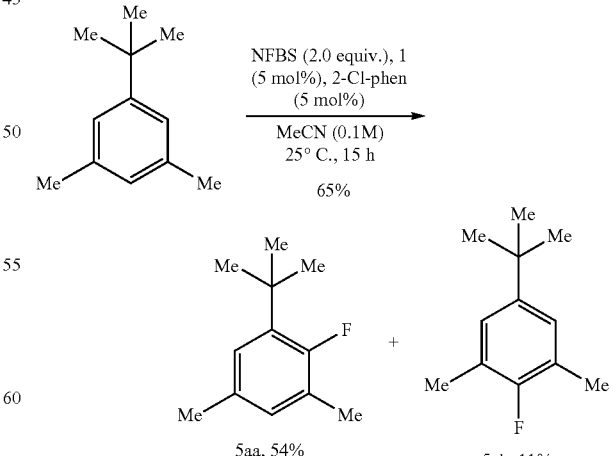

A mixture of palladium complex S1 (27.7 mg, 50.0 μmol, 5.00 mol %) and 2-chloro-phenanthroline (10.7 mg, 50.0 μmol, 5.00 mol %.) was dissolved in acetonitrile (5.0 mL).

This mixture was added to a 20 mL vial containing a solution of NFBS (315 mg, 1.00 mmol, 2.00 equiv.) and 1-tert-butyl-3,5-dimethylbenzene (162 mg, 188 μl, 1.00 mmol, 1.00 equiv.) in acetonitrile (5.0 mL, final c=0.10 M). The reaction mixture was stirred for 24 hours at 25° C. and then transferred to a separatory funnel. Pentane (50 mL) was added and the organic layer was washed with saturated aqueous NaHCO$_3$ solution (1×25 mL). The aqueous layer was extracted with pentane (4×50 mL). The combined organic layers were dried over magnesium sulfate, filtered, and concentrated in vacuo at 40° C. to afford a yellow oil. The residue was dissolved in hexane (2 mL), loaded onto a short plug of silica (20 g) and eluted with hexane. A colorless oil (136 mg) containing the title compounds 3aa and 3ab (118 mg, 0.65 mmol, 65% yield, 3aa:3ab (83:17)), 1-tert-butyl-3,5-dimethylbenzene and residual solvent was obtained. The solvent and starting material content of the residue was established by $^1$H NMR spectrum of the mixture. The yield and selectivity were determined by $^{19}$F using 1,4-bis(trifluoromethyl)benzene as an internal standard (standard: δ -63.4 ppm, 6 F; compared with product peaks at δ -119.7 and -126.9 ppm; first relaxation time of 10 s to ensure accurate integration). The spectra matched the reported spectra for the title compound 3ab, reported in Yamato et al., J. Chem. Soc., Perkin Trans. 1, 1987, 1-7. R$_f$=0.70 (hexane).

NMR Spectroscopy: $^1$H NMR (500 MHz, CDCl$_3$, 23° C., δ): δ 7.04 (s, 1H), 6.93 (dd, J=7.6, 2.2 Hz, 1H), 6.89-6.83 (m, 1H), 2.35 (d, J=0.7 Hz, 3H), 2.30 (d, J=1.0 Hz, 2H), 2.28 (d, J=2.1 Hz, 1H), 2.25 (d, J=2.6 Hz, 2H), 1.39 (d, J=1.1 Hz, 6H), 1.34 (s, 4H), 1.32 (s, 1H). ppm. $^{13}$C NMR (126 MHz, CDCl$_3$, 23° C., δ): 158.7 (d, J=244.1 Hz), 151.3, 137.5, 136.3 (d, J=12.3 Hz), 132.2 (d, J=4.2 Hz), 129.7 (d, J=5.2 Hz), 127.2, 125.9 (d, J=4.4 Hz), 125.3 (d, J=5.7 Hz), 125.1 (d, J=20.1 Hz), 123.3, 34.6, 34.3, 34.3, 31.7, 31.6, 30.2 (d, J=3.7 Hz), 21.7, 21.0, 15.0 (d, J=4.4 Hz), 14.9 (d, J=6.6 Hz) ppm. 1-tert-butyl-2-fluoro-3,5-dimethylbenzene (3aa): $^{19}$F NMR (471 MHz, CDCl$_3$, 23° C., δ) -119.7 ppm. 1-tert-butyl-2-fluoro-3,5-dimethylbenzene (3ab): $^{19}$F NMR (471 MHz, CDCl$_3$, 23° C., δ) -126.9 ppm. HRMS-FIA(m/z) calculated for C$_{12}$H$_{18}$F [M+H]$^+$, 181.1393; found, 181.1387.

Reaction without Catalyst.

Under N$_2$ atmosphere, an oven-dried 4 mL vial was charged with Selectfluor (71 mg, 200 μmol, 2.0 equiv.) and 1-tert-butyl-3,5-dimethylbenzene (81 mg, 9.4 μl, 100 μmol, 1.0 equiv.) in acetonitrile (1.0 mL, c=0.10 M). The resulting reaction mixture was stirred at 80° C. for 24 h. After cooling to room temperature, 1,4-bistrifluoromethylbenzene (3.6 mg, 2.6 μl, 17 μmol, 0.17 equiv.) was added to the reaction mixture, stirred and a sample (approx. 0.1 mL) was diluted with CD$_3$CN (0.5 mL) and the yield of the title products was determined by $^{19}$F NMR using 1,4-bis(trifluoromethyl)benzene as an internal standard to be 23% (3aa:3ab 52:48) and 69% of 11 new, unidentified fluorine peaks (based on $^{19}$F NMR integration relative to the standard between δ -110 and -130 ppm; the percentage does not necessarily correlate to a yield of product because it does not correct for difluoro- or poly-fluoroarenes).

Example 2. 4-Fluoro-bromobenzene (3ba) and 2-fluoro-bromobenzene (3bb)

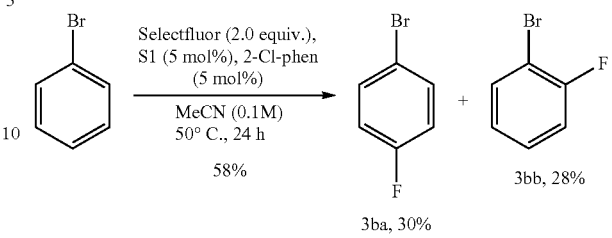

A mixture of palladium complex S1 (27.7 mg, 50.0 μmol, 5.00 mol %) and 2-chloro-phenanthroline (10.7 mg, 50.0 μmol, 5.00 mol %.) was dissolved in acetonitrile (5.0 mL). This mixture was added to a 20 mL vial containing a solution of Selectfluor (709 mg, 2.00 mmol, 2.00 equiv.) and bromobenzene (157 mg, 106 μl, 1.0 mmol, 1.0 equiv.) in acetonitrile (5.0 mL, final c=0.10 M). The reaction mixture was stirred for 12 hours at 50° C. and then transferred to a separatory funnel. Pentane (25 mL) was added and the organic layer was washed with saturated aqueous NaHCO$_3$ solution (1×25 mL). The aqueous layer was extracted with pentane (3×25 mL). The combined organic layers were filtered through a short plug of silica and and concentrated in vacuo at 20° C. to afford a colorless oil (178 mg) containing the title compound (101 mg, 0.58 mmol, 58% yield, 3ba:3bb (62:38)), bromobenzene, pentane and minor fluorinated impurities. The remaining solvent was not removed from the sample due to volatility of the product. The solvent and bromobenzene content of the residue was established by $^1$H NMR spectrum of the mixture (diagnostic signal for bromobenzene: δ 7.52-7.48 ppm (m, 1H)). The yield and selectivity were determined by $^{19}$F using 1,4-bis (trifluoromethyl)benzene as an internal standard (standard: δ -63.4 ppm, 6 F; compared with product peaks at δ -110.2 and -118.4 ppm; first relaxation time of 10 s to ensure accurate integration). A sample with of higher purity was obtained for characterization by further purification using column chromatography with spherical silica gel (Biotage ZIP Sphere 30 g, pentane). The spectra matched the reported spectra for the title compounds. (See Mazzotti et al., J Am. Chem. Soc., 2013, 135, 14012-14015; Seo et al., Chem. Commun., 2012, 48, 8270-8272). R$_f$=0.70 (hexane).

NMR Spectroscopy: 1-Bromo-4-fluorobenzene (3ba): $^1$H NMR (500 MHz, CDCl$_3$, 23° C., δ): 7.47-7.41 (m, 2H), 6.99-6.92 (m, 2H) ppm. $^{13}$C NMR (125 MHz, CDCl$_3$, 23° C., δ): 162.0 (d, J=246.6 Hz), 133.1 (d, J=7.8 Hz), 117.4 (d, J=22.3 Hz), 116.7 (d, J=3.2 Hz) ppm. $^{19}$F NMR (470 MHz, CDCl$_3$, 23° C., δ): -118.4 ppm. 1-Bromo-2-fluorobenzene (3bb): $^1$H NMR (500 MHz, CDCl$_3$, 23° C., δ): 7.59-7.52 (m, 1H), 7.28 (m, 1H), 7.12 (td, J=8.5, 1.5 Hz, 1H), 7.03 (td, J=7.7, 1.5 Hz, 1H) ppm. $^{13}$C NMR (125 MHz, CDCl$_3$, 23° C., δ): 159.3 (d, J=247.6 Hz), 133.7 (s), 129.1 (d, J=7.2 Hz), 125.4 (d, J=3.9 Hz), 116.7 (d, J=22.5 Hz), 109.2 (d, J=20.9 Hz) ppm. $^{19}$F NMR (470 MHz, CDCl$_3$, 23° C., δ): -110.2 ppm. HRMS-FIA(m/z) calculated for C$_6$H$_4$BrF [M]+, 173.9475; found, 173.9475.

Reaction without Catalyst:

Under N$_2$ atmosphere, an oven-dried 4 mL vial was charged with Selectfluor (71 mg, 200 μmol, 2.0 equiv.) and bromobenzene (81 mg, 9.4 μl, 100 μmol, 1.0 equiv.) in acetonitrile (1.0 mL, c=0.10 M). The resulting reaction mixture was stirred at 80° C. for 24 h. After cooling to room temperature, 1,4-bistrifluoromethylbenzene (3.6 mg, 2.6 μl, 17 μmol, 0.17 equiv.) was added to the reaction mixture, stirred and a sample (approx. 0.1 mL) was diluted with CD₃CN (0.5 mL) and the yield of the title products was determined by ¹⁹F NMR using 1,4-bis(trifluoromethyl)benzene as an internal standard to be <1%.

Example 3. 4-Fluoro-chlorobenzene (3ca) and 2-fluoro-chlorobenzene (3cb)

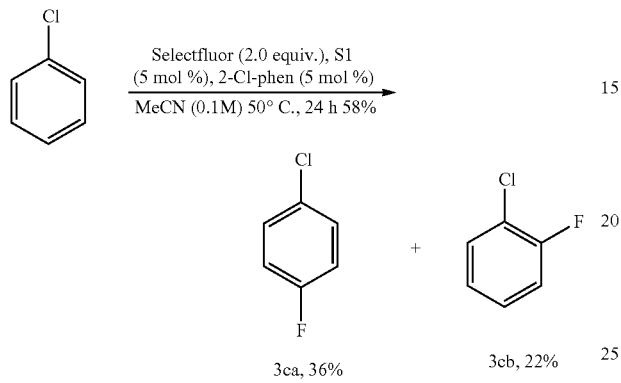

3ca, 36%    3cb, 22%

A mixture of palladium complex S1 (27.7 mg, 50.0 μmol, 5.00 mol %) and 2-chloro-phenanthroline (10.7 mg, 50.0 μmol, 5.00 mol %.) was dissolved in acetonitrile (5.0 mL). This mixture was added to a 20 mL vial containing a solution of Selectfluor (709 mg, 2.00 mmol, 2.00 equiv.) and chlorobenzene (113 mg, 102 μl, 1.0 mmol, 1.0 equiv.) in acetonitrile (5.0 mL, final c=0.10 M). The reaction mixture was stirred for 12 hours at 50° C. and then transferred to a separatory funnel. Pentane (25 mL) was added and the organic layer was washed with saturated aqueous NaHCO₃ solution (1×25 mL). The aqueous layer was extracted with pentane (3×25 mL). The combined organic layers were filtered through a short plug of silica and and concentrated in vacuo at 0° C. to afford a colorless oil (153 mg) containing the title compound (76 mg, 0.58 mmol, 58% yield, 3ca:3cb (62:38)), chlorobenzene pentane and other minor impurities. The remaining solvent was not removed from the sample due to volatility of the product. The solvent and chlorobenzene content of the residue was established by ¹H NMR spectrum of the mixture (signals for chlorobenzene overlap with product: δ 7.20-7.36 ppm (m, 5H)). The yield and selectivity were determined by ¹⁹F using 1,4-bis(trifluoromethyl)benzene as an internal standard (standard: δ −63.4 ppm, 6 F; compared with product peaks at δ −115.5 and −116.0 ppm; first relaxation time of 10 s to ensure accurate integration). The yield was also confirmed by a GC assay with 1,4-bis(trifluoromethyl)benzene as an internal standard. The spectra matched the reported spectra for the title compounds and authentic samples. See Dubbaka, et al., *Tetrahedron*, 2014, 70, 9676-9681; Dmowski et al., *J. Fluor. Chem.*, 1998, 88, 143-151. $R_f$=0.70 (hexane). HRMS-APPI (m/z) calculated for $C_6H_4ClF$ [M]⁺, 129.9980; found, 129.9980.

NMR Spectroscopy: 1-Chloro-4-fluorobenzene (3ca): ¹H NMR (500 MHz, CDCl₃, 23° C., δ): 7.36-7.27 (m, 2H), 7.00 (dd, J=9.0, 8.2 Hz, 2H) ppm. ¹³C NMR (125 MHz, CDCl₃, 23° C., δ): 161.48 (d, J=246.1 Hz), 130.1 (d, J=8.1 Hz), 129.32 (d, J=3.2 Hz), 116.9 (d, J=23.2 Hz) ppm. ¹⁹F NMR (470 MHz, CDCl₃, 23° C., δ): −116.0 ppm. 1-Chloro-2-fluorobenzene (3cb):

¹H NMR (500 MHz, CDCl₃, 23° C., δ): 7.40 (td, J=7.7, 1.7 Hz, 1H), 7.32-7.21 (m, 1H), 7.14 (ddd, J=9.6, 8.2, 1.5 Hz, 1H), 7.12-7.05 (m, 1H) ppm. ¹³C NMR (125 MHz, CDCl₃, 23° C., δ): 158.37 (d, J=248.6 Hz), 130.8, 128.3 (d, J=7.2 Hz), 125.0 (d, J=4.1 Hz), 121.1, 116.8 (d, J=20.8 Hz) ppm. ¹⁹F NMR (470 MHz, CDCl₃, 23° C., δ): −115.5 ppm.

Reaction without Catalyst:

Under N₂ atmosphere, an oven-dried 4 mL vial was charged with Selectfluor (71 mg, 200 μmol, 2.0 equiv.) and chlorobenzene (81 mg, 9.4 μl, 100 μmol, 1.0 equiv.) in acetonitrile (1.0 mL, c=0.10 M). The resulting reaction mixture was stirred at 80° C. for 24 h. After cooling to room temperature, 1,4-bistrifluoromethylbenzene (3.6 mg, 2.6 μl, 17 μmol, 0.17 equiv.) was added to the reaction mixture, stirred and a sample (approx. 0.1 mL) was diluted with CD₃CN (0.5 mL) and the yield of the title products was determined by ¹⁹F NMR using 1,4-bis(trifluoromethyl)benzene as an internal standard to be <1%.

Example 4. 4'-Cyano-2-fluorobiphenyl (3da) and 4'-cyano-4-fluorobiphenyl (3db)

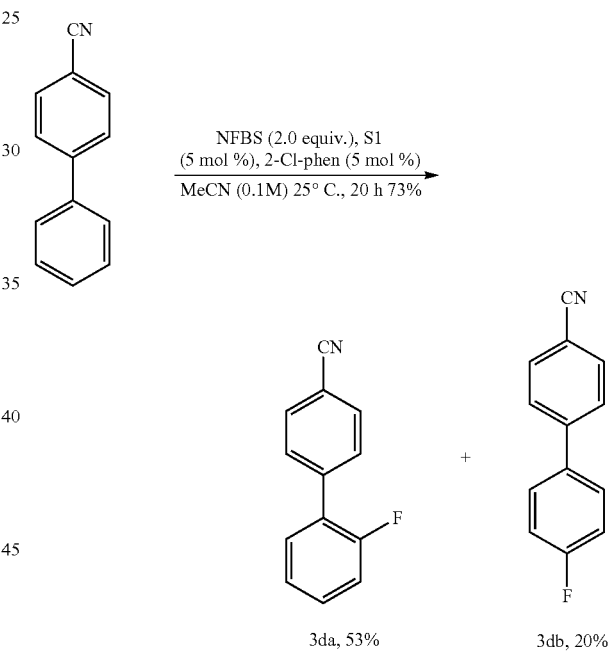

3da, 53%    3db, 20%

A mixture of palladium complex S1 (27.7 mg, 50.0 μmol, 5.00 mol %) and 2-chloro-phenanthroline (10.7 mg, 50.0 μmol, 5.00 mol %.) was dissolved in acetonitrile (5.0 mL). This mixture was added to a 20 mL vial containing a solution of NFBS (615 mg, 2.00 mmol, 2.00 equiv.) and 4-cyanobiphenyl (179 mg, 1.0 mmol, 1.0 equiv.) in acetonitrile (5.0 mL, final c=0.10 M). The reaction mixture was stirred for 20 hours at 25° C. The remaining oxidant was quenched by adding a solution of Na₂S₂O₃(H₂O)₅ (1.22 g, 5.00 mmol, 5.00 equiv.) in water (20 mL) and stirring for 30 min. The mixture was added to a separatory funnel with 50 mL dichloromethane. The aqueous layer was extracted with dichloromethane (3×50 mL). The combined organic layers were dried over sodium sulfate, filtered, and concentrated in vacuo at 40° C. to afford a pale yellow solid. The residue was dissolved in dichloromethane (2 mL), loaded onto a short plug of silica (20 g) and eluted with dichloromethane. and concentrated in vacuo to afford a pale yellow solid (191 mg) containing the title compounds (144 mg, 0.73 mmol, 73% yield, 3da:3db (73:27)), 4-cyano-biphenyl and minor inseparable impurities. The 4-cyano-biphenyl content of the residue was established by 1H NMR spectrum of the mixture (diagnostic signal at δ 7.48 ppm (m, 2H)). The yield and selectivity were determined by $^{19}$F using 1,4-bis(trifluoromethyl)benzene as an internal standard (standard: δ −63.4 ppm, 6 F; compared with product peaks at δ −113.8 and −118.2 ppm; first relaxation time of 10 s to ensure accurate integration). The spectra matched the reported spectra for the title compounds and authentic samples. See Zhou et al., J. Org. Chem., 2012, 77, 10468-10472; Bernhardt et al., Angew. Chem., Int. Ed., 2011, 50, 9205-9209.

Example 5. Larger Scale Fluorination Under Ambient Atmosphere

A mixture of palladium complex S1 (416 mg, 750 μmol, 5.00 mol %) and 2-chloro-phenanthroline (161 mg, 750 μmol, 5.00 mol %.) was dissolved in acetonitrile (75 mL). This mixture was added to a 20 mL vial containing a solution of NFBS (9.46 g, 30.0 mmol, 2.00 equiv.) and 4-cyanobiphenyl (2.69 g, 15.0 mmol, 1.0 equiv.) in acetonitrile (75 mL, final c=0.10 M). The reaction mixture was stirred for 20 hours at 25° C. The remaining oxidant was quenched by adding a solution of $Na_2S_2O_3 \cdot (H_2O)_5$ (14.9 g, 60.0 mmol, 4.00 equiv.) in water (200 mL) and stirring for 1 hour. The mixture was added to a separatory funnel with 200 mL dichloromethane. The aqueous layer was extracted with dichloromethane (3×200 mL). The combined organic layers were dried over sodium sulfate, filtered, and concentrated in vacuo at 40° C. to afford a pale yellow solid. The residue was dissolved in dichloromethane (15 mL), loaded onto a short plug of silica (150 g) and eluted with dichloromethane and concentrated in vacuo to afford a pale yellow solid (2.86 g) containing the title compounds (2.2 g, 11 mmol, 73% yield, 3da:3db (73:27)), 4-cyano-biphenyl (710 mg, 26%) and minor inseparable impurities. The yield and selectivity were as determined by $^1$H and $^{19}$F NMR using the relative integrations of the cyanophenyl moiety protons (δ 7.60-7.75 ppm, 4H combined for all components), cyanobiphenyl diagnostic protons (δ 7.48 ppm (m, 2H)) and product protons (δ 7.25-7.13 ppm (m, 2H)) combined with the relative ratio of the $^{19}$F NMR signals (δ −113.8 and −118.2 ppm). $R_f$=0.75 (dichloromethane).

NMR Spectroscopy: 4'-cyano-2-fluorobiphenyl (3da): $^1$H NMR (500 MHz, CDCl$_3$, 23° C., δ): 7.75-7.60 (m, 4H), 7.45-7.36 (m, 2H), 7.25-7.16 (m, 2H) ppm. $^{13}$C NMR (125 MHz, CDCl$_3$, 23° C., δ): 159.8 (d, J=249.3 Hz), 140.6, 135.4, 132.4, 130.6 (d, J=3.0 Hz), 130.5 (d, J=8.6 Hz), 129.8 (d, J=3.0 Hz), 127.8 (d, J=19.1 Hz), 127.3 (d, J=13.1 Hz), 124.9 (d, J=3.6 Hz), 119.0, 116.6 (d, J=22.6 Hz), 111.1 ppm. $^{19}$F NMR (470 MHz, CDCl$_3$, 23° C., δ): −118.2 ppm. 4'-cyano-4-fluorobiphenyl (3db): $^1$H NMR (500 MHz, CDCl$_3$, 23° C., δ): 7.75-7.60 (m, 4H), 7.60-7.53 (m, 2H), 7.21-7.13 (m, 2H) ppm. $^{13}$C NMR (125 MHz, CDCl$_3$, 23° C., δ): 163.3 (d, J=248.9 Hz), 144.6, 135.4, 132.8, 129.1 (d, J=8.3 Hz), 127.4, 118.9, 116.3 (d, J=21.5 Hz), 111.5 ppm. $^{19}$F NMR (470 MHz, CDCl$_3$, 23° C., δ): −113.8 ppm. HRMS-EI (m/z) calculated for $C_{13}H_8FN$ [M]$^+$, 197.0641; found, 197.0640.

Reactions without Catalyst

Under $N_2$ atmosphere, an oven-dried 4 mL vial was charged with Selectfluor (71 mg, 200 μmol, 2.0 equiv.), 4-cyanobiphenyl (19.7 mg, 100 μmol, 1.0 equiv.), and acetonitrile (1.0 mL, c=0.10 M). The resulting reaction mixture was stirred at 80° C. for 24 h. After cooling to room temperature, 1,4-bistrifluoromethylbenzene (3.6 mg, 2.6 μl, 17 μmol, 0.17 equiv.) was added to the reaction mixture, stirred and a sample (approx. 0.1 mL) was diluted with CD$_3$CN (0.5 mL) and the yield of the title products were determined by $^{19}$F NMR using 1,4-bis(trifluoromethyl)benzene as an internal standard to be 19% (5da:5db 79:21).

Under $N_2$ atmosphere, an oven-dried 4 mL vial was charged with NFBS (63.0 mg, 200.0 μmol, 2.00 equiv.), cyanobiphenyl (19.7 mg, 100 μmol, 1.0 equiv.), and acetonitrile (1.0 mL, c=0.10 M). The resulting reaction mixture was stirred at 80° C. for 24 h. After cooling to room temperature, 1,4-bistrifluoromethylbenzene (3.6 mg, 2.6 μl, 17 μmol, 0.17 equiv.) was added to the reaction mixture, stirred and a sample (approx. 0.1 mL) was diluted with CD$_3$CN (0.5 mL) and the yield of the title products was determined by $^{19}$F NMR using 1,4-bis(trifluoromethyl)benzene as an internal standard to be <1%.

Example 6. 2-Fluoro-3',5'-bis(trifluoromethyl)biphenyl (3ea) and 4-fluoro-3',5'-bis(trifluoromethyl)biphenyl (3eb)

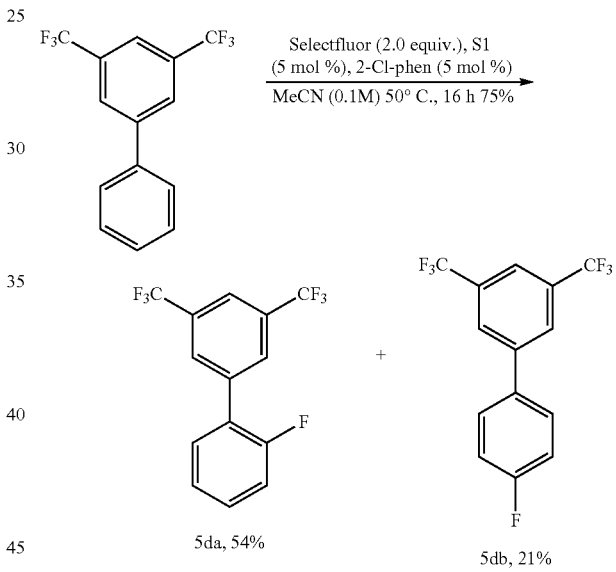

A mixture of palladium complex S1 (27.7 mg, 50.0 μmol, 5.00 mol %) and 2-chloro-phenanthroline (10.7 mg, 50.0 μmol, 5.00 mol %.) was dissolved in acetonitrile (5.0 mL). This mixture was added to a 20 mL vial containing a solution of Selectfluor (709 mg, 2.00 mmol, 2.00 equiv.) and 3,5-bis(trifluoromethyl)biphenyl (290 mg, 1.0 mmol, 1.0 equiv.) in acetonitrile (5.0 mL, final c=0.10 M). The reaction mixture was stirred for 16 hours at 50° C. and then transferred to a separatory funnel. Pentane (25 mL) was added and the organic layer was washed with saturated aqueous NaHCO$_3$ solution (25 mL). The aqueous layer was extracted with pentane (3×25 mL). The combined organic layers were filtered through a short plug of silica (20 g), eluted with pentane and concentrated in vacuo at 25° C. to afford a colorless oil (312 mg) containing the title compounds (230 mg, 0.75 mmol, 75% yield, 3ea: 3eb (72:28)), 3,5-bis(trifluoromethyl)biphenyl and pentane. The remaining solvent was not removed from the sample due to volatility of the product. The yield and selectivity were determined by $^{19}$F using 1,4-bis(trifluoromethyl)benzene as an internal standard (standard: δ −63.4 ppm, 6 F; compared with product peaks at δ −113.8 and −118.2 ppm; first relaxation time of 10 s to ensure accurate integration). The solvent content of the residue and selectivity was determined by integration of the $^1$H NMR spectrum of the mixture and the yield was $^{19}$F and $^1$H NMR using 1,4-bis(trifluoromethyl)benzene as an internal standard. The spectra matched the reported spectra for the title compound 3eb. See Minami et al., Angew. Chem., Int. Ed., 2015, 54, 4665-4668. $R_f$=0.75 (pentane). HRMS-FIA(m/z) calculated for $C_{14}H_7F_7$ [M]+, 308.0432; found, 308.0436.

NMR Spectroscopy: 2-fluoro-3',5'-bis(trifluoromethyl)biphenyl (3ea): $^1$H NMR (500 MHz, CDCl$_3$, 23° C., δ): 8.01 (s, 2H), 7.89 (s, 1H), 7.47 (td, J=7.7, 1.8 Hz, 1H), 7.45-7.40 (m, 1H), 7.29 (td, J=7.6, 1.2 Hz, 1H), 7.20 (t, J=8.7 Hz, 1H) ppm. $^{13}$C NMR (125 MHz, CDCl$_3$, 23° C., δ): 159.75 (d, J=249.2 Hz), 138.0, 132.0 (q, J=33.3 Hz), 130.9 (d, J=8.4 Hz), 130.6 (d, J=2.8 Hz), 129.3 (m), 126.3 (d, J=13.1 Hz), 125.0 (d, J=3.7 Hz), 123.5 (q, J=272.8 Hz), 121.6 (hept, J=3.3 Hz), 116.7 (d, J=22.5 Hz) ppm. $^{19}$F NMR (470 MHz, CDCl$_3$, 23° C., δ): −62.9 (3F), −118.0 (1F) ppm. 4-fluoro-3',5'-bis(trifluoromethyl)biphenyl (3eb): $^1$H NMR (500 MHz, CDCl$_3$, 23° C., δ): 7.97 (s, 2H), 7.86 (s, 1H), 7.59 (dd, J=8.8, 5.1 Hz, 2H), 7.23 (dd, J=8.3, 1.2 Hz, 2H), 132.4 (q, J=33.4 Hz). $^{13}$C NMR (125 MHz, CDCl$_3$, 23° C., δ): 163.5 (d, J=249.6 Hz), 142.5, 134.5, 134.5, 129.3 (m), 127.2, 123.5 (q, J=272.8 Hz), 121.1 (hept, J=3.8 Hz), 116.5 (d, J=21.7 Hz) ppm. $^{19}$F NMR (470 MHz, CDCl$_3$, 23° C., δ): −62.9 (3F), −112.8 (1F) ppm.

Reactions without Catalyst

Under N$_2$ atmosphere, an oven-dried 4 mL vial was charged with Selectfluor (71 mg, 200 μmol, 2.0 equiv.) and 3,5-bis(trifluoromethyl)biphenyl (29.0 mg, 100 μmol, 1.0 equiv.) in acetonitrile (1.0 mL, c=0.10 M). The resulting reaction mixture was stirred at 80° C. for 24 h. After cooling to room temperature, 1,4-bistrifluoromethylbenzene (3.6 mg, 2.6 μl, 17 μmol, 0.17 equiv.) was added to the reaction mixture, stirred and a sample (approx. 0.1 mL) was diluted with CD3CN (0.5 mL) and the yield of the title products was determined by $^{19}$F NMR using 1,4-bis(trifluoromethyl)benzene as an internal standard to be 7% (5ea:5eb 75:25).

Example 7. 1-(3-Bromopropyl)-2-fluorobenzene (3fa) and 1-(3-bromopropyl)-4-fluorobenzene (3fb)

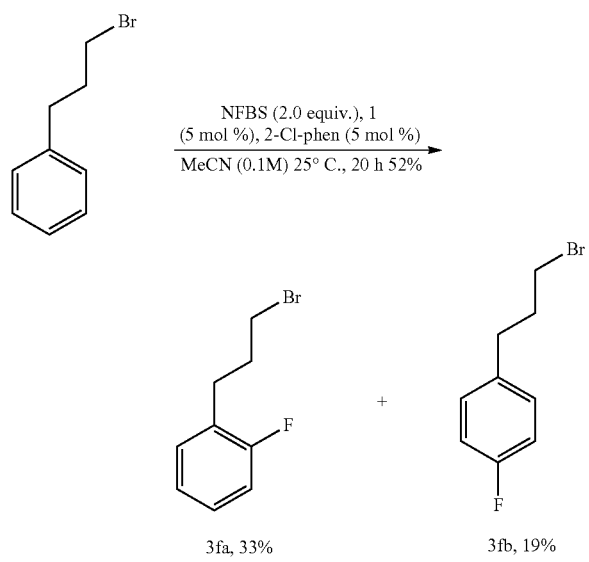

3fa, 33%  3fb, 19%

A mixture of palladium complex S1 (27.7 mg, 50.0 μmol, 5.00 mol %) and 2-chloro-phenanthroline (10.7 mg, 25 μmol, 5.0 mol %) was dissolved in acetonitrile (5.0 mL). This mixture was added to a 20 mL vial containing a solution of NFBS (315 mg, 1.00 mmol, 2.00 equiv.) and 3-bromopropylbenzene (199 mg, 152 μl, 1.00 mmol, 1.0 equiv.) in acetonitrile (5.0 mL, final c=0.10 M). The reaction mixture was stirred for 24 hours at 25° C. and then transferred to a separatory funnel. Pentane (50 mL) was added and the organic layer was washed with 5% sodium chloride solution (75 mL). The aqueous layer was extracted with pentane (4×50 mL). The combined organic layers were dried over sodium sulfate, filtered, and concentrated in vacuo at 40° C. to afford a yellow oil. The residue was dissolved in pentane (2 mL), loaded onto a short plug of silica (20 g) and eluted with pentane. A colorless oil (137 mg) containing the title compounds (112 mg, 0.52 mmol, 52% yield, 3fa:3fb (64:36)), 3-bromopropylbenzene and residual solvent was obtained. Residual solvent was not removed due to volatility of the product. The yield and selectivity were determined by $^{19}$F NMR using 1,4-bis(trifluoromethyl)benzene as an internal standard (standard: δ −63.4 ppm, 6 F; compared with product peaks at δ −115.5 and −116.0 ppm; first relaxation time of 10 s to ensure accurate integration). Purification using column chromatography with spherical silica gel (Biotage ZIP Sphere 30 g, dichloromethane:pentane 0:100 to 2:98 (v:v)), provided samples of 3fa (>95% pure by $^{19}$F NMR) and 3fb (contaminated with 3-bromopropylbenzene). The spectra matched the reported spectra for the title compounds. See European Patent, EP2168944. $R_f$=0.55 (pentane).

NMR Spectroscopy: 1-(3-bromopropyl)-2-fluorobenzene (3fa): $^1$H NMR (500 MHz, CDCl$_3$, 23° C., δ): 7.25-7.15 (m, 2H), 7.07 (td, J=7.5, 1.2 Hz, 1H), 7.02 (ddd, J=9.6, 8.1, 1.2 Hz, 1H), 3.41 (t, J=6.6 Hz, 2H), 2.82 (t, J=7.4 Hz, 2H), 2.18 (dq, J=8.5, 6.7 Hz, 2H) ppm. $^{13}$C NMR (126 MHz, CDCl$_3$, 23° C., δ): 161.2 (d, J=245.3 Hz), 130.9 (d, J=5.0 Hz), 128.0 (d, J=7.8 Hz), 127.4 (d, J=15.7 Hz), 124.1 (d, J=3.6 Hz), 115.4 (d, J=22.0 Hz), 33.0, 32.8, 27.6 (d, J=2.7 Hz) ppm. $^{19}$F NMR (471 MHz, CDCl$_3$, 23° C., δ) −118.6 ppm. 1-(3-bromopropyl)-2-fluorobenzene (3fb): $^1$H NMR (500 MHz, CDCl$_3$, 23° C., δ): 7.25-7.18 (m, 1H), 6.98 (t, J=8.7 Hz, 0H), 3.47-3.27 (m, 1H), 2.77 (dt, J=12.5, 7.4 Hz, 1H), 2.27-2.06 (m, 1H) ppm. $^{13}$C NMR (126 MHz, CDCl$_3$, 23° C., δ): 161.6 (d, J=244.3 Hz), 136.3 (d, J=3.4 Hz), 128.7 (d, J=7.1 Hz), 115.4 (d, J=20.9 Hz), 34.3, 33.3 ppm. $^{19}$F NMR (471 MHz, CDCl$_3$, 23° C., δ) −117.2 ppm. HRMS-APPI (m/z) calculated for $C_{12}H_{18}F$ [M]$^+$, 215.9945; found, 215.9947.

Reaction without Catalyst.

Under N$_2$ atmosphere, an oven-dried 4 mL vial was charged with Selectfluor (71 mg, 200 μmol, 2.0 equiv.) and 3-bromopropylbenzene (8.1 mg, 9.4 μl, 100 μmol, 1.0 equiv.) in acetonitrile (1.0 mL, c=0.10 M). The resulting reaction mixture was stirred at 80° C. for 24 h. After cooling to room temperature, 1,4-bistrifluoromethylbenzene (3.6 mg, 2.6 17 μmol, 0.17 equiv.) was added to the reaction mixture, stirred and a sample (approx. 0.1 mL) was diluted with CD$_3$CN (0.5 mL) and the yield of the title products was determined by $^{19}$F NMR using 1,4-bis(trifluoromethyl)benzene as an internal standard to be 24% (3fa:3fb 71:29).

Example 8. Nortropinone (4-(2'-fluoro-biphenyl))sulfonamide (3ga) and nortropinone (4-(4'-fluoro-biphenyl))sulfonamide (3gb)

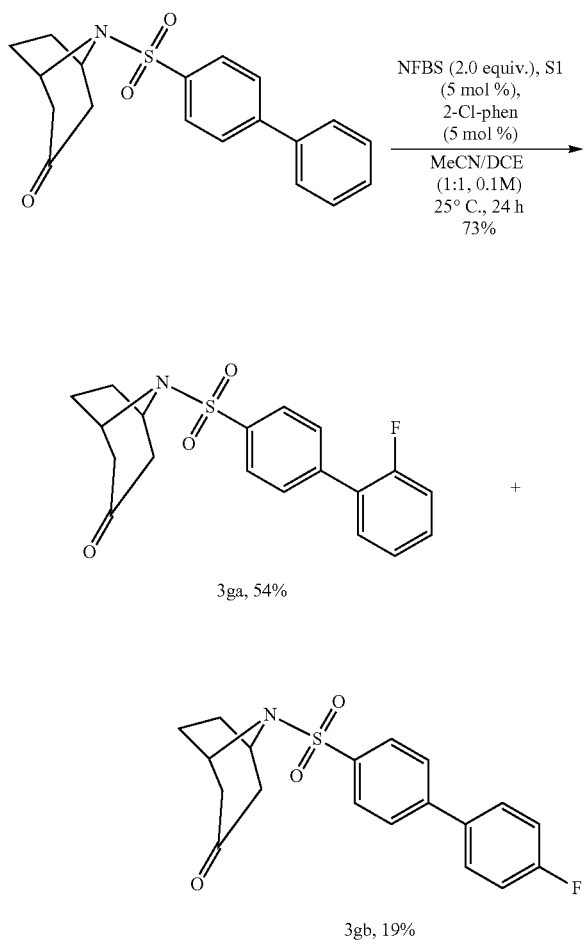

3ga, 54%

3gb, 19%

A mixture of palladium complex S1 (27.7 mg, 50.0 μmol, 5.00 mol %) and 2-chloro-phenanthroline (10.7 mg, 50.0 μmol, 5.00 mol %.) was dissolved in acetonitrile (5.0 mL). This mixture was added to a 20 mL vial containing a solution of NFBS (615 mg, 2.00 mmol, 2.00 equiv.) and 8-(biphenyl-4-ylsulfonyl)-8-azabicyclo[3.2.1]octan-3-one (341 mg, 1.0 mmol, 1.0 equiv.) in dichloroethane (5.0 mL, final c=0.10 M). The reaction mixture was stirred for 25 hours at 25° C. The remaining oxidant was quenched by adding a solution of $Na_2S_2O_3(H_2O)_5$ (1.22 g, 5.00 mmol, 5.00 equiv.) in water (20 mL) and stirring for 30 min. The aqueous layer was extracted with dichloromethane (3×50 mL). The combined organic layers were dried over sodium sulfate, filtered, and concentrated in vacuo at 40° C. to afford a pale yellow solid. The residue was dissolved in dichloromethane (2 mL), loaded onto a short plug of silica (20 g) and eluted with ethyl acetate. and concentrated in vacuo to afford a colorless solid (312 mg) containing the title compounds (262 mg, 0.729 mmol 73% yield, 3ga: 3gb (74:26)), 8-(biphenyl-4-ylsulfonyl)-8-azabicyclo[3.2.1]octan-3-one and minor inseparable impurities. The yield and selectivity were determined by $^{19}F$ using 1,4-bis(trifluoromethyl)benzene as an internal standard (standard: δ −63.4 ppm, 6 F; compared with product peaks at δ −113.2 and −117.5 ppm; first relaxation time of 10 s to ensure accurate integration). Purification by HPLC (MultoKrom Si, 3 μm, 20 mm×250 mm, isohexane:isopropanol 95:5, 20 mL/min, 8.9 MPa, 308 K, 220 nm UV) provided purified product isomers, yielding the title compound 3ga (83% pure by HPLC, retention time 12.9 min.) and a second fraction enriched with 3gb relative to the unpurified material (43% 3gb by HPLC, 65:35 ratio with 3ga by $^{19}F$ NMR, retention time 15.5 min.). The relevant signals of the spectra matched the corresponding signals of spectra reported for a 4'-fluoro-4-sulfonamide biphenyl and a 2'-fluoro-4-sulfonamide biphenyl motifs. See 2'-fluoro-4-sulfonamide biphenyl, similar to 5ka3ga: De Brabander, J; Shay, J. W.; Wang, W. Therapeutics Targeting Truncated Adenomatous Polyposis Coli (APC) Proteins. US Patent US2015232444, Aug. 20, 2015; 4'-fluoro-4-sulfonamide biphenyl, similar to 5 kb3gb: Urlam, M. K.; Pireddu, R.; Ge, Y; Zhang, X.; Sun, Y; Lawrence, H. R.; Guida, W. C.; Sebti, S. M.; Lawrence, N. J. Med Chem Comm 2013, 4, 932-941. $R_f$=0.40 (ethyl acetate/dichloromethane, 10:90 (v/v)). HRMS-FIA(m/z) calculated for $C_{19}H_{18}FNO_3$ SNa [M+Na]⁺, 382.0884; found, 382.0887.

NMR Spectroscopy: 8-((2'-fluoro-biphenyl-4-yl)sulfonyl)-8-azabicyclo[3.2.1]octan-3-one (3ga): $^1H$ NMR (500 MHz, CDCl₃, 23° C., δ): 7.98 (d, J=8.5 Hz, 2H), 7.70 (d, J=8.5 Hz, 2H), 7.51-7.36 (m, 2H), 7.30-7.22 (m, 1H), 7.19 (dd, J=10.9, 8.2 Hz, 1H), 4.60-4.50 (m, 1H), 2.83 (dd, J=16.5, 4.5 Hz, 2H), 2.47-2.31 (m, 2H), 1.87-1.70 (m, 2H), 1.63 (d, J=7.8 Hz, 2H) ppm. $^{13}C$ NMR (125 MHz, CDCl₃, 23° C., δ): 206.9, 159.8 (d, J=249.2 Hz), 141.0, 138.9, 130.7 (d, J=2.9 Hz), 130.5 (d, J=8.4 Hz), 130.0 (d, J=3.4 Hz), 129.3, 128.8, 128.0, 127.5, 124.9 (d, J=3.6 Hz), 116.6 (d, J=22.6 Hz), 56.3, 50.4, 29.6. ppm. $^{19}F$ NMR (470 MHz, CDCl₃, 23° C., δ): −117.5 ppm. 8-((4'-fluoro-biphenyl-4-yl)sulfonyl)-8-azabicyclo[3.2.1]octan-3-one (3gb): $^1H$ NMR (500 MHz, CDCl₃, 23° C., δ): 7.97 (d, J=8.4 Hz, 2H), 7.69 (d, J=8.5 Hz, 2H), 7.58 (dd, J=8.8, 5.2 Hz, 2H), 7.18 (t, J=8.6 Hz, 2H), 4.63-4.45 (m, 2H), 2.83 (d, J=16.4 Hz, 2H), 2.54-2.14 (m, 2H), 1.91-1.70 (m, 2H), 1.63 (d, J=7.8 Hz, 2H). $^{13}C$ NMR (125 MHz, CDCl₃, 23° C., δ): 206.8, 163.4 (d, J=248.6 Hz), 145.2, 138.6, 129.2 (d, J=8.2 Hz), 128.0, 127.8, 127.6, 116.3 (d, J=21.5 Hz), 56.2, 50.4, 29.6. ppm. $^{19}F$ NMR (470 MHz, CDCl₃, 23° C., δ): −113.2 ppm.

Reaction without Catalyst:

Under $N_2$ atmosphere, an oven-dried 4 mL vial was charged with Selectfluor (71 mg, 200 μmol, 2.0 equiv.) and 8-(biphenyl-4-ylsulfonyl)-8-azabicyclo[3.2.1]octan-3-one (34.1 mg, 100 μmol, 1.0 equiv.) in acetonitrile (1.0 mL, c=0.10 M). The resulting reaction mixture was stirred at 80° C. for 24 h. After cooling to room temperature, 1,4-bistrifluoromethylbenzene (3.6 mg, 2.6 μl, 17 μmol, 0.17 equiv.) was added to the reaction mixture, stirred and a sample (approx. 0.1 mL) was diluted with CD₃CN (0.5 mL) and the yield of the title products was determined by $^{19}F$ NMR using 1,4-bis(trifluoromethyl)benzene as an internal standard to be 27% (standard: δ −63.4 ppm, 6 F; compared with product peaks at δ −113.2 and −117.5 ppm; first relaxation time of 10 s to ensure accurate integration) to be 18% (3ga:3gb (84:16)) and 109% of 2 new, unidentified fluorine peaks at δ −175.9 ppm (23%) and −178.8 ppm (86%) most likely derived from α-fluorination of the ketone (based on fluoride integration relative to the standard; the percentage does not necessarily correlate to a yield of product because it does not correct for difluoro- or poly-fluoro products).

Example 9. Ethyl trans-2-(2-fluorophenyl)cyclopropane-1-carboxylate (3ha) and ethyl trans-2-(4-fluorophenyl)cyclopropane-1-carboxylate (3hb)

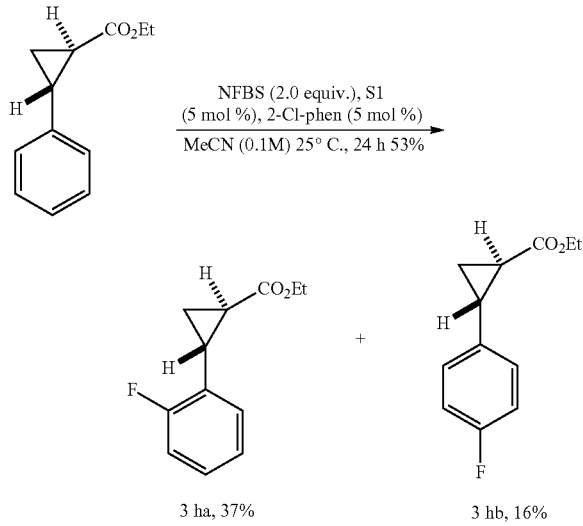

3 ha, 37%   3 hb, 16%

A mixture of palladium complex S1 (27.7 mg, 50.0 μmol, 5.00 mol %) and 2-chloro-phenanthroline (10.7 mg, 50.0 μmol, 5.00 mol %.) was dissolved in acetonitrile (5.0 mL). This mixture was added to a 20 mL vial containing a solution of NFBS (615 mg, 2.00 mmol, 2.00 equiv.) and racemic ethyl trans-2-phenylcyclopropane-1-carboxylate (190 mg, 1.0 mmol, 1.0 equiv.) in acetonitrile (5.0 mL, final c=0.10 M). The reaction mixture was stirred for 20 hours at 25° C. The remaining oxidant was quenched by adding a solution of $Na_2S_2O_3(H_2O)_5$ (1.22 g, 5.00 mmol, 5.00 equiv.) in water (20 mL) and stirring for 30 min. The mixture was added to a separatory funnel with 50 mL dichloromethane. The aqueous layer was extracted with dichloromethane (3×50 mL). The combined organic layers were dried over sodium sulfate, filtered, and concentrated in vacuo at 40° C. to afford a pale yellow solid. The residue was dissolved in dichloromethane (2 mL), loaded onto a short plug of silica (20 g) and eluted with dichloromethane/pentane 30:70 (v/v). and concentrated in vacuo to afford a colorless solid (147 mg) containing the title compounds (110 mg, 0.53 mmol, 53% yield, 3ha:3hb (70:30)), ethyl trans-2-phenylcyclopropane-1-carboxylate and minor inseparable impurities The yield and selectivity were determined by $^{19}F$ using 1,4-bis(trifluoromethyl)benzene as an internal standard (standard: δ −63.4 ppm, 6 F; compared with product peaks at δ −116.4 and −118.8 ppm; first relaxation time of 10 s to ensure accurate integration). The spectra matched the reported spectra for the title compounds. See WIPO patent, WO2007025144; Pryde et al., *Bioorg. Med. Chem.* 2007, 15, 142-159. $R_f$=0.70 (dichloromethane). HRMS-FIA(m/z) calculated for $C_{12}H_{13}FO_2Na$ [M+Na]$^+$, 231.0792; found, 231.0792.

NMR Spectroscopy: Ethyl trans-2-(2-fluorophenyl)cyclopropane-1-carboxylate (3ha): $^1H$ NMR (500 MHz, CDCl$_3$, 23° C., δ): 7.31-6.99 (m, 4H), 4.17 (q, J=7.0 Hz, 2H), 2.55-2.44 (m, 1H), 1.84 (ddd, J=8.4, 5.2, 4.2 Hz, 1H), 1.62-1.55 (m, 1H), 1.28 (t, J=7.2 Hz, 3H) ppm. $^{13}C$ NMR (125 MHz, CDCl$_3$, 23° C., δ): 173.4, 161.7 (d, J=244.9 Hz), 127.9 (d, J=8.1 Hz), 127.2 (d, J=14.0 Hz), 127.1 (d, J=4.0 Hz) 124.1 (d, J=3.5 Hz), 115.4 (d, J=21.4 Hz), 60.9, 25.6, 20.0 (d, J=4.8 Hz), 15.8 (d, J=1.0 Hz), 14.4 ppm. $^{19}F$ NMR (470 MHz, CDCl$_3$, 23° C., δ): −116.4 ppm. Ethyl trans-2-(4-fluorophenyl)cyclopropane-1-carboxylate (3hb): $^1H$ NMR (500 MHz, CDCl$_3$, 23° C., δ): 7.30-6.99 (m, 1H), 4.23-4.13 (m, 1H), 2.66 (ddd, J=9.4, 6.6, 4.3 Hz, 1H), 1.96-1.91 (m, 1H), 1.65-1.53 (m, 1H), 1.28 (t, J=7.2 Hz, 3H). $^{13}C$ NMR (125 MHz, CDCl$_3$, 23° C., δ): 173.6, 161.8 (d, J=246.3 Hz), 135.9 (d, J=3.2 Hz), 128.0 (d, J=8.3 Hz), 115.5 (d, J=22.0 Hz), 60.8, 26.3, 24.3, 24.1, 22.9, 17.2, 17.0. ppm. $^{19}F$ NMR (470 MHz, CDCl$_3$, 23° C., δ): −118.8 ppm.

Reactions without Catalyst

Under N$_2$ atmosphere, an oven-dried 4 mL vial was charged with Selectfluor (71 mg, 200 μmol, 2.0 equiv.) and ethyl trans-2-phenylcyclopropane-1-carboxylate (19.0 mg, 100 μmol, 1.0 equiv.) in acetonitrile (1.0 mL, c=0.10 M). The resulting reaction mixture was stirred at 80° C. for 24 h. After cooling to room temperature, 1,4-bistrifluoromethylbenzene (3.6 mg, 2.6 μl, 17 μmol, 0.17 equiv.) was added to the reaction mixture, stirred and a sample (approx. 0.1 mL) was diluted with CD$_3$CN (0.5 mL) and the yield of the title products was determined by $^{19}F$ NMR using 1,4-bis(trifluoromethyl)benzene as an internal standard to be <1%.

Example 10. 5-(2-Fluorophenyl)pyrimidine (3ia) and 5-(4-fluorophenyl)pyrimidine (3ib)

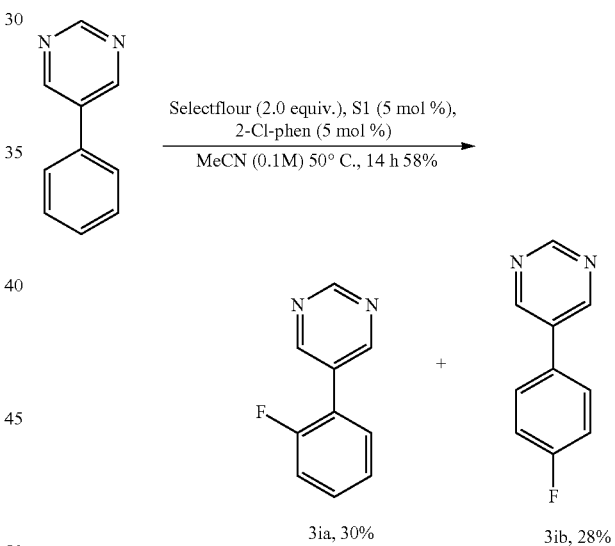

3ia, 30%   3ib, 28%

A mixture of palladium complex S1 (27.7 mg, 50.0 μmol, 5.00 mol %) and 2-chloro-phenanthroline (10.7 mg, 50.0 μmol, 5.00 mol %.) was dissolved in acetonitrile (5.0 mL). This mixture was added to a 20 mL vial containing a solution of Selectfluor (709 mg, 2.00 mmol, 2.00 equiv.) and 5-phenylpyrimidine (156 mg, 1.0 mmol, 1.0 equiv.) in acetonitrile (5.0 mL, final c=0.10 M). The reaction mixture was stirred for 14 hours at 50° C. and then transferred to a separatory funnel. Ethyl acetate (50 mL) was added and the organic layer was washed with water (50 mL) with brine added (10 mL). The aqueous layer was extracted with dichloromethane (3×50 mL). The combined organic layers were dried over sodium sulfate, filtered, and concentrated in vacuo at 40° C. to afford a pale yellow solid. The residue was dissolved in dichloromethane (2 mL), loaded onto a short plug of silica (20 g) and eluted with ethyl acetate/dichloromethane 20:80

(v/v) and concentrated in vacuo to afford a yellow-orange solid (123 mg) containing the title compounds (111 mg, 0.580, 58% yield, 3ia:3ib (52:48)), 5-phenylpyrimidine and minor inseparable impurities. The yield and selectivity were determined by $^{19}$F using 1,4-bis(trifluoromethyl)benzene as an internal standard (standard: δ −63.4 ppm, 6 F; compared with product peaks at δ −112.4 and −117.5 ppm; first relaxation time of 10 s to ensure accurate integration). The spectra matched the reported spectra for the title compound 5ib. See Liu et al., *Chem. Commun.*, 2009, 6267-6269. $R_f$=0.45 (ethyl acetate/dichloromethane 20:80 (v/v)). HRMS-FIA(m/z) calculated for $C_{10}H_8FN_2$ [M+H]+, 175.0666; found, 175.0667.

NMR Spectroscopy: $^{13}$C NMR (125 MHz, CDCl$_3$, 23° C., δ): 163.5 (d, J=249.7 Hz), 159.9 (d, J=249.7 Hz), 157.7, 157.6, 157.6, 156.4 (d, J=4.1 Hz), 155.0, 154.8, 134.4 (d, J=8.3 Hz), 131.1 (d, J=8.3 Hz), 130.2 (d, J=2.9 Hz), 129.8 (d, J=1.8 Hz), 129.5, 129.1, 128.9 (d, J=8.4 Hz), 127.1, 125.2, 125.1, 116.7 (d, J=21.8 Hz), 116.6 (d, J=22.0 Hz). 5-(2-fluorophenyl)pyrimidine (3ia): $^1$H NMR (500 MHz, CDCl$_3$, 23° C., δ): 9.15 (s, 1H), 8.91-8.84 (m, 3H), 7.55-7.33 (m, 4H), 7.27-7.10 (m, 3H). $^{19}$F NMR (470 MHz, CDCl$_3$, 23° C., δ): −117.5 ppm. 5-(4-fluorophenyl)pyrimidine (3ib): $^1$H NMR (500 MHz, CDCl$_3$, 23° C., δ): 9.21 (d, J=1.2 Hz, 1H), 8.96 (s, 1H), 8.92 (s, 1H), 7.62-7.51 (m, 3H), 7.50-7.44 (m, 1H), 7.22 (t, J=8.6 Hz, 1H). $^{19}$F NMR (500 MHz, CDCl$_3$, 23° C., δ): −112.4 ppm.

Reactions without Catalyst

Under N$_2$ atmosphere, an oven-dried 4 mL vial was charged with Selectfluor (71 mg, 200 μmol, 2.0 equiv.) and 5-phenylpyrimidine (15.6 mg, 100 μmol, 1.0 equiv.) in acetonitrile (1.0 mL, c=0.10 M). The resulting reaction mixture was stirred at 80° C. for 24 h. After cooling to room temperature, 1,4-bistrifluoromethylbenzene (3.6 mg, 2.6 μl, 17 μmol, 0.17 equiv.) was added to the reaction mixture, stirred and a sample (approx. 0.1 mL) was diluted with CD$_3$CN (0.5 mL) and the yield of the title products was determined by $^{19}$F NMR using 1,4-bis(trifluoromethyl)benzene as an internal standard to be 2%.

Example 11. 5-(2-Fluorophenyl)pyridine (3ja) and 5-(4-fluorophenyl)pyrimidine (3jb)

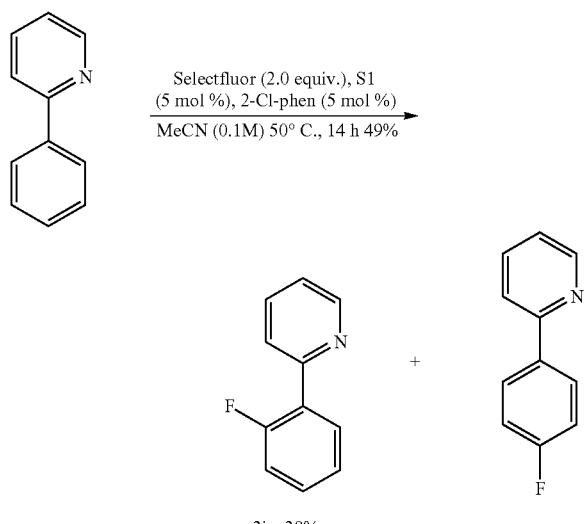

3ja, 38%    3jb, 11%

A mixture of palladium complex S1 (27.7 mg, 50.0 μmol, 5.00 mol %) and 2-chloro-phenanthroline (10.7 mg, 50.0 μmol, 5.00 mol %.) was dissolved in acetonitrile (5.0 mL). This mixture was added to a 20 mL vial containing a solution of Selectfluor (709 mg, 2.00 mmol, 2.00 equiv.) and 2-phenylpyridine (155 mg, 143 μl, 1.0 mmol, 1.0 equiv.) in acetonitrile (5.0 mL, final c=0.10 M). The reaction mixture was stirred for 14 hours at 50° C. and then transferred to a separatory funnel. Dichloromethane (50 mL) was added and the organic layer was washed with water (50 mL) with brine added (10 mL). The aqueous layer was extracted with dichloromethane (3×50 mL). The combined organic layers were dried over sodium sulfate, filtered, and concentrated in vacuo at 40° C. to afford a pale yellow solid. The residue was dissolved in dichloromethane (2 mL), loaded onto a short plug of silica (20 g) and eluted with 0.35 ethyl acetate/dichloromethane 30/70 (v/v), and concentrated in vacuo to afford a yellow oil (110 mg) containing the title compounds (85 mg, 0.49 mmol, 49% yield, 3ja:3jb (70:30)), 2-phenylpyridine, minor inseparable impurities and dichloromethane. The yield and selectivity were determined by $^{19}$F using 1,4-bis(trifluoromethyl)benzene as an internal standard (standard: δ −63.4 ppm, 6 F; compared with product peaks at δ −113.4 and −117.7 ppm for the neutral pyridine; first relaxation time of 10 s to ensure accurate integration). Purification by HPLC (Kromasil-5 C18, 5 μm, 30 mm×150 mm, MeCN:H$_2$O 35:65, 42.5 mL/min, 11.4 MPa, 293 K, 254 nm UV) provided purified product isomers 3ja (>99% pure by HPLC, retention time 15.3 min.) and 3jb (>99% pure by HPLC, retention time 18.3 min.). To decrease the volatility of the products, before concentrating the HPLC fractions were treated with excess trifluoroacetic acid, yielding the trifluoroacetic acid salt of the title compounds 3ja TFA and 3jb TFA as colorless solids. The spectra of the unpurified mixture matched the reported spectra for the title compounds. See Yu et al., *Org. Lett.*, 2013, 15, 940-943. Wu et al., *Chem. Commun.*, 2015, 51, 2286-2289. $R_f$=0.35 (ethyl acetate/dichloromethane 30/70 (v/v)). HRMS-ESI (m/z) calculated for $C_{11}H_9FN$ [M+H]$^+$, 174.0714; found 174.0714.

NMR Spectroscopy: 2-(2-fluorophenyl)pyridine (3ja TFA): $^1$H NMR (500 MHz, CDCl$_3$, 23° C., δ): 14.46 (br s), 9.07 (d, J=5.4 Hz, 1H), 8.42 (t, J=7.9 Hz, 1H), 8.11 (d, J=8.0 Hz, 1H), 7.87 (t, J=6.3 Hz, 1H), 7.79 (t, J=7.9 Hz, 1H), 7.62 (td, J=7.9, 5.5 Hz, 1H), 7.41 (t, J=7.5 Hz, 1H), 7.31 (dd, J=10.8, 8.4 Hz, 1H) ppm. $^{13}$C NMR (125 MHz, CDCl$_3$, 23° C., δ): 159.9 (d, J=253.8 Hz), 149.4, 144.7, 143.6, 134.6 (d, J=8.9 Hz), 130.9, 127.9 (d, J=6.5 Hz), 125.8 (d, J=3.7 Hz), 125.2, 119.6 (d, J=11.7 Hz), 117.1 (d, J=21.5 Hz) ppm. $^{19}$F NMR (470 MHz, CDCl$_3$, 23° C., δ): −75.8, −116.4 ppm. 2-(4-fluorophenyl)pyridine (3jb TFA): $^1$H NMR (500 MHz, CDCl$_3$, 23° C., δ): δ 15.56 (s, 1H), 9.02 (dd, J=5.7, 1.7 Hz, 1H), 8.31 (td, J=7.9, 1.4 Hz, 1H), 7.96 (dd, J=8.2, 1.1 Hz, 1H), 7.94-7.89 (m, 1H), 7.74 (ddd, J=7.2, 5.7, 1.2 Hz, 1H), 7.29 (t, J=8.5 Hz, 1H) ppm. $^{13}$C NMR (125 MHz, CDCl$_3$, 23° C., δ): δ 165.2 (d, J=254.8 Hz), 161.7, 153.7, 144.2, 144.0, 130.6 (d, J=9.3 Hz), 128.5 (d, J=3.5 Hz), 124.6, 124.3, 117.2 (d, J=22.4 Hz). ppm. $^{19}$F NMR (470 MHz, CDCl$_3$, 23° C., δ): −75.8, −106.8 ppm.

Reactions without Catalyst

Under N$_2$ atmosphere, an oven-dried 4 mL vial was charged with Selectfluor (71 mg, 200 μmol, 2.0 equiv.) and 2-phenylpyridine (15.6 mg, 100 μmol, 1.0 equiv.) in acetonitrile (1.0 mL, c=0.10 M). The resulting reaction mixture was stirred at 80° C. for 24 h. After cooling to room temperature, 1,4-bistrifluoromethylbenzene (3.6 mg, 2.6 μl, 17 μmol, 0.17 equiv.) was added to the reaction mixture, stirred and a sample (approx. 0.1 mL) was diluted with CD$_3$CN (0.5 mL)

and the yield of the title products was determined by $^{19}$F NMR using 1,4-bis(trifluoromethyl)benzene as an internal standard to be <1%.

Example 12. Ethyl (2-fluorophenyl) nateglinide derivative (3ka) and ethyl (4-fluorophenyl) nateglinide Derivative (3kb)

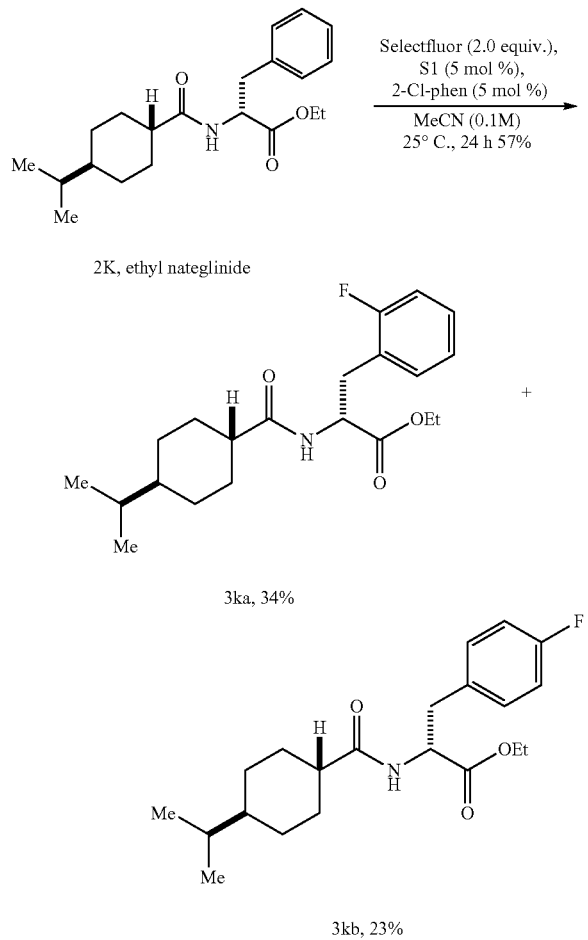

A mixture of palladium complex S1 (27.7 mg, 50.0 µmol, 5.00 mol %) and 2-chloro-phenanthroline (10.7 mg, 50.0 µmol, 5.00 mol %.) was dissolved in acetonitrile (5.0 mL). This mixture was added to a 20 mL vial containing a solution of Selectfluor (709 mg, 2.00 mmol, 2.00 equiv.) and ethyl nateglinide (2k, ethyl (trans-4-isopropylcyclohexane-1-carbonyl)-D-phenylalaninate) (233 mg, 1.0 mmol, 1.0 equiv.) in acetonitrile (5.0 mL, final c=0.10 M). The reaction mixture was stirred for 24 hours at 0° C. and then transferred to a separatory funnel. Dichloromethane (50 mL) was added and the organic layer was washed with water (50 mL) with brine added (10 mL). The aqueous layer was extracted with dichloromethane (3×50 mL). The combined organic layers were dried over sodium sulfate, filtered, and concentrated in vacuo at 40° C. to afford a pale yellow solid. The residue was dissolved in dichloromethane (2 mL), loaded onto a short plug of silica (20 g) and eluted with ethyl acetate/dichloromethane 50:50 (v/v). and concentrated in vacuo to afford a colorless solid (265 mg) containing the title compounds (207 mg, 0.572 mmol, 57% yield, 3ka:3kb (60:40)), ethyl nateglinide and minor inseparable impurities. The yield and selectivity were determined by $^{19}$F using 1,4-bis(trifluoromethyl)benzene as an internal standard (standard: δ −63.4 ppm, 6 F; compared with product peaks at δ −115.8 and −117.3 ppm; first relaxation time of 10 s to ensure accurate integration). Purification by HPLC (MultoKrom Si, 3 µm, 20 mm×250 mm, isohexane:isopropanol 99:1, 15 mL/min, 7.9 MPa, 308 K, 220 nm UV) provided purified product isomers, yielding the title compound 2ka (92% pure by HPLC, retention time 15.3 min.) and 2kb (97% pure by HPLC, retention time 18.1 min.). The spectra were comparable to the reported spectra for the corresponding acids of the title compounds. See US Patent: US2015045435. $R_f$=0.55 (ethyl acetate/dichloromethane 50:50 (v/v)). HRMS-ESI (m/z) calculated for $C_{21}H_{30}FNO_3Na$ [M+Na]$^+$, 386.2102; found, 386.2106.

NMR Spectroscopy: Ethyl (R)-3-(2-fluorophenyl)-2-((trans-4-isopropylcyclohexane-1-carboxamido)propanoate (3pa): $^1$H NMR (500 MHz, CDCl$_3$, 23° C., δ): 7.25-7.19 (m, 1H), 7.13 (td, J=7.5, 1.9 Hz, 1H), 7.06 (td, J=7.5, 1.2 Hz, 1H), 7.01 (ddd, J=9.6, 8.2, 1.2 Hz, 1H), 5.96 (d, J=7.8 Hz, 1H), 4.84 (dt, J=7.8, 6.1 Hz, 1H), 4.18 (qd, J=7.2, 4.3 Hz, 2H), 3.26-3.09 (m, 2H), 1.99 (tt, J=12.2, 3.6 Hz, 1H), 1.93-1.81 (m, 2H), 1.81-1.72 (m, 2H), 1.44-1.30 (m, 3H), 1.25 (t, J=7.2 Hz, 3H), 1.13-0.90 (m, 3H), 0.85 (d, J=6.8 Hz, 6H) ppm. $^{13}$C NMR (125 MHz, CDCl$_3$, 23° C., δ): 175.7, 171.8, 161.5 (d, J=245.0 Hz), 132.0 (d, J=4.7 Hz), 129.0 (d, J=8.3 Hz), 124.2 (d, J=3.5 Hz), 123.3 (d, J=16.0 Hz), 115.4 (d, J=22.1 Hz), 61.8, 52.3, 45.6, 43.4, 32.9, 31.6, 29.8, 29.6, 29.1, 29.1, 19.9, 14.2 ppm. $^{19}$F NMR (470 MHz, CDCl$_3$, 23° C., δ): −117.3 ppm. Ethyl (R)-3-(2-fluorophenyl)-2-((trans-4-isopropylcyclohexane-1-carboxamido)propanoate (5pb): $^1$H NMR (500 MHz, CDCl$_3$, 23° C., δ): 7.05 (dd, J=8.6, 5.5 Hz, 2H), 6.97 (t, J=8.6 Hz, 2H), 5.89 (d, J=7.6 Hz, 1H), 4.83 (dt, J=7.7, 5.7 Hz, 1H), 4.18 (qd, J=7.1, 1.5 Hz, 2H), 3.22-2.98 (m, 2H), 2.01 (tt, J=12.2, 3.5 Hz, 1H), 1.93-1.82 (m, 2H), 1.78 (dtd, J=11.2, 3.7, 1.9 Hz, 3H), 1.48-1.32 (m, 4H), 1.26 (t, J=7.2 Hz, 3H), 1.10-0.91 (m, 2H), 0.85 (d, J=6.8 Hz, 6H) ppm. $^{13}$C NMR (125 MHz, CDCl$_3$, 23° C., δ): 175.7, 171.8, 162.1 (d, J=245.1 Hz), 131.9 (d, J=3.1 Hz), 131.0 (d, J=7.9 Hz), 115.4 (d, J=21.4 Hz), 61.7, 52.9, 45.7, 43.4, 37.3, 32.9, 30.0, 29.7, 29.1, 29.1, 19.9, 14.3 ppm. $^{19}$F NMR (470 MHz, CDCl$_3$, 23° C., δ):): −115.8 ppm.

Reactions without Catalyst

Under N$_2$ atmosphere, an oven-dried 4 mL vial was charged with Selectfluor (71 mg, 200 µmol, 2.0 equiv.) and ethyl nateglinide (4p, ethyl (trans-4-isopropylcyclohexane-1-carbonyl)-D-phenylalaninate) (34.5 mg, 100 µmol, 1.0 equiv.) in acetonitrile (1.0 mL, c=0.10 M). The resulting reaction mixture was stirred at 80° C. for 24 h. After cooling to room temperature, 1,4-bistrifluoromethylbenzene (3.6 mg, 2.6 µl, 17 µmol, 0.17 equiv.) was added to the reaction mixture, stirred and a sample (approx. 0.1 mL) was diluted with CD$_3$CN (0.5 mL) and the yield of the title products was determined by $^{19}$F NMR using 1,4-bis(trifluoromethyl)benzene as an internal standard (standard: δ −63.4 ppm, 6 F; compared with product peaks at δ −115.8 and −117.3 ppm; first relaxation time of 10 s to ensure accurate integration) to be 11% (3pa:3pb (80:20)).

Example 13. Trans-2-(4-fluorophenyl)cyclohexanol (3la) and trans-2-(4-fluorophenyl)cyclohexanol (3lb)

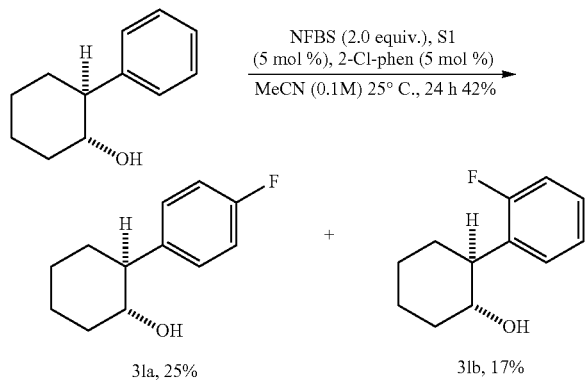

3la, 25%    3lb, 17%

A mixture of palladium complex S1 (27.7 mg, 50.0 µmol, 5.00 mol %) and 2-chloro-phenanthroline (10.7 mg, 50.0 µmol, 5.00 mol %.) was dissolved in acetonitrile (5.0 mL). This mixture was added to a 20 mL vial containing a solution of NFBS (615 mg, 2.00 mmol, 2.00 equiv.) and trans-2-phenylcyclohexanol (176 mg, 1.0 mmol, 1.0 equiv.) in acetonitrile (5.0 mL, final c=0.10 M). The reaction mixture was stirred for 24 hours at 25° C. The remaining oxidant was quenched by adding a solution of $Na_2S_2O_3 \cdot (H_2O)_5$ (1.22 g, 5.00 mmol, 5.00 equiv.) in water (20 mL) and stirring for 30 min. The mixture was added to a separatory funnel with 50 mL dichloromethane. The aqueous layer was extracted with dichloromethane (3×50 mL). The combined organic layers were dried over sodium sulfate, filtered, and concentrated in vacuo at 40° C. to afford a pale yellow solid. The residue was dissolved in dichloromethane (2 mL), loaded onto a short plug of silica (20 g) and eluted with dichloromethane/pentane 50:50 (v/v). and concentrated in vacuo to afford a colorless solid (98 mg) containing the title compounds (81.5 mg, 0.421 mmol, 42% yield, 3la:3lb (59:41)), trans-2-phenylcyclohexanol and minor inseparable impurities. The yield and selectivity were determined by $^{19}F$ using 1,4-bis(trifluoromethyl)benzene as an internal standard ((standard: δ −63.4 ppm, 6 F; compared with product peaks at δ −116.8 and −118.8 ppm; first relaxation time of 10 s to ensure accurate integration). Purification by HPLC (MultoKrom Si, 3 µm, 20 mm×250 mm, isohexane:isopropanol 99:1, 15 mL/min, 8.3 MPa, 308 K, 220 nm UV) provided purified product isomers, yielding the title compound 3la (82% pure by HPLC, retention time 15.8 min.) and 3lb (87% pure by HPLC, retention time 16.5 min.). The spectra matched the reported spectra for the title compound 3la. See Powell et al., *J Am. Chem. Soc.*, 2005, 127, 510. $R_f$=0.40 (dichloromethane/pentane, 50:50 (v/v)). HRMS-FIA(m/z) calculated for $C_{12}H_{15}FONa$ [M+Na]$^+$, 217.0999; found, 217.0998, NMR Spectroscopy: Trans-2-(4-fluorophenyl)cyclohexanol (3la): $^1H$ NMR (500 MHz, CDCl$_3$, 23° C., δ): 7.22 (dd, J=8.6, 5.5 Hz, 1H), 7.02 (t, J=8.7 Hz, 1H), 3.61 (td, J=10.1, 4.3 Hz, 1H), 2.42 (ddd, J=12.3, 9.9, 3.6 Hz, 1H), 2.19-2.08 (m, 1H), 2.00-1.80 (m, 1H), 1.81-1.72 (m, 1H), 1.58-1.18 (m, 3H) ppm. $^{13}C$ NMR (125 MHz, CDCl$_3$, 23° C., δ): 161.9 (d, J=244.8 Hz), 139.1 (d, J=3.0 Hz), 129.4 (d, J=7.7 Hz), 115.7 (d, J=20.9 Hz), 74.7, 52.6, 34.7, 33.6, 26.2, 25.2. ppm. $^{19}F$ NMR (470 MHz, CDCl$_3$, 23° C., δ): −116.8 ppm. Trans-2-(2-fluorophenyl)cyclohexanol (3lb): $^1H$ NMR (500 MHz, CDCl$_3$, 23° C., δ): 7.28 (td, J=7.5, 1.9 Hz, 1H), 7.20 (tdd, J=7.2, 4.9, 1.9 Hz, 1H), 7.12 (td, J=7.5, 1.3 Hz, 1H), 7.04 (ddd, J=9.7, 8.1, 1.3 Hz, 1H), 3.79 (td, J=10.1, 4.4 Hz, 1H), 2.83 (ddd, J=12.4, 10.1, 3.6 Hz, 1H), 2.17-2.10 (m, 1H), 1.94-1.81 (m, 2H), 1.81-1.69 (m, 1H), 1.66-1.18 (m, 4H), 0.93-0.79 (m, 1H) ppm. $^{13}C$ NMR (125 MHz, CDCl$_3$, 23° C., δ): 161.5 (d, J=245.0 Hz), 130.3 (d, J=14.4 Hz), 128.7 (d, J=5.1 Hz), 128.1 (d, J=8.4 Hz), 124.5 (d, J=3.4 Hz), 115.9 (d, J=23.2 Hz), 73.5, 46.2, 35.3, 32.5, 26.1, 25.2 ppm. $^{19}F$ NMR (470 MHz, CDCl$_3$, 23° C., δ): −118.8 ppm.

Reactions without Catalyst

Under $N_2$ atmosphere, an oven-dried 4 mL vial was charged with Selectfluor (71 mg, 200 µmol, 2.0 equiv.) and trans-2-phenylcyclohexanol (17.6 mg, 100 µmol, 1.0 equiv.) in acetonitrile (1.0 mL, c=0.10 M). The resulting reaction mixture was stirred at 80° C. for 24 h. After cooling to room temperature, 1,4-bistrifluoromethylbenzene (3.6 mg, 2.6 µl, 17 µmol, 0.17 equiv.) was added to the reaction mixture, stirred and a sample (approx. 0.1 mL) was diluted with CD$_3$CN (0.5 mL) and the yield of the title products was determined by $^{19}F$ NMR using 1,4-bis(trifluoromethyl)benzene as an internal standard to be <3%.

Example 14. 4-(4-Fluorophenyl)cyclohexanone (3ma) and 4-(2-fluorophenyl)cyclohexanone (3mb)

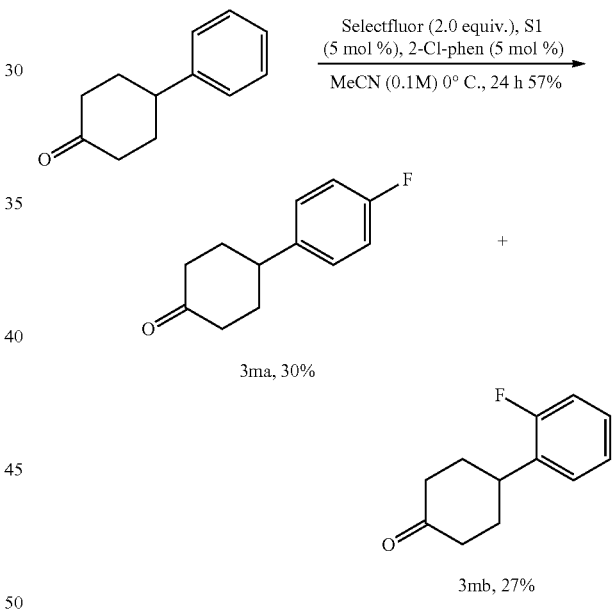

3ma, 30%

3mb, 27%

A mixture of palladium complex S1 (27.7 mg, 50.0 µmol, 5.00 mol %) and 2-chloro-phenanthroline (10.7 mg, 50.0 µmol, 5.00 mol %.) was dissolved in acetonitrile (5.0 mL). This mixture was added to a 20 mL vial containing a solution of Selectfluor (709 mg, 2.00 mmol, 2.00 equiv.) and 4-phenylcyclohexanone (174 mg, 1.0 mmol, 1.0 equiv.) in acetonitrile (5.0 mL, final c=0.10 M). The reaction mixture was stirred for 24 hours at 0° C. and then transferred to a separatory funnel. Dichloromethane (50 mL) was added and the organic layer was washed with water (50 mL) with brine added (10 mL). The aqueous layer was extracted with dichloromethane (3×50 mL). The combined organic layers were dried over sodium sulfate, filtered, and concentrated in vacuo at 40° C. to afford a pale yellow solid. The residue was dissolved in dichloromethane (2 mL), loaded onto a short plug of silica (20 g) and eluted with ethyl acetate. and concentrated in vacuo to afford a colorless solid (132 mg) containing the title compounds (109 mg, 0.57 mmol, 57% yield, 3ma:3mb (60:40)), 4-phenylcyclohexanone and minor inseparable impurities. The yield and selectivity were determined by and $^{19}$F using 1,4-bis(trifluoromethyl)benzene as an internal standard (standard: δ −63.4 ppm, 6 F; compared with product peaks at δ −116.5 and −119.0 ppm; first relaxation time of 10 s to ensure accurate integration). The spectra matched the reported spectra for the title compounds. See Müller et al, *J. Am. Chem. Soc.* 2011, 133, 18534-18537. U.S. Pat. No. 6,037,354. $R_f$=0.40 (dichloromethane:pentane, 40:60 (v/v)). HRMS-ESI (m/z) calculated for $C_{12}H_{13}FONa$ [M+Na]$^+$, 215.0843; found, 215.0844.

NMR Spectroscopy: 4-(4-fluorophenyl)cyclohexanone (3ma): $^1$H NMR (500 MHz, CDCl$_3$, 23° C., δ): 7.25-7.17 (m, 2H), 7.01 (t, J=8.7 Hz, 2H), 3.02 (tt, J=12.1, 3.4 Hz, 1H), 2.60-2.44 (m, 4H), 2.28-2.11 (m, 3H), 2.06-1.80 (m, 2H). ppm. $^{13}$C NMR (125 MHz, CDCl$_3$, 23° C., δ): 211.0, 161.7 (d, J=244.4 Hz), 140.6 (d, J=3.1 Hz), 128.2 (d, J=7.8 Hz), 115.5 (d, J=21.1 Hz), 42.2, 41.5, 34.3 ppm. $^{19}$F NMR (470 MHz, CDCl$_3$, 23° C., δ): −116.5 ppm. 4-(2-fluorophenyl)cyclohexanone (3mb): $^1$H NMR (500 MHz, CDCl$_3$, 23° C., δ): 7.25-7.17 (m, 2H), 7.11 (td, J=7.5, 1.3 Hz, 1H), 7.08-7.02 (m, 1H), 3.37 (tt, J=12.2, 3.3 Hz, 1H), 2.60-2.44 (m, 4H), 2.28-2.11 (m, 2H), 2.06-1.80 (m, 2H) ppm. $^{13}$C NMR (125 MHz, CDCl$_3$, 23° C., δ): 211.0, 160.7 (d, J=245.2 Hz), 131.6 (d, J=14.5 Hz), 128.1 (d, J=8.5 Hz), 127.4 (d, J=4.8 Hz), 124.4 (d, J=3.5 Hz), 115.7 (d, J=22.7 Hz) 41.4, 35.8 (d, J=2.4 Hz) 32.7 ppm. $^{19}$F NMR (470 MHz, CDCl$_3$, 23° C., δ): −119.0 ppm.

Reactions without Catalyst

Under N$_2$ atmosphere, an oven-dried 4 mL vial was charged with Selectfluor (71 mg, 200 μmol, 2.0 equiv.) and 4-phenylcyclohexanone (17.4 mg, 100 μmol, 1.0 equiv.) in acetonitrile (1.0 mL, c=0.10 M). The resulting reaction mixture was stirred at 80° C. for 24 h. After cooling to room temperature, 1,4-bistrifluoromethylbenzene (3.6 mg, 2.6 μl, 17 μmol, 0.17 equiv.) was added to the reaction mixture, stirred and a sample (approx. 0.1 mL) was diluted with CD$_3$CN (0.5 mL) and the yield of the title products was determined by $^{19}$F NMR using 1,4-bis(trifluoromethyl)benzene as an internal standard to be <1%.

Example 15. (R)-4-(2-Fluorobenzyl)-3-propionyloxazolidin-2-one (3na) and (R)-4-(4-fluorobenzyl)-3-propionyloxazolidin-2-one (3nb)

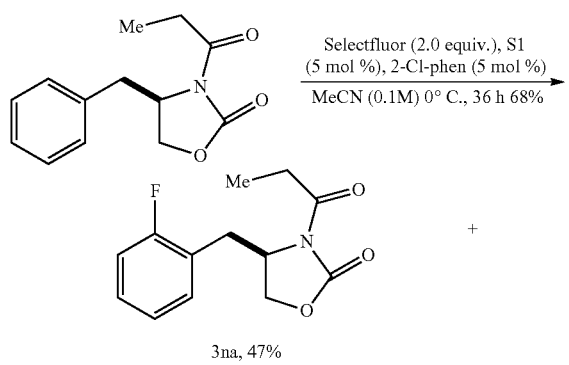

3na, 47%

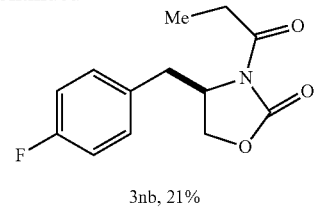

3nb, 21%

A mixture of palladium complex S1 (27.7 mg, 50.0 μmol, 5.00 mol %) and 2-chloro-phenanthroline (10.7 mg, 50.0 μmol, 5.00 mol %.) was dissolved in acetonitrile (5.0 mL). This mixture was added to a 20 mL vial containing a solution of Selectfluor (709 mg, 2.00 mmol, 2.00 equiv.) and (R)-4-benzyl-3-propionyloxazolidin-2-one (233 mg, 1.0 mmol, 1.0 equiv.) in acetonitrile (5.0 mL, final c=0.10 M). The reaction mixture was stirred for 36 hours at 0° C. and then transferred to a separatory funnel. Dichloromethane (50 mL) was added and the organic layer was washed with water (50 mL) with brine added (10 mL). The aqueous layer was extracted with dichloromethane (3×50 mL). The combined organic layers were dried over sodium sulfate, filtered, and concentrated in vacuo at 40° C. to afford a pale yellow solid. The residue was dissolved in dichloromethane (2 mL), loaded onto a short plug of silica (20 g) and eluted with ethyl acetate/dichloromethane 20:90 (v/v) and concentrated in vacuo to afford a colorless solid (225 mg) containing the title compounds (171 mg, 0.68 mmol, 68% yield, 3na:3nb (69:31)), (R)-4-benzyl-3-propionyloxazolidin-2-one and minor inseparable impurities. The yield and selectivity were determined by $^{19}$F using 1,4-bis(trifluoromethyl)benzene as an internal standard (standard: δ −63.4 ppm, 6 F; compared with product peaks at δ −116.8 and −118.8 ppm; first relaxation time of 10 s to ensure accurate integration). The yield and selectivity were determined by $^{19}$F using 1,4-bis(trifluoromethyl)benzene as an internal standard (standard: δ −63.4 ppm, 6 F; compared with product peaks at δ −115.1 and −117.1 ppm; first relaxation time of 10 s to ensure accurate integration). Purification by HPLC (MultoKrom Si, 3 μm, 20 mm×250 mm, isohexane:isopropanol 99:1, 20 mL/min, 8.3 MPa, 308 K, 220 nm UV) provided purified product isomers, yielding the title compound 3na (98% pure by HPLC, retention time 7.1 min.) and 3nb (99% pure by HPLC, retention time 8.8 min). $R_f$=0.35 (ethyl acetate/dichloromethane 10:90 (v/v)). HRMS-FIA(m/z) calculated for $C_{13}H_{14}FNO_3Na$ [M+Na]$^+$, 274.0850; found, 274.0849.

NMR Spectroscopy: (R)-4-(2-fluorobenzyl)-3-propionyloxazolidin-2-one (3na): $^1$H NMR (500 MHz, CDCl$_3$, 23° C., δ): 7.31-7.22 (m, 1H), 7.19 (td, J=7.5, 1.9 Hz, 1H), 7.11 (td, J=7.5, 1.2 Hz, 1H), 7.07 (ddd, J=9.7, 8.3, 1.1 Hz, 1H), 4.75 (tt, J=8.1, 3.1 Hz, 1H), 4.30-4.22 (m, 1H), 4.20 (dd, J=9.1, 2.7 Hz, 1H), 3.22 (dd, J=13.7, 3.5 Hz, 1H), 3.11-2.84 (m, 3H), 1.20 (t, J=7.2 Hz, 3H) ppm. $^{13}$C NMR (125 MHz, CDCl$_3$, 23° C., δ): 174.2, 161.5 (d, J=245.1 Hz), 153.6, 131.9 (d, J=4.7 Hz), 129.5 (d, J=8.3 Hz), 124.7 (d, J=3.5 Hz), 122.4 (d, J=16.0 Hz), 115.9 (d, J=22.2 Hz), 66.6 (d, J=2.5 Hz), 54.4, 31.4, 29.3, 8.4 ppm. $^{19}$F NMR (470 MHz, CDCl$_3$, 23° C., δ): −117.1 ppm. (R)-4-(4-fluorobenzyl)-3-propionyloxazolidin-2-one (3nb): $^1$H NMR (500 MHz, CDCl$_3$, 23° C., δ): 7.17 (dd, J=8.5, 5.4 Hz, 2H), 7.02 (t, J=8.6 Hz, 2H), 4.64 (ddt, J=9.3, 7.7, 3.0 Hz, 1H), 4.22 (ddd, J=8.8, 7.9, 0.7 Hz, 1H), 4.14 (dd, J=9.1, 2.7 Hz, 1H), 3.25 (dd, J=13.5, 3.3 Hz, 1H), 3.07-2.84 (m, 2H), 2.77 (dd, J=13.6, 9.4 Hz, 1H), 1.20 (td, J=7.3, 1.3 Hz, 3H) ppm. $^{13}$C NMR (125 MHz, CDCl$_3$, 23° C., δ): 174.2, 162.3 (d, J=246.2 Hz), 153.5, 131.1 (d, J=3.4 Hz), 131.0 (d, J=7.9 Hz), 116.0 (d, J=21.4 Hz), 66.3, 55.2 (d, J=1.5 Hz), 37.3, 29.3, 8.4 ppm. $^{19}$F NMR (470 MHz, CDCl$_3$, 23° C., δ): −115.1 ppm.

Reactions without Catalyst

Under N$_2$ atmosphere, an oven-dried 4 mL vial was charged with Selectfluor (71 mg, 200 μmol, 2.0 equiv.) and (R)-4-benzyl-3-propionyloxazolidin-2-one (23.3 mg, 100 μmol, 1.0 equiv.) in acetonitrile (1.0 mL, c=0.10 M). The resulting reaction mixture was stirred at 80° C. for 24 h. After cooling to room temperature, 1,4-bistrifluoromethyl-benzene (3.6 mg, 2.6 μl, 17 μmol, 0.17 equiv.) was added to the reaction mixture, stirred and a sample (approx. 0.1 mL) was diluted with CD$_3$CN (0.5 mL) and the yield of the title products was determined by $^{19}$F NMR using 1,4-bis(trifluoromethyl)benzene as an internal standard to be 17% (3na:3nb (65:35)).

Example 16. N-Acetyl-L-(2-fluoro)phenylalanine methyl ester (3oa) and N-Acetyl-L-(4-fluoro)phenylalanine methyl ester (3ob)

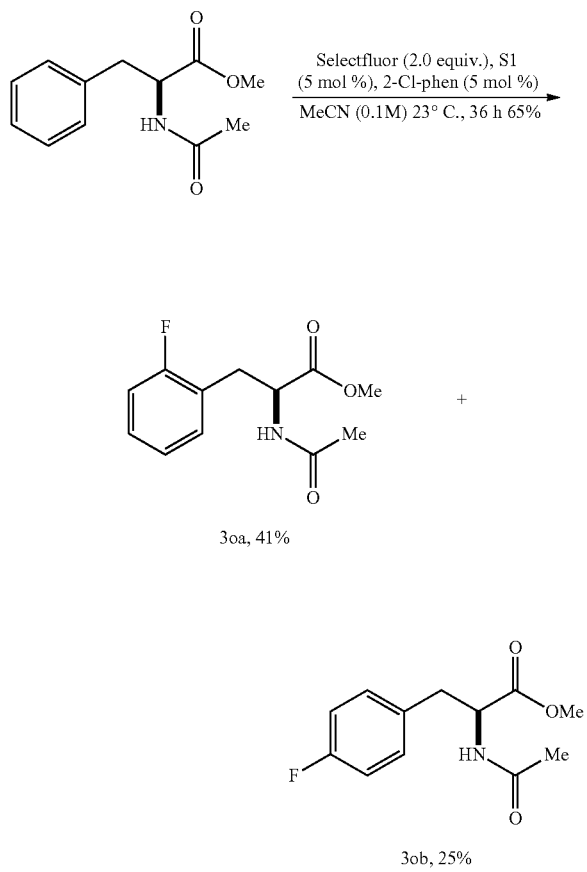

3oa, 41%

3ob, 25%

A mixture of palladium complex S1 (27.7 mg, 50.0 μmol, 5.00 mol %) and 2-chloro-phenanthroline (10.7 mg, 50.0 μmol, 5.00 mol %.) was dissolved in acetonitrile (8.0 mL). This mixture was added to a 20 mL vial containing a solution of Selectfluor (709 mg, 2.00 mmol, 2.00 equiv.) and N-Acetyl-L-phenylalanine methyl ester (221 mg, 1.00 mmol, 1.00 equiv.) in acetonitrile (2.0 mL, final c=0.10 M). The reaction mixture was stirred for 36 hours at 23° C. and then transferred to a separatory funnel. Chloroform (100 mL) was added and the organic layer was washed with saturated aqueous NaHCO$_3$ solution (1×50 mL). The aqueous layer was extracted with chloroform (4×100 mL). The combined organic layers were dried over sodium sulfate, filtered, and concentrated in vacuo at 40° C. to afford a pale yellow solid. The residue was dissolved in ethyl acetate (2 mL), loaded onto a short plug of silica (20 g) and eluted with ethyl acetate. A colorless solid (172 mg) containing the title compounds (158 mg, 0.659 mmol, 66% yield, 3oa:3ob (62:38)) and N-Acetyl-L-(4-fluoro)phenylalanine methyl ester was obtained. The yield and selectivity were determined by $^{19}$F using 1,4-bis(trifluoromethyl)benzene as an internal standard (standard: δ −63.4 ppm, 6 F; compared with product peaks at δ −116.0 and −118.1 ppm; first relaxation time of 10 s to ensure accurate integration). Purification by HPLC (YMC-Triart C18, 5 μm, 4.6 mm×150 mm, MeCN:H$_2$O 75:25, 20 mL/min, 9.2 MPa, 308 K, 210 nm UV) provided purified product isomers on a preparative scale, yielding the title compounds 3oa (56 mg, 0.234 mmol, 23%, >99% pure by HPLC, retention time 11.2 min.) and 3ob (35 mg, 0.146 mmol, 15%, >99% pure by HPLC, retention time 12.3 min.). The spectra matched the reported spectra for the title compounds. See Burk et al., *J. Am. Chem. Soc.*, 1993, 115, 10125-10138. R$_f$=0.80 (ethyl acetate).

NMR Spectroscopy: N-Acetyl-L-(2-fluoro)phenylalanine methyl ester (3fa): $^1$H NMR (500 MHz, CDCl$_3$, 23° C., δ) 7.25-7.20 (m, 1H), 7.12 (td, J=7.4, 1.9 Hz, 1H), 7.08 (td, J=7.4, 1.2 Hz, 1H), 7.03 (ddd, J=9.7, 8.2, 1.2 Hz, 1H), 5.96 (d, J=7.8 Hz, 2H), 4.87 (dt, J=7.9, 5.9 Hz, 1H), 3.74 (s, 3H), 3.18 (dddd, J=40.8, 13.8, 6.0, 1.2 Hz, 2H), 1.98 (s, 3H) ppm. $^{13}$C NMR (125 MHz, CDCl$_3$, 23° C., δ): 172.1, 169.8, 161.5 (d, J=245.0 Hz), 131.8 (d, J=4.3 Hz), 129.2 (d, J=8.0 Hz), 124.4 (d, J=3.5 Hz), 123.1 (d, J=16.0 Hz), 115.5 (d, J=22.2 Hz), 52.6, 52.6, 31.6, 23.5 ppm. $^{19}$F NMR (471 MHz, CDCl$_3$, 23° C., δ) −118.1 ppm. N-Acetyl-L-(4-fluoro)phenylalanine methyl ester (3fb): $^1$H NMR (500 MHz, CDCl$_3$, 23° C., δ) δ 7.05 (dd, J=8.6, 5.5 Hz, 2H), 6.98 (t, J=8.7 Hz, 2H), 5.91 (d, J=7.7 Hz, 1H), 4.86 (dt, J=7.7, 5.7 Hz, 1H), 3.73 (s, 3H), 3.22-3.01 (m, 2H), 1.99 (s, 3H) ppm. $^{13}$C NMR (125 MHz, CDCl$_3$, 23° C., δ):172.1, 169.7, 162.2 (d, J=245.6 Hz), 131.7 (d, J=3.1 Hz), 130.9 (d, J=8.0 Hz), 115.6 (d, J=21.3 Hz), 53.3, 52.6, 37.3, 23.3 ppm. $^{19}$F NMR (471 MHz, CDCl$_3$, 23° C., δ) −116.0 ppm. HRMS-FIA(m/z) calculated for C$_{12}$H$_{15}$FNO$_3$ [M+H]$^+$, 240.1036; found, 240.1059.

Reaction without Catalyst:

Under N$_2$ atmosphere, an oven-dried 4 mL vial was charged with Selectfluor (71 mg, 200 μmol, 2.0 equiv.), N-Acetyl-L-phenylalanine methyl ester (22.1 mg, 1.00 mmol, 1.00 equiv.) and acetonitrile (1.0 mL, c=0.10 M). The resulting reaction mixture was stirred at 80° C. for 24 h. After cooling to room temperature, 1,4-bistrifluoromethyl-benzene (3.6 mg, 2.6 μl, 17 μmol, 0.17 equiv.) was added to the reaction mixture, stirred and a sample (approx. 0.1 mL) was diluted with CD$_3$CN (0.5 mL) and the yield of the title products was determined by $^{19}$F NMR using 1,4-bis(trifluoromethyl)benzene as an internal standard to be 7% (6% 3oa, 1% 3ob).

Example 17. NMR Evaluation of Oxidation of Complex 1

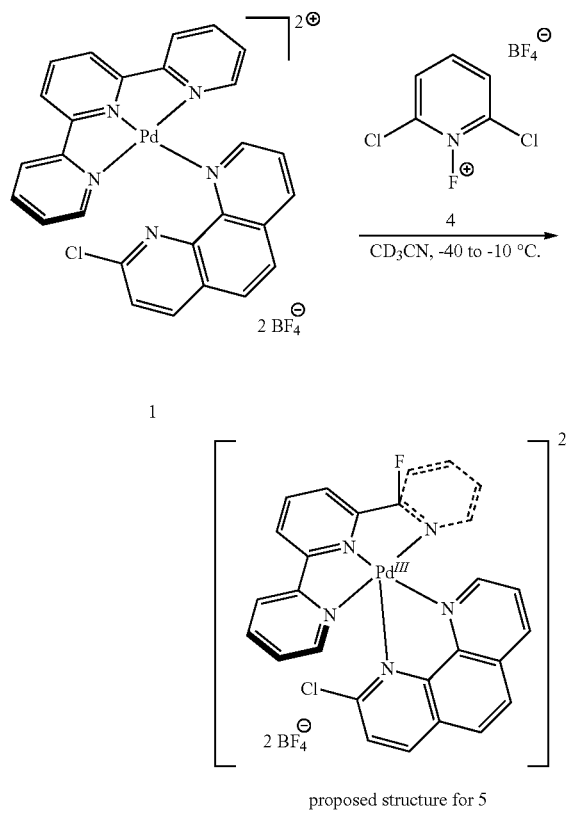

1 proposed structure for 5

To solution of catalyst 1 at −40° C., prepared from a mixture of palladium complex S1 (13.9 mg, 25 µmol, 1.0 equiv.) and 2-chloro-phenanthroline (5.4 mg, 25 µmol, 1.0 equiv.) in CD$_3$CN (2 mL), a solution of 2,6-dichloro-1-fluoropyridinium tetrafluoroborate (4) (6.4 mg, 25 µmol, 1.0 equiv. in 0.25 mL CD$_3$CN) at −40° C. was added in a 4 mL vial in the cold well of glovebox. The solution was stirred for 5 min and a dark purple color formed. The solution was carefully transferred to a cooled J-Young NMR tube then frozen at −60° C., sealed and removed from the glovebox. Vacuum was applied to the frozen solid and then the sample was transferred to the NMR instrument set to −40° C. After allowing 5 min in the NMR for the sample to thaw and the temperature to stabilize, the $^{19}$F NMR spectra were measured. After −40° C., the sample was warmed at 10° C. intervals up to −10° C., allowing the sample to equilibrate for 5 min before the $^{19}$F NMR were measured. The tetrafluoroborate was taken as an internal standard for $^{19}$F NMR (δ −150.1 ppm, 12 F) and used to determine oxidant consumption (δ 30.1 ppm, 1 F). The amount of oxidant remaining was determined to be: 68% at −40° C.; 63% at −30° C.; 48% at −20° C.; and 42% at −10° C. The region between δ −150 and −400 ppm contained no signals that could be attributed to formation of a Pd(IV)-F.

Example 18. Representative Procedure for Fluorination of Heteroaryl Substrates Under N$_2$ atmosphere, an oven-dried 4 mL vial was charged with the heteroaryl substrate (50 mmol, 1.0 equiv.), either Selectfluor (35.4 mg, 100 mmol, 2.00 equiv.) or NFBS (30.7 mg, 100 mmol, 2.00 equiv.) and acetonitrile (0.25 mL). In a separate 4 mL vial, a solution of the palladium catalyst 1 was prepared (5 mol % Pd(II) per 0.25 mL). The catalyst solution was then added to the reaction mixture (final c=0.1 M) and the resulting reaction mixture was stirred at 0, 25 or 50° C. for 8 to 36 h. After cooling to room temperature, 1,4-bis(trifluoromethyl)benzene (1.8 mg, 1.3 ml, 17 mmol, 0.17 equiv.) was added to the reaction mixture, stirred and a sample (approx. 0.1 mL) was diluted with CD$_3$CN (0.5 mL), and a yield was determined by $^{19}$F NMR using 1,4-bis(trifluoromethyl)benzene as an internal standard (standard: d −63.4 ppm, 6 F; compared with product peaks).

IV. Electron Paramagnetic Resonance (EPR) Spectroscopy (i) Synthesis of Complex 5

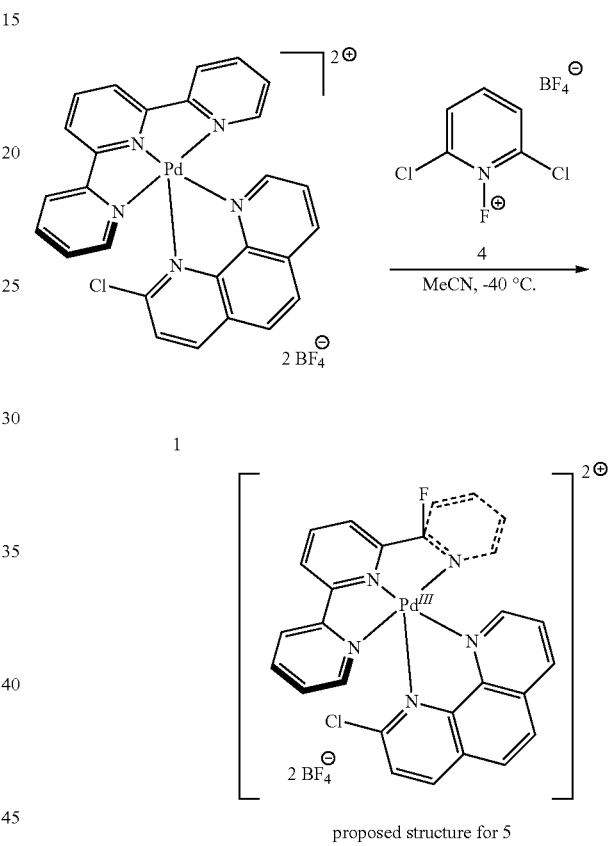

1 proposed structure for 5

To a solution of catalyst 1 at −40° C., prepared from a mixture of palladium complex S1 (13.9 mg, 25 µmol, 1.0 equiv.) and 2-chloro-phenanthroline (5.4 mg, 25 µmol, 1.0 equiv.) in MeCN (2 mL), a solution of 2,6-dichloro-1-fluoropyridinium tetrafluoroborate (4) (6.4 mg, 25 µmol, 1.0 equiv. in 0.25 mL MeCN) at −40° C. was added in a 4 mL vial in the cold well of glovebox. The resulting solution gradually (30 min) turned red-orange and then dark purple and was then quickly transferred into an EPR tube and frozen at 77K.

Figure 2:
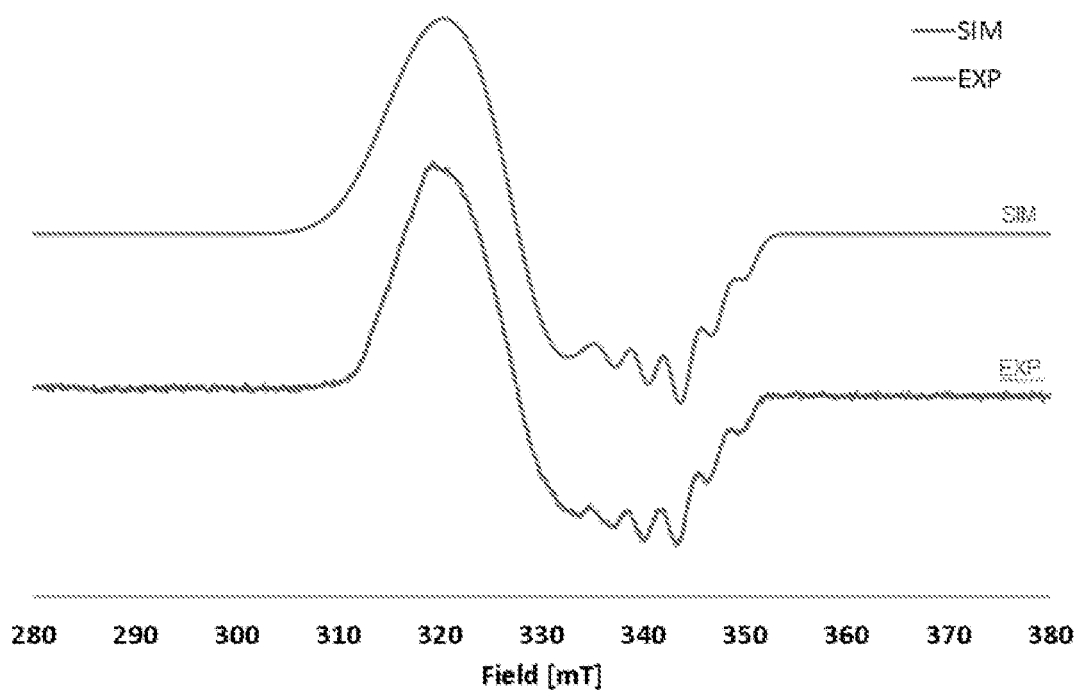
FIG. 2 shows the solid- and solution-state Electron Paramagnetic Resonance (EPR) spectra for Pd(III) complex 5 at 30K, with the experimental spectrum (red) and simulated spectrum (blue) of complex 5.

The solid- and solution-state EPR data for Pd(III) complex 5 display spectra (FIG. 2) at 30K. FIG. 2 depicts experimental (red) and simulated (blue) spectrum of complex 5. $g_1$=2.00799, $g_2$=2.10557, $g_3$=2.16726, and superhyperfine coupling (G) for two nitrogen atoms of terpy ligand $A_N$ (2N)=31.6546 G was observed for A (z,z). X-band EPR spectrum was collected at 30 K at microwave frequency=9.64756 GHz, microwave power=0.20 mW and a modulation amplitude of 7.46 G. Residual line widths of 66, 274, 320 MHz were used to simulate line broadening due to unresolved hyperfine couplings.

V. X-Ray Crystallographic Analysis (i) General Procedure for X-Ray Data Collection and Refinement A crystal was mounted on a nylon loop using Perfluoropolyether, and transferred to a Bruker AXS Enraf-Nonius KappaCCD diffractometer (MoKα radiation, λ=0.71073 Å) equipped with an Oxford Cryosystems nitrogen flow apparatus. The sample was held at 100(2) K during the experiment. The collection method involved 0.4° scans in ω at 30.9980 in 2θ. Data integration down to 0.69 Å resolution was carried out using EVALCCD 1.6 (Bruker diffractometer, 2008) with reflection spot size optimisation. Absorption corrections were made with the program SADABS (Bruker diffractometer, 2012). The structure was solved by the direct methods procedure and refined by least-squares methods against $F^2$ using SHELXS and SHELXL (Sheldrick, 2014). Non-hydrogen atoms were refined anisotropically, and hydrogen atoms were allowed to ride on the respective atoms. Special refinement details, if applicable, are given for each compound below. Crystal data, details of data collection and refinement, and selected geometric parameters are given in the tables below. Graphics were produced using the DIAMOND software program (© Crystal Impact GbR, 1997-2013)). Computer programs: APEX2 v2009.3.0 (Bruker-AXS, 2009), EVALCCD 1.6 (Bruker-AXS, 2008), SHELXS (Sheldrick, 2014), SHELXL (Sheldrick, 2014), Olex2 (Dolomanov et al., 2009).

(ii) [(terpy)Pd(2-Cl-phen)][BF$_4$]$_2$ (1). (CCDC <1465063>)

Figure 3:
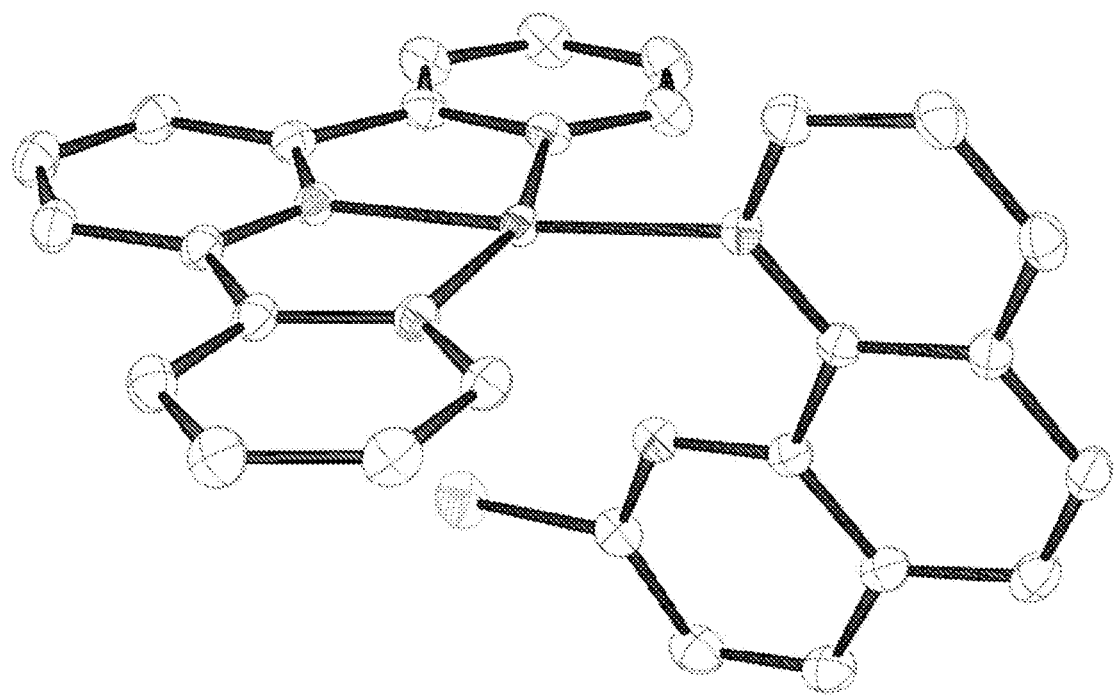
FIG. 3 shows the X-ray structure of compound 1. The X-ray structure of 1 is shown with 50% probability ellipsoids, and H-atoms, counteranions, and solvent molecules are omitted for clarity.

Compound 1 was crystallized from MeCN/Et$_2$O. The X-ray structure of compound 1 is shown in FIG. 3. Computer programs used to solve the X-ray structure include: DATCOL (Bruker AXS, 2006), REVALCCD V. 1.6, 2008, SHELXS (Sheldrick, 2013), SHELXL (Sheldrick, 2013), DIAMOND (Crystal Impact GbR, 1997-2013), Olex2 (Dolomanov et al., 2009). X-ray structure of 1 is shown with 50% probability ellipsoids; H-atoms, counteranions, and solvent molecules omitted for clarity. The axial N—Pd distance is 2.60 Å. The sum of the Pd and N van der Waals radii is 3.7 Å. See Bondi, A., *J. Phys. Chem.* 1964, 68, 441; Hu, S.-Z., Zhou, Z.-H., and Robertson, B. E. *Z. Kristallogr.* 2009, 224, 375.

The X-ray crystal structure of Pd (II) compound 1 shows a square planar geometry at Pd, with the apical phenanthroline nitrogen in close proximity to the palladium (2.6 Å of the apical Pd—N; the sum of Pd and N van der Waals radii is 3.7 Å) (FIG. 3).[14] The proximity of the apical nitrogen to the palladium suggests significant contribution to the HOMO from both atoms, which may increase the energy of the HOMO.

TABLE 1

X-ray crystal data of compound 1.

(9764sadabs)

| Crystal data | |
|---|---|
| Chemical formula | C$_{27}$H$_{18}$ClN$_5$Pd•2(BF$_4$)•C$_2$H$_3$N |
| M$_r$ | 768.99 |
| Crystal system, space group | MONOCLINIC, P2$_1$/c |
| Temperature (K) | 100 |
| a, b, c (Å) | 8.070 (1), 41.823 (5), 9.1701 (6) |
| β (°) | 104.662 (7) |
| V (Å$^3$) | 2994.3 (5) |
| Z | 4 |

TABLE 1-continued

X-ray crystal data of compound 1.

(9764sadabs)

| | |
|---|---|
| Radiation type | Mo Kα |
| μ (mm$^{-1}$) | 0.79 |
| Crystal size (mm) | 0.15 × 0.10 × 0.06 |
| Data collection | |
| Diffractometer | Bruker AXS Enraf-Nonius KappaCCD |
| Absorption correction | Gaussian SADABS (Bruker AXS, 2012) |
| T$_{min}$, T$_{max}$ | 0.891, 0.955 |
| No. of measured, independent and observed [I > 2σ (I)] reflections | 49913, 9465, 8874 |
| R$_{int}$ | 0.023 |
| (sin θ/λ)$_{max}$ (Å$^{-1}$) | 0.725 |
| Refinement | |
| R[F$^2$ > 2σ(F$^2$)], wR(F$^2$), S | 0.025, 0.060, 1.11 |
| No. of reflections | 9465 |
| No. of parameters | 425 |
| H-atom treatment | H-atom parameters constrained |
| Δρ$_{max}$, Δρ$_{min}$ (e Å$^{-3}$) | 0.50, −0.89 |

VI. Density Functional Theory Experiments (i) Methods for DFT Calculations

Density Functional Theory (DFT) calculations were performed at the Max-Planck-Institut für Kohlenforschung Computer Cluster using the Gaussian09 program package. Structural optimizations and frequency calculations, used to confirm if the structure is a minimum and then to obtain thermal corrections to the Gibbs Free Energy, were performed with B3LYP or ωB97X-D along with the 6−31+G(d) basis set on all atoms except Pd and the effective core potential (ECP) LanL2DZ on Pd, using the atomic coordinates of molecular structures created in GaussView 5.0.8 and using the atomic coordinates of the crystal structure as starting points for Pd(II)(terpy)(2-Cl-phen) (1 without counterions). Single point energy calculations were performed with M06L or M11L functional and 6−311++G(d,p) basis set on all atoms except Pd and the Stuttgart-Dresden (SDD) quasirelativistic pseudopotential (MWB28) with basis set (Pd: (8s7p6d)/[6s5p3d]), with basis set Pd (SDD), extended by polarization function (Pd: f, f-orbital coefficient: 1.472) on Pd. Solvent effects of acetonitrile were taken into account for the single point calculations using the conductor-like polarized continuum solvation model (CPCM). Frequency calculations were performed to confirm whether the structure is a minimum. Images were generated using GaussView 5.0.8.

FIGS. 4A-5B depict the DFT energy profiles.

(ii) Visualization of LUMO, HOMO, and SOMO

Shown in FIG. 6A is a visualization of LUMO of F-TEDA (left) and NFSI (right) with isovalue 0.05, for compound 1. Shown in FIG. 6B is a visualization of HOMO of 2-Cl-phen-Pd-terpy complex with isovalue 0.05. Shown in FIG. 6C is a visualization of SOMO of Pd(III)-F complex 5 with isovalue 0.05 and 0.02.

(iii) The Optimized Structure of Compound 1 with M06L/B3LYP and Cartesian Coordinates (Å)

Figure 7A:
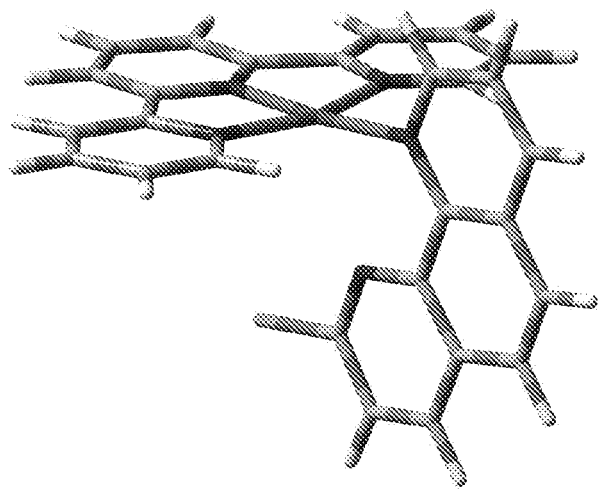
FIG. 7A shows an optimized structure of compound 1 with M06L/B3LYP.

The optimized structure of 1 with M06/BS I and Cartesian coordinates (Å) are shown in FIG. 7A and Table 2. The corrections, and sum of energies are shown in Table 3. The structure was optimized using B3LYP/6-31+G(d) with LANL2DZ (for Pd).

TABLE 2

The Cartesian coordinates (Å) of an optimized structure of compound 1.

| Atom | X | Y | Z |
|---|---|---|---|
| Pd | −0.43700600 | −0.00082700 | −0.69650100 |
| Cl | −0.62112200 | 0.00396300 | 3.35758700 |
| N | −0.80264800 | 2.05776200 | −0.66646300 |
| N | −2.35851000 | 0.00051700 | −0.23140400 |
| N | 1.55888200 | −0.00230300 | −1.38057700 |
| N | −0.80423500 | −2.05900500 | −0.66329700 |
| C | −0.28425100 | 4.39496500 | −0.81885800 |
| H | 0.44886600 | 5.16470400 | −1.02462600 |
| C | −4.33270100 | 1.21852600 | 0.27338600 |
| H | −4.86020100 | 2.15397000 | 0.40508100 |
| C | −2.51072900 | 3.69106000 | −0.20759600 |
| H | −3.52925700 | 3.92970200 | 0.07095300 |
| C | −1.59563100 | 4.71934400 | −0.46306000 |
| H | −1.90568000 | 5.75458900 | −0.38455000 |
| C | −2.10212500 | 2.36051400 | −0.31386500 |
| N | 1.23091100 | 0.00098700 | 1.41552200 |
| C | 2.65552300 | −0.00154300 | −0.54342000 |
| C | −1.59973400 | −4.71950400 | −0.45606700 |
| H | −1.91074400 | −5.75435600 | −0.37626300 |
| C | −2.10397200 | −2.35997300 | −0.31034700 |
| C | 2.14429100 | 0.00366600 | 3.64700500 |
| H | 1.95060800 | 0.00511200 | 4.71114200 |
| C | −5.00356900 | 0.00198500 | 0.44883700 |
| H | −6.05297000 | 0.00253300 | 0.71839300 |
| C | 3.64217100 | 0.00121100 | 1.72961500 |
| C | −2.97830200 | −1.19798300 | −0.07382500 |
| C | 3.97557000 | −0.00217500 | −1.08891400 |
| C | 3.42940500 | 0.00291200 | 3.13487000 |
| H | 4.28269700 | 0.00372000 | 3.80431800 |
| C | −2.97740400 | 1.19959900 | −0.07554500 |
| C | −4.33359200 | −1.21535700 | 0.27507600 |
| H | −4.86196600 | −2.15012200 | 0.40802100 |
| C | 2.49301700 | 0.00013200 | 0.89060700 |
| C | 4.12467200 | −0.00362700 | −2.49727900 |
| H | 5.12091900 | −0.00414900 | −2.92626500 |
| C | −2.51388400 | −3.69001800 | −0.20218800 |
| H | −3.53266400 | −3.92723000 | 0.07663300 |
| C | 0.07760400 | −3.05149100 | −0.90458400 |
| H | 1.08108800 | −2.75391600 | −1.17402400 |
| C | 1.73232900 | −0.00356000 | −2.71947800 |
| H | 0.83587100 | −0.00413300 | −3.32629400 |
| C | 5.11168600 | −0.00133900 | −0.20983000 |
| H | 6.10265000 | −0.00214200 | −0.64990200 |
| C | 1.08100600 | 0.00255400 | 2.72127100 |
| C | 4.95327500 | 0.00027900 | 1.14709400 |
| H | 5.81673000 | 0.00114900 | 1.80316000 |
| C | −0.28796600 | −4.39686700 | −0.81211300 |
| H | 0.44445500 | −5.16763900 | −1.01651200 |
| C | 3.00435700 | −0.00434400 | −3.31234500 |
| H | 3.09028300 | −0.00550700 | −4.39162000 |
| C | 0.08004400 | 3.04908800 | −0.90937300 |
| H | 1.08329700 | 2.75032200 | −1.17848400 |

(iv) The Optimized Structure of Compound 1 with M11L/ωB97X-D and Cartesian Coordinates (Å)

Figure 7B:
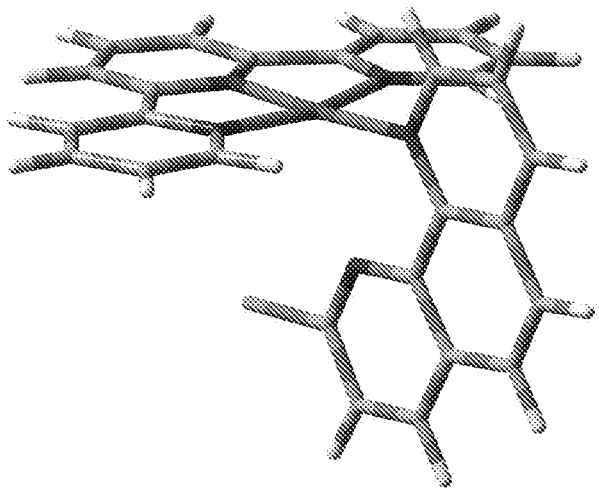
FIG. 7B shows an optimized structure of compound 1 with M11L/ωB97X-D.

The optimized structure of 1 with M11L/ωB97X-D and Cartesian coordinates (Å) are shown in FIG. 7B and Table 4. The corrections, and sum of energies are shown in Table 5. The structure was optimized using ωB97X-D/6-31+G(d) with LANL2DZ (for Pd).

TABLE 4

The Cartesian coordinates (Å) of an optimized structure of compound 1.

| Atom | X | Y | Z |
|---|---|---|---|
| Pd | −0.40028300 | −0.00000700 | −0.75245200 |
| Cl | −0.88621200 | 0.00025800 | 3.15269000 |
| N | −0.74536900 | 2.03998800 | −0.70422400 |
| N | −2.31124800 | −0.00038600 | −0.30176500 |
| N | 1.60567700 | 0.00026600 | −1.35821100 |
| N | −0.74450300 | −2.04013100 | −0.70400200 |
| C | −0.19003400 | 4.35976400 | −0.80580500 |
| H | 0.55507000 | 5.12260500 | −0.98727200 |
| C | −4.26537100 | 1.21402900 | 0.23468400 |
| H | −4.79013900 | 2.14833200 | 0.38018000 |
| C | −2.42840900 | 3.67807300 | −0.23175500 |
| H | −3.44547600 | 3.92670700 | 0.04112300 |
| C | −1.49673500 | 4.69441500 | −0.45953900 |
| H | −1.79177500 | 5.73182100 | −0.36443900 |
| C | −2.03485100 | 2.35164000 | −0.35777600 |
| N | 1.09836500 | 0.00030500 | 1.38695500 |
| C | 2.64552500 | 0.00031000 | −0.46200100 |
| C | −1.49475200 | −4.69485200 | −0.45907800 |
| H | −1.78935700 | −5.73237200 | −0.36388200 |
| C | −2.03387200 | −2.35229700 | −0.35755600 |
| C | 1.83936700 | 0.00058600 | 3.66862700 |
| H | 1.57086800 | 0.00068800 | 4.71587100 |
| C | −4.93106500 | −0.00090200 | 0.41489600 |
| H | −5.97608900 | −0.00109700 | 0.69817200 |
| C | 3.46693700 | 0.00052500 | 1.86788100 |
| C | −2.92085400 | −1.19323200 | −0.13108800 |
| C | 3.98678200 | 0.00028300 | −0.91532800 |
| C | 3.15448500 | 0.00063700 | 3.25154600 |
| H | 3.95605500 | 0.00075500 | 3.98117000 |
| C | −2.92135000 | 1.19223100 | −0.13117000 |
| C | −4.26488200 | −1.21556400 | 0.23475000 |
| H | −4.78925800 | −2.15008300 | 0.38027100 |
| C | 2.38826800 | 0.00039400 | 0.95799500 |
| C | 4.22430400 | 0.00013600 | −2.30858300 |
| H | 5.24439800 | 0.00006900 | −2.67600100 |
| C | −2.42686500 | −3.67888000 | −0.23140900 |

TABLE 3

| | |
|---|---|
| Zero-point correction = | 0.399440 (Hartree/Particle) |
| Thermal correction to Energy = | 0.425043 |
| Thermal correction to Enthalpy = | 0.425987 |
| Thermal correction to Gibbs Free Energy = | 0.342251 |
| Sum of electronic and zero-point Energies = | −1899.290678 |
| Sum of electronic and thermal Energies = | −1899.265075 |
| Sum of electronic and thermal Enthalpies = | −1899.264131 |
| Sum of electronic and thermal Free Energies = | −1899.347867 |
| CPCM (MeCN) M06L/6-311 + + G(d, p) with SDD + f (for Pd) E = | −1901.616198 |

TABLE 4-continued

The Cartesian coordinates (Å) of an optimized structure of compound 1.

| Atom | X | Y | Z |
|---|---|---|---|
| H | −3.44382800 | −3.92792700 | 0.04148200 |
| C | 0.15518800 | −3.01449500 | −0.91861000 |
| H | 1.15574500 | −2.70089800 | −1.18143900 |
| C | 1.85644900 | 0.00018300 | −2.67713300 |
| H | 0.99866200 | 0.00021300 | −3.33722500 |
| C | 5.06313400 | 0.00040400 | 0.03845200 |
| H | 6.08051200 | 0.00039500 | −0.33521700 |
| C | 0.84801100 | 0.00039400 | 2.67145600 |
| C | 4.81585300 | 0.00053400 | 1.37515700 |
| H | 5.63217800 | 0.00063200 | 2.08803400 |
| C | −0.18819100 | −4.35968400 | −0.80535100 |
| H | 0.55724100 | −5.12222800 | −0.98672600 |
| C | 3.15995700 | 0.00008600 | −3.18880000 |
| H | 3.31314300 | −0.00003700 | −4.25966700 |
| C | 0.15391300 | 3.01471500 | −0.91894100 |
| H | 1.15459200 | 2.70149900 | −1.18175700 |

TABLE 5

| | |
|---|---|
| Zero-point correction = | 0.405285 (Hartree/Particle) |
| Thermal correction to Energy = | 0.430491 |
| Thermal correction to Enthalpy = | 0.431435 |
| Thermal correction to Gibbs Free Energy = | 0.347953 |
| Sum of electronic and zero-point Energies = | −1898.826135 |
| Sum of electronic and thermal Energies = | −1898.800930 |
| Sum of electronic and thermal Enthalpies = | −1898.799986 |
| Sum of electronic and thermal Free Energies = | −1898.883467 |
| CPCM (MeCN) M11L/6-311 + + G(d, p) with SDD + f (for Pd) E = | −1901.596284 |

(v) The Optimized Structure of Complex 5 with M06L/B3LYP and Cartesian Coordinates (Å)

Figure 8A:
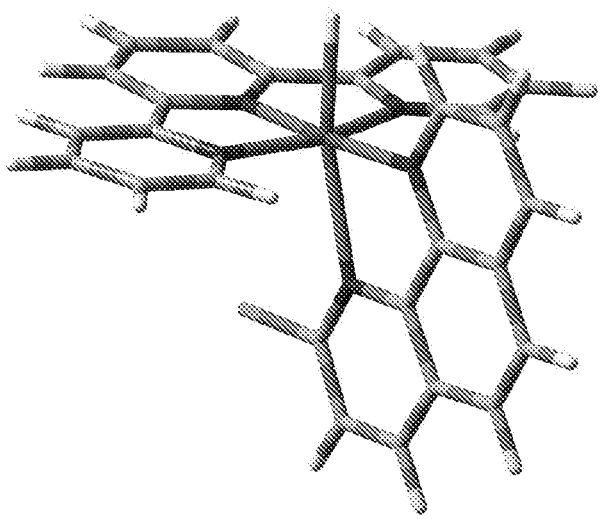
FIG. 8A shows an optimized structure of complex 5 with M06L/B3LYP.

The optimized structure of 5 with M06L/B3LYP and Cartesian coordinates (Å) are shown in FIG. 8A and Table 6. The corrections, and sum of energies are shown in Table 7. The structure was optimized using B3LYP/6-31+G(d) with LANL2DZ (for Pd).

TABLE 6

The Cartesian coordinates (Å) of an optimized structure of complex 5.

| Atom | X | Y | Z |
|---|---|---|---|
| Pd | 0.32263300 | −0.00024000 | −0.62389800 |
| Cl | 0.88825100 | 0.00183100 | 3.21056700 |
| N | 0.67957100 | −2.08074900 | −0.51949400 |
| N | 2.22876900 | −0.00026000 | −0.07916000 |
| N | −1.63422300 | −0.00048300 | −1.31713700 |
| N | 0.68009100 | 2.08016500 | −0.52106000 |
| C | 0.19279200 | −4.41341200 | −0.74552000 |
| H | −0.53050800 | −5.18775800 | −0.96795900 |
| C | 4.22075400 | −1.21648300 | 0.33472200 |
| H | 4.75479100 | −2.15177000 | 0.43659600 |
| C | 2.41932000 | −3.69386500 | −0.14730800 |
| H | 3.44724800 | −3.92611800 | 0.10005100 |
| C | 1.51475800 | −4.72698400 | −0.42053200 |
| H | 1.84259300 | −5.75905800 | −0.38319600 |
| C | 1.98845100 | −2.36697300 | −0.20435500 |
| N | −1.10101100 | 0.00081200 | 1.40438400 |
| C | −2.67865400 | −0.00010700 | −0.42358000 |
| C | 1.51568100 | 4.72632100 | −0.42392900 |
| H | 1.84367800 | 5.75837000 | −0.38731100 |
| C | 1.98899700 | 2.36639500 | −0.20606500 |
| C | −1.84199100 | 0.00222500 | 3.69804300 |
| H | −1.56537700 | 0.00284500 | 4.74376500 |
| C | 4.89617800 | −0.00037200 | 0.48940000 |
| H | 5.95489600 | −0.00041700 | 0.71976100 |
| C | −3.48840700 | 0.00119400 | 1.90819800 |
| C | 2.85411300 | 1.19895100 | 0.03346900 |
| C | −4.02265900 | −0.00042100 | −0.88777200 |
| C | −3.16499000 | 0.00201500 | 3.29177200 |
| H | −3.96017700 | 0.00246000 | 4.02926300 |
| C | 2.85381300 | −1.19953200 | 0.03434400 |
| C | 4.22105200 | 1.21579700 | 0.33381600 |
| H | 4.75531400 | 2.15103400 | 0.43497300 |
| C | −2.40876800 | 0.00065400 | 0.98569200 |
| C | −4.23962600 | −0.00117800 | −2.29055900 |
| H | −5.25539100 | −0.00145300 | −2.67137900 |
| C | 2.42007300 | 3.69325800 | −0.14992700 |

TABLE 6-continued

The Cartesian coordinates (Å) of an optimized structure of complex 5.

| Atom | X | Y | Z |
|---|---|---|---|
| H | 3.44802500 | 3.92552100 | 0.09731500 |
| C | −0.19250900 | 3.07016000 | −0.78915200 |
| H | −1.20187800 | 2.77702700 | −1.04155100 |
| C | −1.85128500 | −0.00118600 | −2.64536700 |
| H | −0.95503000 | −0.00147800 | −3.25869500 |
| C | −5.09326700 | 0.00009100 | 0.07083100 |
| H | −6.11420000 | −0.00015200 | −0.29440200 |
| C | −0.84638100 | 0.00158300 | 2.70016000 |
| C | −4.83706200 | 0.00089400 | 1.41504100 |
| H | −5.65246400 | 0.00130300 | 2.12977500 |
| C | 0.19368000 | 4.41273300 | −0.74877000 |
| H | −0.52947700 | 5.18704100 | −0.97180200 |
| C | −3.16075000 | −0.00155300 | −3.16149400 |
| H | −3.30436600 | −0.00210400 | −4.23463400 |
| F | 0.97225800 | −0.00116300 | −2.63114100 |
| C | −0.19318300 | −3.07080300 | −0.78683200 |
| H | −1.20253000 | −2.77771200 | −1.03937400 |

TABLE 7

| | |
|---|---|
| Zero-point correction = | 0.401756 (Hartree/Particle) |
| Thermal correction to Energy = | 0.428689 |
| Thermal correction to Enthalpy = | 0.429634 |
| Thermal correction to Gibbs Free Energy = | 0.343490 |
| Sum of electronic and zero-point Energies = | −1999.067450 |
| Sum of electronic and thermal Energies = | −1999.040516 |
| Sum of electronic and theimal Enthalpies = | −1999.039572 |
| Sum of electronic and theimal Free Energies = | −1999.125716 |
| CPCM (MeCN) M06L/6-311 + + G(d, p) with SDD + f (for Pd) E = | −2001.443197 |

(vi) The Optimized Structure of Complex 5 with M11L/ωB97X-D and Cartesian Coordinates (Å)

Figure 8B:
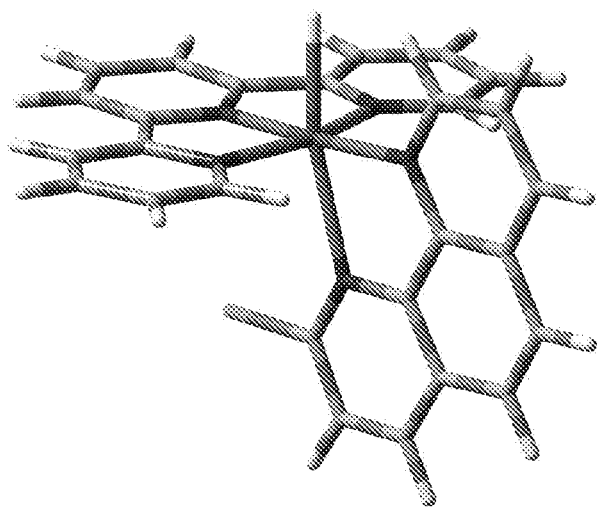
FIG. 8B shows an optimized structure of complex 5 with M11L/ωB97X-D.

The optimized structure of 5 with M11L/ωB97X-D and Cartesian coordinates (Å) are shown in FIG. 8B and Table 8. The corrections, and sum of energies are shown in Table 9. The structure was optimized using ωB97X-D/6–31+G(d) with LANL2DZ (for Pd).

TABLE 8

The Cartesian coordinates (Å) of an optimized structure of complex 5.

| Atom | X | Y | Z |
|---|---|---|---|
| Pd | 0.30591200 | −0.00002700 | −0.65222400 |
| Cl | 1.05332300 | 0.00007100 | 3.06956700 |
| N | 0.63810500 | −2.05371100 | −0.54191300 |
| N | 2.19946300 | 0.00000000 | −0.12970900 |
| N | −1.64778200 | −0.00008900 | −1.29463800 |
| N | 0.63814000 | 2.05368500 | −0.54204300 |
| C | 0.10616000 | −4.36824100 | −0.72829300 |
| H | −0.63149300 | −5.13280400 | −0.93130900 |
| C | 4.17439200 | −1.21437300 | 0.30224100 |
| H | 4.70691700 | −2.14893000 | 0.41262400 |
| C | 2.34723800 | −3.68142900 | −0.16468500 |
| H | 3.37295300 | −3.92872700 | 0.07452800 |
| C | 1.42220200 | −4.69883800 | −0.41463900 |
| H | 1.73136600 | −5.73536200 | −0.36647400 |
| C | 1.93654100 | −2.35616100 | −0.23482300 |
| N | −1.00769400 | 0.00003700 | 1.38248100 |
| C | −2.65557700 | 0.00000100 | −0.36922700 |

TABLE 8-continued

The Cartesian coordinates (Å) of an optimized structure of complex 5.

| Atom | X | Y | Z |
|---|---|---|---|
| C | 1.42225500 | 4.69881100 | −0.41501900 |
| H | 1.73141900 | 5.73534000 | −0.36696700 |
| C | 1.93655600 | 2.35615300 | −0.23489700 |
| C | −1.63756100 | 0.00020000 | 3.69757500 |
| H | −1.31454800 | 0.00027900 | 4.72935200 |
| C | 4.84599400 | −0.00000700 | 0.45983000 |
| H | 5.90237900 | −0.00000400 | 0.69727000 |
| C | −3.35737000 | 0.00019200 | 1.98811300 |
| C | 2.81651700 | 1.19347900 | −0.00680600 |
| C | −4.00559300 | −0.00002200 | −0.77478400 |
| C | −2.97354300 | 0.00025900 | 3.35316500 |
| H | −3.73401800 | 0.00036800 | 4.12538700 |
| C | 2.81652000 | −1.19348400 | −0.00683100 |
| C | 4.17438200 | 1.21436600 | 0.30229500 |
| H | 4.70689800 | 2.14891800 | 0.41275400 |
| C | −2.32703300 | 0.00007500 | 1.02755600 |
| C | −4.27575000 | −0.00021900 | −2.16578800 |
| H | −5.30437800 | −0.00026000 | −2.50878900 |
| C | 2.34726300 | 3.68142600 | −0.16487100 |
| H | 3.37296500 | 3.92872300 | 0.07440400 |
| C | −0.25488000 | 3.02401800 | −0.78566600 |
| H | −1.26015000 | 2.71168500 | −1.03146700 |
| C | −1.90919700 | −0.00024100 | −2.60751700 |
| H | −1.03498400 | −0.00019800 | −3.25204000 |
| C | −5.03716200 | 0.00011600 | 0.22701900 |
| H | −6.07161900 | 0.00013200 | −0.09604200 |
| C | −0.69025600 | 0.00005900 | 2.65871400 |
| C | −4.72688800 | 0.00023000 | 1.55287000 |
| H | −5.51034800 | 0.00035200 | 2.30145100 |
| C | 0.10623700 | 4.36819300 | −0.72876200 |
| H | −0.63137100 | 5.13275000 | −0.93195900 |
| C | −3.23391600 | −0.00033500 | −3.07362100 |
| H | −3.41772100 | −0.00052400 | −4.13960000 |
| F | 0.91670700 | −0.00002900 | −2.65760800 |
| C | −0.25494200 | −3.02407400 | −0.78534000 |
| H | −1.26023600 | −2.71177600 | −1.03108200 |

TABLE 9

| | |
|---|---|
| Zero-point correction = | 0.407683 (Hartree/Particle) |
| Thermal correction to Energy = | 0.434154 |
| Thermal correction to Enthalpy = | 0.435098 |
| Thermal correction to Gibbs Free Energy = | 0.349812 |
| Sum of electronic and zero-point Energies = | −1998.574792 |
| Sum of electronic and thermal Energies = | −1998.548321 |
| Sum of electronic and thermal Enthalpies = | −1998.547377 |
| Sum of electronic and thermal Free Energies = | −1998.632662 |
| CPCM (MeCN) M11L/6-311 + + G(d, p) with SDD + f (for Pd) E = | −2001.390395 |

(vii) The Optimized Structure of Complex 5 with M06L/B3L YP and Cartesian Coordinates (Å)

Figure 9A:
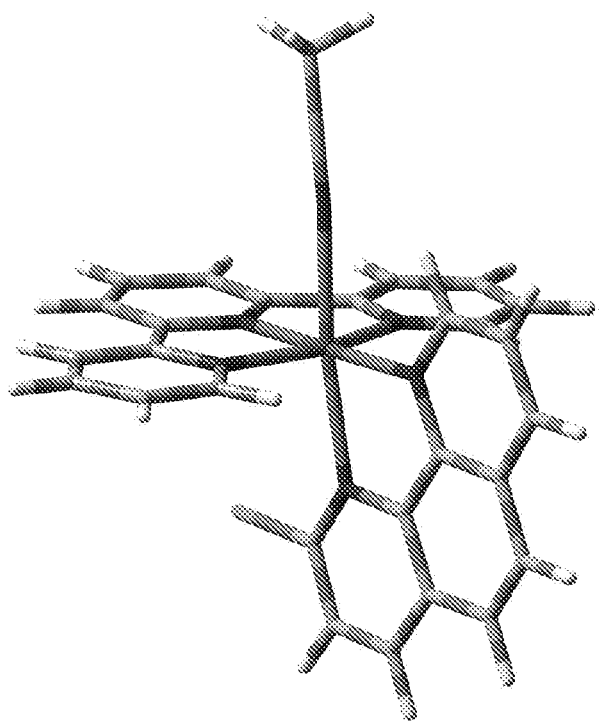
FIG. 9A shows an optimized structure of complex 5 with M06L/B3LYP.

The optimized structure of 5 with M06L/B3LYP and Cartesian coordinates (Å) are shown in FIG. 9A and Table 10. The corrections, and sum of energies are shown in Table 12. The structure was optimized using B3LYP/6-31+G(d) with LANL2DZ (for Pd).

TABLE 10

The Cartesian coordinates (Å) of an optimized structure of complex 5.

| Atom | X | Y | Z |
|---|---|---|---|
| Pd | 0.24938500 | 0.00039800 | 0.44724500 |
| Cl | 0.54474800 | -0.00326000 | -3.34093500 |
| N | 0.58046600 | 2.07526500 | 0.27354300 |
| N | 2.03748500 | -0.00014900 | -0.43961100 |
| N | -1.61769800 | 0.00110000 | 1.40256600 |
| N | 0.58093000 | -2.07468200 | 0.27710900 |
| C | 0.09439000 | 4.40984000 | 0.49917200 |
| H | -0.58885800 | 5.18250500 | 0.82966500 |
| C | 3.87623900 | 1.21801600 | -1.30388800 |
| H | 4.37095300 | 2.15194300 | -1.53729100 |
| C | 2.17085200 | 3.69678200 | -0.51196800 |
| H | 3.11850000 | 3.93550800 | -0.97852400 |
| C | 1.31574500 | 4.72871900 | -0.10072000 |

TABLE 10-continued

The Cartesian coordinates (Å) of an optimized structure of complex 5.

| Atom | X | Y | Z |
|---|---|---|---|
| H | -1.17947800 | -2.77071200 | 1.13572100 |
| C | -1.75288800 | 0.00228100 | 2.74310000 |
| H | -0.84307600 | 0.00275200 | 3.32643400 |
| C | -5.17694200 | 0.00011400 | 0.27115900 |
| H | -6.16965000 | 0.00052800 | 0.70711900 |
| C | -1.11970400 | -0.00267800 | -2.66741700 |
| C | -5.01469800 | -0.00118600 | -1.08767900 |
| H | -5.87739900 | -0.00183600 | -1.74452500 |
| C | 0.09535500 | -4.40897600 | 0.50667100 |
| H | -0.58774600 | -5.18123200 | 0.83842000 |
| C | -3.01932500 | 0.00286700 | 3.35353100 |
| H | -3.08647100 | 0.00381100 | 4.43440300 |
| C | -0.24581600 | 3.06467400 | 0.67217100 |
| H | -1.18001400 | 2.77236800 | 1.13113800 |
| N | 1.49420400 | 0.00227900 | 2.54129400 |
| C | 2.19577000 | 0.00310700 | 3.47776900 |
| C | 3.05631700 | 0.00412100 | 4.65154600 |
| H | 2.86955900 | 0.89287300 | 5.26424700 |
| H | 2.87068500 | -0.88438300 | 5.26495200 |
| H | 4.11113500 | 0.00466500 | 4.35631100 |

TABLE 11

| | |
|---|---|
| Zero-point correction = | 0.446791 (Hartree/Particle) |
| Thermal correction to Energy = | 0.477353 |
| Thermal correction to Enthalpy = | 0.478298 |
| Thermal correction to Gibbs Free Energy = | 0.383001 |
| Sum of electronic and zero-point Energies = | -2031.527339 |
| Sum of electronic and thermal Energies = | -2031.496777 |
| Sum of electronic and thermal Enthalpies = | -2031.495833 |
| Sum of electronic and thermal Free Energies = | -2031.591129 |
| CPCM (MeCN) M06L/6-311 + + G(d, p) with SDD + f (for Pd) E = | -2034.181162 |

TABLE 10-continued

The Cartesian coordinates (Å) of an optimized structure of complex 5.

| Atom | X | Y | Z |
|---|---|---|---|
| H | 1.60317600 | 5.76326400 | -0.24885500 |
| C | 1.79449800 | 2.36640900 | -0.31915900 |
| N | -1.28348600 | -0.00138100 | -1.34742700 |
| C | -2.73035400 | 0.00039200 | 0.59023600 |
| C | 1.31683400 | -4.72859800 | -0.09257100 |
| H | 1.60451300 | -5.76332900 | -0.23891500 |
| C | 1.79506800 | -2.36655800 | -0.31502300 |
| C | -2.19554000 | -0.00360500 | -3.57776300 |
| H | -1.99715800 | -0.00466300 | -4.64161600 |
| C | 4.50118400 | -0.00087100 | -1.60039000 |
| H | 5.48036100 | -0.00116100 | -2.06539600 |
| C | -3.70385800 | -0.00175300 | -1.67382900 |
| C | 2.61050800 | -1.20366900 | -0.70390700 |
| C | -4.04024600 | 0.00092500 | 1.14880600 |
| C | -3.48489100 | -0.00312200 | -3.07705200 |
| H | -4.33140200 | -0.00381300 | -3.75529200 |
| C | 2.61019800 | 1.20303700 | -0.70606300 |
| C | 3.87656300 | -1.21938800 | -1.30167900 |
| H | 4.37154000 | -2.15360100 | -1.53337600 |
| C | -2.56103400 | -0.00092100 | -0.82925400 |
| C | -4.15911400 | 0.00221200 | 2.56252200 |
| H | -5.14446400 | 0.00265500 | 3.01636900 |
| C | 2.17174000 | -3.69717400 | -0.50551700 |
| H | 3.11947200 | -3.93648900 | -0.97159900 |
| C | -0.24516900 | -3.06359400 | 0.67734700 |

(viii) The Optimized Structure of Selectfluor (F-TEDA) with M06L/B3L YP and Cartesian Coordinates (Å)

Figure 9B:
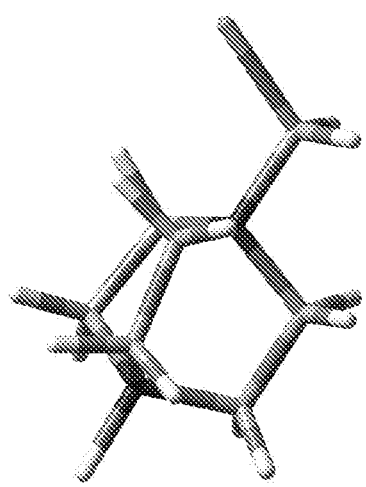
FIG. 9B shows an optimized structure of Selectfluor (F-TEDA-BF$_4$) with M06L/B3LYP.

The optimized structure of Selectfluor (F-TEDA) with M06L/B3LYP and Cartesian coordinates (Å) are shown in FIG. 9B and Table 12. The corrections, and sum of energies are shown in Table 13. The structure was optimized using B3LYP/6-31+G(d).

TABLE 12

The Cartesian coordinates (Å) of an optimized structure of Selectfluor.

| Atom | X | Y | Z |
|---|---|---|---|
| C | 0.28758800 | 1.66408300 | 0.10897300 |
| H | 0.13440700 | 2.08355200 | 1.10584800 |
| H | -0.05377200 | 2.38902100 | -0.63358200 |
| C | -0.26365900 | -0.49618200 | 1.18588900 |
| H | -0.77312500 | -1.44517600 | 1.01644200 |
| H | -0.67442500 | -0.03705400 | 2.08787300 |
| C | 1.27264200 | -0.66959600 | 1.30602400 |
| H | 1.72085700 | -0.06235300 | 2.09516200 |
| H | 1.55961400 | -1.71398100 | 1.44789800 |
| C | 1.77080700 | 1.28687500 | -0.14045100 |
| H | 2.43986700 | 1.73032500 | 0.60049800 |
| H | 2.12306900 | 1.54125600 | -1.14220400 |
| C | -0.21692600 | -0.31485800 | -1.29130600 |
| H | -0.28887300 | 0.41254700 | -2.10320900 |
| C | 1.20842800 | -0.90745700 | -1.16443700 |

TABLE 12-continued

The Cartesian coordinates (Å) of an optimized structure of Selectfluor.

| Atom | X | Y | Z |
|---|---|---|---|
| H | 1.21770700 | −1.97726100 | −0.94608000 |
| N | −0.57827700 | 0.41223700 | 0.00002100 |
| N | 1.86800100 | −0.21120900 | −0.00081100 |
| F | 3.21964100 | −0.55452300 | −0.00259300 |
| C | −2.06184700 | 0.84713300 | −0.00139600 |
| H | −2.21171100 | 1.44980600 | 0.89602300 |

TABLE 12-continued

The Cartesian coordinates (Å) of an optimized structure of Selectfluor.

| Atom | X | Y | Z |
|---|---|---|---|
| H | −2.21126700 | 1.44626900 | −0.90117300 |
| H | 1.81629300 | −0.71485200 | −2.05145600 |
| H | −0.95251600 | −1.10378700 | −1.45761800 |
| Cl | −3.16665600 | −0.52204600 | −0.00031400 |

TABLE 13

| | |
|---|---|
| Zero-point correction = | 0.222194 (Hartree/Particle) |
| Thermal correction to Energy = | 0.231884 |
| Thermal correction to Enthalpy = | 0.232828 |
| Thermal correction to Gibbs Free Energy = | 0.187274 |
| Sum of electronic and zero-point Energies = | −943.762856 |
| Sum of electronic and thermal Energies = | −943.753167 |
| Sum of electronic and thermal Enthalpies = | −943.752222 |
| Sum of electronic and thermal Free Energies = | −943.797776 |
| CPCM (MeCN) M06L/6-311 + + G(d, p) with SDD + f (for Pd) E = | −944.3154877 |

(ix) The Optimized Structure of Selectfluor (F-TEDA) with M11L/ωB97X-D and Cartesian Coordinates (Å)

Figure 10A:
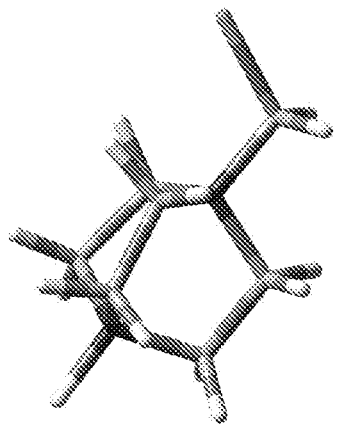
FIG. 10A shows an optimized structure of Selectfluor (F-Teda) with M11L/ωB97X-D.

The optimized structure of Selectfluor (F-Teda) with M11L/ωB97X-D and Cartesian coordinates (Å) are shown in FIG. 10A and Table 14. The corrections, and sum of energies are shown in Table 15. The structure was optimized using ωB97X-D/6−31+G(d).

TABLE 14

The Cartesian coordinates (Å) of an optimized structure of Selectfluor.

| Atom | X | Y | Z |
|---|---|---|---|
| C | 0.28497900 | 1.64793600 | 0.13492100 |
| H | 0.14577000 | 2.03987800 | 1.14496000 |
| H | −0.06162700 | 2.39568300 | −0.58165400 |
| C | −0.26727300 | −0.51496900 | 1.16094100 |
| H | −0.75231700 | −1.47114600 | 0.96151500 |
| H | −0.70027600 | −0.08919100 | 2.06855200 |
| C | 1.26328100 | −0.66005900 | 1.29906200 |
| H | 1.69274300 | −0.03677800 | 2.08568400 |
| H | 1.56182300 | −1.69807700 | 1.45814900 |
| C | 1.75672700 | 1.27691200 | −0.14403900 |
| H | 2.43825600 | 1.72662400 | 0.58086200 |
| H | 2.08606000 | 1.52953800 | −1.15369600 |
| C | −0.21122200 | −0.28914800 | −1.29188000 |
| H | −0.25900100 | 0.45609600 | −2.08912200 |
| C | 1.19643000 | −0.90349600 | −1.15397600 |
| H | 1.18517200 | −1.97152400 | −0.92843600 |
| N | −0.57494100 | 0.40915400 | 0.00077700 |
| N | 1.85822400 | −0.21111400 | −0.00086400 |
| F | 3.19176600 | −0.55099200 | −0.00342400 |
| C | −2.04220700 | 0.84341700 | −0.00014100 |
| H | −2.19457100 | 1.44652200 | 0.89668200 |
| H | −2.19401200 | 1.44380000 | −0.89879600 |
| H | 1.80819000 | −0.72859400 | −2.04129100 |
| H | −0.95354400 | −1.06468000 | −1.48908500 |
| Cl | −3.14093100 | −0.51818100 | −0.00071900 |

TABLE 15

| | |
|---|---|
| Zero-point correction = | 0.225634 (Hartree/Particle) |
| Thermal correction to Energy = | 0.234940 |
| Thermal correction to Enthalpy = | 0.235885 |
| Thermal correction to Gibbs Free Energy = | 0.191134 |
| Sum of electronic and zero-point Energies = | −943.618155 |
| Sum of electronic and thermal Energies = | −943.608849 |
| Sum of electronic and thermal Enthalpies = | −943.607905 |
| Sum of electronic and thermal Free Energies = | −943.652655 |
| CPCM (MeCN) M11L/6-311 + + G(d, p) with SDD + f (for Pd) E = | −944.2390953 |

(x) The Optimized Structure of Selectfluor Radical (TEDA) with M06L/B3LYP and Cartesian Coordinates (Å)

Figure 10B:
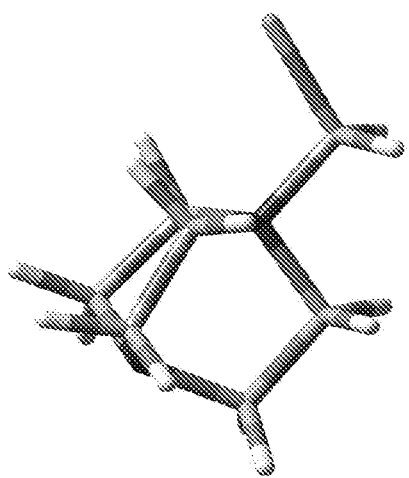
FIG. 10B shows an optimized structure of Selectfluor radical (Teda) with M11L/ωB97X-D.

The optimized structure of Selectfluor radical (TEDA) with M06L/B2LYP and Cartesian coordinates (Å) are shown in FIG. 10B and Table 16. The corrections, and sum of energies are shown in Table 17. The structure was optimized using B3LYP/6-31+G(d).

TABLE 16

The Cartesian coordinates (Å) of an optimized structure of Selectfluor radical.

| Atom | X | Y | Z |
|---|---|---|---|
| C | −0.74946300 | 1.55850900 | −0.08312200 |
| H | −0.60888900 | 2.03771500 | −1.05417500 |
| H | −0.50305000 | 2.26621500 | 0.71157200 |
| C | −0.02357100 | −0.53813500 | −1.20483300 |
| H | 0.59731500 | −1.42556600 | −1.08009500 |
| H | 0.28236200 | −0.00480100 | −2.10755100 |
| C | −1.56207600 | −0.90707500 | −1.26542100 |
| H | −2.06960100 | −0.40671100 | −2.09250100 |
| H | −1.69867700 | −1.98888100 | −1.34446100 |
| C | −2.22718100 | 1.02272900 | 0.09002700 |
| H | −2.87184600 | 1.39078900 | −0.71272000 |
| H | −2.64899000 | 1.29518400 | 1.05937900 |
| C | −0.06904200 | −0.40238500 | 1.28526900 |
| H | −0.00740700 | 0.30271400 | 2.11689500 |
| C | −1.50682700 | −1.05253600 | 1.17830200 |
| H | −1.45608200 | −2.13314700 | 1.03259100 |
| N | 0.21288300 | 0.37404400 | −0.00064800 |
| N | −2.08353300 | −0.42231500 | 0.00174700 |
| C | 1.65704100 | 0.93285800 | −0.00135500 |
| H | 1.75696700 | 1.54288700 | −0.90054900 |
| H | 1.75743500 | 1.54489300 | 0.89628200 |
| H | −2.10330600 | −0.82396200 | 2.06592300 |
| H | 0.69545200 | −1.17259300 | 1.40049900 |
| Cl | 2.87409300 | −0.33944900 | 0.00047100 |

(xi) The Optimized Structure of Selectfluor Radical (TEDA) with M11L/ωB97X-D and Cartesian Coordinates (Å)

The optimized structure of Selectfluor radical (TEDA) with M11L/ωB97X-D and Cartesian coordinates (Å) are shown in FIG. 10B and Table 18. The corrections, and sum of energies are shown in Table 19. The structure was optimized using ωB97X-D/6-31+G(d).

TABLE 18

The Cartesian coordinates (Å) of an optimized structure of Selectfluor radical.

| Atom | X | Y | Z |
|---|---|---|---|
| C | −0.74619400 | 1.54149600 | −0.12115400 |
| H | −0.62877500 | 1.97025500 | −1.11857800 |
| H | −0.48540100 | 2.29143200 | 0.62853900 |
| C | −0.01452200 | −0.56724900 | −1.17314800 |
| H | 0.56730100 | −1.47247900 | −0.99747400 |
| H | 0.33997200 | −0.08224600 | −2.08502100 |
| C | −1.55328800 | −0.87957600 | −1.26998500 |
| H | −2.03520500 | −0.33492900 | −2.08348100 |
| H | −1.72260000 | −1.95270500 | −1.38825000 |
| C | −2.20789200 | 1.01552400 | 0.11505400 |
| H | −2.88758400 | 1.39488100 | −0.65216000 |
| H | −2.58434700 | 1.27433700 | 1.10590500 |
| C | −0.07921800 | −0.36791500 | 1.29124700 |
| H | −0.06607900 | 0.36494200 | 2.10064600 |
| C | −1.48178700 | −1.06500900 | 1.15944900 |
| H | −1.39254600 | −2.13760100 | 0.98127500 |
| N | 0.21147100 | 0.37055100 | −0.00133200 |
| N | −2.06757700 | −0.42135000 | 0.00261700 |
| C | 1.63886700 | 0.92846900 | −0.00305500 |
| H | 1.73936200 | 1.53918700 | −0.90190400 |
| H | 1.74041400 | 1.54310900 | 0.89285300 |
| H | −2.08948900 | −0.88313100 | 2.04959800 |
| H | 0.70371000 | −1.11008800 | 1.45723900 |
| Cl | 2.85048300 | −0.33435100 | 0.00066900 |

TABLE 17

| | |
|---|---|
| Zero-point correction = | 0.220071 (Hartree/Particle) |
| Thermal correction to Energy = | 0.228657 |
| Thermal correction to Enthalpy = | 0.229602 |
| Thermal correction to Gibbs Free Energy = | 0.185737 |
| Sum of electronic and zero-point Energies = | −843.819959 |
| Sum of electronic and thermal Energies = | −843.811373 |
| Sum of electronic and thermal Enthalpies = | −843.810428 |
| Sum of electronic and thermal Free Energies = | −843.854293 |
| CPCM (MeCN) M06L/6-311 + + G(d, p) with SDD + f (for Pd) E = | −844.4656741 |

TABLE 19

| | |
|---|---|
| Zero-point correction = | 0.220071 (Hartree/Particle) |
| Thermal correction to Energy = | 0.228657 |
| Thermal correction to Enthalpy = | 0.229602 |
| Thermal correction to Gibbs Free Energy = | 0.185737 |
| Sum of electronic and zero-point Energies = | −843.819959 |
| Sum of electronic and thermal Energies = | −843.811373 |
| Sum of electronic and thermal Enthalpies = | −843.810428 |
| Sum of electronic and thermal Free Energies = | −843.854293 |
| CPCM (MeCN) M11L/6-311 + + G(d, p) with SDD + f (for Pd) E = | −844.4222131 |

(xii) The Optimized Structure of Selectfluor Reduced Radical (F-TEDA Reduced Radical) with M06L/B3LYP and Cartesian Coordinates (Å)

Figure 10C:
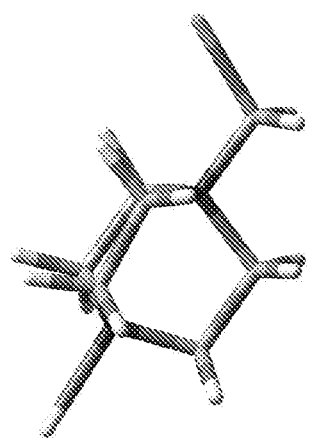
FIG. 10C shows an optimized structure of Selectfluor reduced radical (F-Teda reduced radical) with M06L/B3LYP.

The optimized structure of Selectfluor reduced radical (F-Teda reduced radical) with M06L/B3LYP and Cartesian coordinates (Å) are shown in FIG. 10C and Table 20. The corrections, and sum of energies are shown in Table 21. The structure was optimized using B3LYP/6–31+G(d).

TABLE 20

The Cartesian coordinates (Å) of an optimized structure of Selectfluor reduced radical.

| Atom | X | Y | Z |
|---|---|---|---|
| C | 0.19148500 | 1.68302300 | 0.05964700 |
| H | −0.04751200 | 2.17099100 | 1.00762400 |
| H | −0.13822600 | 2.32409100 | −0.76135100 |
| C | −0.29782800 | −0.46173200 | 1.21778300 |
| H | −0.86393200 | −1.38828800 | 1.12061500 |
| H | −0.65355900 | 0.07505500 | 2.10058700 |
| C | 1.24403800 | −0.69581500 | 1.23254100 |
| H | 1.72104100 | −0.19643900 | 2.07808600 |
| H | 1.48194400 | −1.75969600 | 1.29052300 |
| C | 1.69960200 | 1.29686100 | −0.05200300 |
| H | 2.27877800 | 1.72210200 | 0.76990400 |
| H | 2.13626800 | 1.64519000 | −0.98993600 |
| C | −0.27633100 | −0.36037400 | −1.27607800 |
| H | −0.47214300 | 0.32022100 | −2.10854400 |
| C | 1.22142600 | −0.78316100 | −1.18220000 |
| H | 1.32916400 | −1.86544500 | −1.08859000 |
| N | −0.64485000 | 0.39949600 | 0.00017600 |
| N | 1.79967300 | −0.15471200 | −0.00115500 |
| F | 3.73851900 | −0.57429800 | −0.00003800 |
| C | −2.10499100 | 0.80776600 | 0.00151700 |
| H | −2.27794600 | 1.40231900 | 0.89886900 |
| H | −2.27920800 | 1.40486100 | −0.89384900 |
| H | 1.77986100 | −0.46277300 | −2.06400400 |
| H | −0.95168100 | −1.21307100 | −1.35208800 |
| Cl | −3.22574600 | −0.56725500 | −0.00046400 |

TABLE 21

| | |
|---|---|
| Zero-point correction = | 0.219732 (Hartree/Particle) |
| Thermal correction to Energy = | 0.230460 |
| Thermal correction to Enthalpy = | 0.231404 |
| Thermal correction to Gibbs Free Energy = | 0.181921 |
| Sum of electronic and zero-point Energies = | −944.160882 |
| Sum of electronic and thermal Energies = | −944.150153 |
| Sum of electronic and thermal Enthalpies = | −944.149209 |
| Sum of electronic and thermal Free Energies = | −944.198692 |
| CPCM (MeCN) M06L/6-311 + + G(d, p) with SDD + f (for Pd) E = | −944.5287822 |

(xiii) The Optimized Structure of NFSI (N-Fluorobenzenesulfonimide) with M06L/B3LYP and Cartesian Coordinates (Å)

Figure 11A:
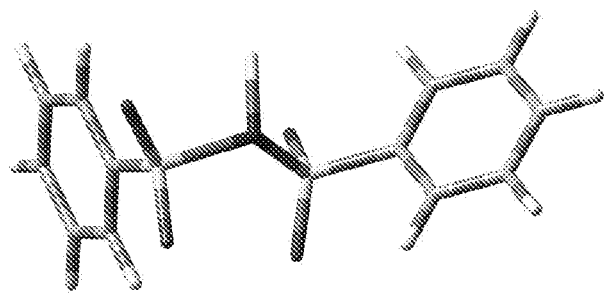
FIG. 11A shows an optimized structure of NFSI (N-fluorobenzenesulfonimide) with M06L/B3LYP.

The optimized structure of NFSI (N-fluorobenzenesulfonimide) with M06L/B3LYP and Cartesian coordinates (Å) are shown in FIG. 11A and Table 22. The corrections, and sum of energies are shown in Table 23. The structure was optimized using B3LYP/6–31+G(d).

TABLE 22

The Cartesian coordinates (Å) of an optimized structure of NFSI.

| Atom | X | Y | Z |
|---|---|---|---|
| C | 2.57155400 | −0.41783300 | 0.18882300 |
| C | 3.12734800 | −1.21632100 | −0.81321500 |
| H | 2.49916700 | −1.89298800 | −1.38255500 |
| C | 4.50014000 | −1.12461700 | −1.05126100 |
| H | 4.95322100 | −1.73867500 | −1.82429800 |
| C | 5.28629400 | −0.24814100 | −0.29725100 |
| H | 6.35405500 | −0.18144800 | −0.48804100 |
| C | 4.70947400 | 0.54217800 | 0.70316000 |
| H | 5.32515200 | 1.21892600 | 1.28867500 |
| C | 3.33974500 | 0.46406800 | 0.95454400 |
| H | 2.87448200 | 1.06542600 | 1.72879600 |
| C | −2.53829900 | 0.23201300 | −0.02654400 |
| C | −2.85401300 | −0.29854300 | 1.22758600 |
| H | −2.40330100 | 0.11288300 | 2.12416900 |
| C | −3.75743700 | −1.36021800 | 1.28935100 |
| H | −4.01944100 | −1.78518600 | 2.25403700 |
| C | −4.31948500 | −1.87456100 | 0.11675300 |
| H | −5.01993500 | −2.70356400 | 0.17326000 |
| C | −3.98949500 | −1.32897500 | −1.12821300 |
| H | −4.43224900 | −1.72936700 | −2.03576400 |
| C | −3.09238700 | −0.26377500 | −1.21055900 |
| H | −2.83341000 | 0.18184600 | −2.16500000 |
| N | 0.26854700 | 0.90957300 | −0.42892300 |
| O | −1.64398400 | 2.36219900 | −1.33461100 |
| O | −1.23402600 | 2.21439400 | 1.18963800 |
| O | 0.53815300 | −0.16657200 | 1.90143200 |
| O | 0.28989300 | −1.75046300 | −0.09311500 |

TABLE 22-continued

The Cartesian coordinates (Å) of an optimized structure of NFSI.

| Atom | X | Y | Z |
|---|---|---|---|
| S | −1.38933100 | 1.59657300 | −0.12047000 |
| S | 0.81887300 | −0.53211400 | 0.51526900 |
| F | 0.27209400 | 0.46063200 | −1.77926400 |

TABLE 23

| | |
|---|---|
| Zero-point correction = | 0.208407 (Hartree/Particle) |
| Thermal correction to Energy = | 0.226484 |
| Thermal correction to Enthalpy = | 0.227428 |
| Thermal correction to Gibbs Free Energy = | 0.159637 |
| Sum of electronic and zero-point Energies = | −1714.765356 |
| Sum of electronic and thermal Energies = | −1714.747279 |
| Sum of electronic and thermal Enthalpies = | −1714.746334 |
| Sum of electronic and thermal Free Energies = | −1714.814125 |
| CPCM (MeCN) M06L/6-311 + + G(d, p) with SDD + f (for Pd) E = | −1715.121608 |

(xiv) The Optimized Structure of NFSI (N-Fluorobenzenesulfonimide) with M11L/ωB97X-D and Cartesian Coordinates (Å)

Figure 11B:
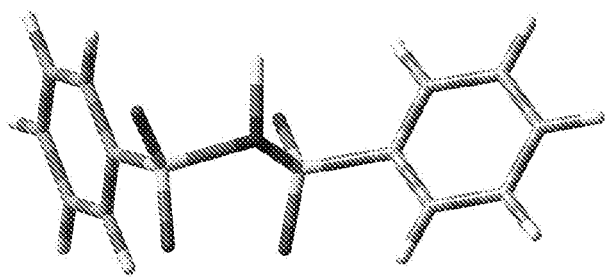
FIG. 11B shows an optimized structure of NFSI (N-fluorobenzenesulfonimide) with M11L/ωB97X-D.

The optimized structure of NFSI (N-fluorobenzenesulfonimide) with M11L/ωB97X-D and Cartesian coordinates (Å) are shown in FIG. 11B and Table 24. The corrections, and sum of energies are shown in Table 25. The structure was optimized using ωB97X-D/6−31+G(d).

TABLE 24

The Cartesian coordinates (Å) of an optimized structure of NFSI.

| Atom | X | Y | Z |
|---|---|---|---|
| C | 2.49565000 | −0.42062800 | 0.19065700 |
| C | 3.04084100 | −1.20807000 | −0.81925600 |
| H | 2.40444400 | −1.86365700 | −1.40392700 |
| C | 4.41122800 | −1.13215600 | −1.05105200 |
| H | 4.85828400 | −1.73825300 | −1.83267300 |
| C | 5.20410900 | −0.28300300 | −0.28110500 |
| H | 6.27274800 | −0.22822600 | −0.46663800 |
| C | 4.63757200 | 0.49788100 | 0.72679000 |
| H | 5.26100600 | 1.15469700 | 1.32504800 |
| C | 3.27036600 | 0.43565200 | 0.97043500 |
| H | 2.80905800 | 1.03230600 | 1.75076400 |
| C | −2.47975900 | 0.24293800 | −0.02240600 |
| C | −2.76862200 | −0.29670300 | 1.22907700 |
| H | −2.33560800 | 0.13716700 | 2.12382200 |
| C | −3.61223900 | −1.40048800 | 1.29264900 |
| H | −3.85081700 | −1.83809500 | 2.25674800 |
| C | −4.14144300 | −1.94494700 | 0.12367000 |
| H | −4.79623400 | −2.80958000 | 0.18118500 |
| C | −3.84004600 | −1.38903500 | −1.11917400 |
| H | −4.25859100 | −1.81635000 | −2.02487500 |
| C | −3.00121900 | −0.28335700 | −1.20236700 |
| H | −2.75908200 | 0.16951400 | −2.15783400 |
| N | 0.24742900 | 0.92201900 | −0.42239000 |
| O | −1.62507100 | 2.36562800 | −1.33117100 |
| O | −1.21670400 | 2.23644800 | 1.17172500 |
| O | 0.46971100 | −0.14726900 | 1.87491600 |
| O | 0.20948100 | −1.69458200 | −0.11645500 |
| S | −1.36657300 | 1.61608100 | −0.12353400 |
| S | 0.75409100 | −0.50327600 | 0.50034500 |
| F | 0.27383500 | 0.50568500 | −1.76038700 |

TABLE 25

| | |
|---|---|
| Zero-point correction= | 0.212670 (Hartree/Particle) |
| Thermal correction to Energy= | 0.230197 |
| Thermal correction to Enthalpy= | 0.231141 |
| Thermal correction to Gibbs Free Energy= | 0.165085 |
| Sum of electronic and zero-point Energies= | −1714.430838 |
| Sum of electronic and thermal Energies= | −1714.413312 |
| Sum of electronic and thermal Enthalpies= | −1714.412368 |

TABLE 25-continued

| | |
|---|---|
| Sum of electronic and thermal Free Energies= | −1714.478424 |
| CPCM (MeCN) M11L/6-311++G(d, p) with SDD+f (for Pd) E= | −1714.981376 |

(xv) The Optimized Structure of NFSI Radical (N-Fluorobenzenesulfonimide) with M06L/B3L YP and Cartesian Coordinates (Å)

Figure 11C:
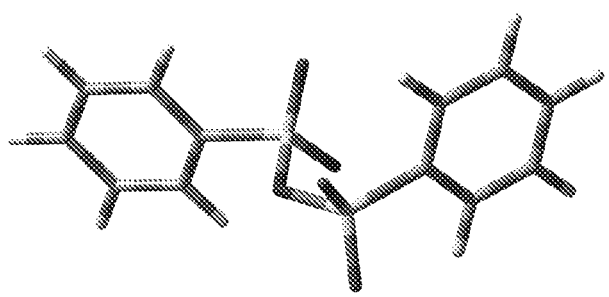
FIG. 11C shows an optimized structure of NFSI (N-fluorobenzenesulfonimide) radical with M06L/B3LYP.

The optimized structure of NFSI (N-fluorobenzenesulfonimide) radical with M06L/B3LYP and Cartesian coordinates (Å) are shown in FIG. 11C and Table 26. The corrections, and sum of energies are shown in Table 27. The structure was optimized using B3LYP/6−31+G(d).

TABLE 26

The Cartesian coordinates (Å) of an optimized structure of NFSI radical.

| Atom | X | Y | Z |
|---|---|---|---|
| C | −2.55213300 | −0.39343500 | 0.00001900 |
| C | −3.22505100 | −0.33554200 | 1.22285600 |
| H | −2.67181300 | −0.39345700 | 2.15443100 |
| C | −4.61545400 | −0.21402700 | 1.21392900 |
| H | −5.15670000 | −0.17035900 | 2.15471400 |
| C | −5.30717500 | −0.15124900 | 0.00002000 |
| H | −6.38971700 | −0.05658700 | 0.00002100 |
| C | −4.61546000 | −0.21408100 | −1.21388900 |
| H | −5.15671100 | −0.17045400 | −2.15467400 |
| C | −3.22505700 | −0.33559700 | −1.22281800 |
| H | −2.67182400 | −0.39355300 | −2.15439300 |
| C | 2.45872300 | 0.25981200 | −0.00001300 |
| C | 2.90453800 | −0.24735400 | −1.22360200 |
| H | 2.54265800 | 0.17412100 | −2.15488400 |
| C | 3.82378400 | −1.29667400 | −1.21410000 |
| H | 4.18275600 | −1.70391600 | −2.15491300 |
| C | 4.28003000 | −1.81953200 | 0.00005300 |
| H | 4.99585500 | −2.63727600 | 0.00007900 |
| C | 3.82380200 | −1.29658200 | 1.21417200 |
| H | 4.18278700 | −1.70375300 | 2.15501200 |
| C | 2.90455600 | −0.24726100 | 1.22360900 |
| H | 2.54269000 | 0.17428500 | 2.15486500 |
| N | −0.33063500 | 1.10800500 | −0.00002700 |
| O | 1.41976900 | 2.33894500 | 1.28036300 |
| O | 1.41975200 | 2.33884800 | −1.28053200 |
| O | −0.33588800 | −1.12259800 | −1.27803400 |
| O | −0.33587900 | −1.12253000 | 1.27809700 |

TABLE 26-continued

The Cartesian coordinates (Å) of an optimized structure of NFSI radical.

| Atom | X | Y | Z |
|------|---|---|---|
| S | 1.31200000 | 1.63423700 | −0.00005700 |
| S | −0.77188700 | −0.54594200 | 0.00001700 |

TABLE 27

| | |
|---|---|
| Zero-point correction= | 0.204537 |
| | (Hartree/Particle) |
| Thermal correction to Energy= | 0.221664 |
| Thermal correction to Enthalpy= | 0.222608 |
| Thermal correction to Gibbs Free Energy= | 0.155783 |
| Sum of electronic and zero-point Energies= | −1614.943259 |
| Sum of electronic and thermal Energies= | −1614.926131 |
| Sum of electronic and thermal Enthalpies= | −1614.925187 |
| Sum of electronic and thermal Free Energies= | −1614.992012 |
| CPCM (MeCN) M06L/6-311++G(d, p) with SDD+f (for Pd) E= | −1615.279275 |

(xvi) The Optimized Structure of NFSI Radical (N-Fluorobenzenesulfonimide) with M11L/ωB97X-D and Cartesian Coordinates (Å)

Figure 11D:
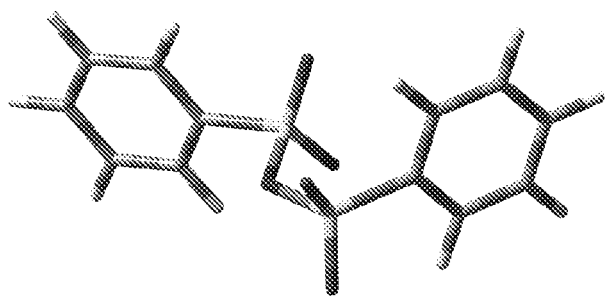
FIG. 11D shows an optimized structure of NFSI radical (N-fluorobenzenesulfonimide) with M11L/ωB97X-D.

The optimized structure of NFSI (N-fluorobenzenesulfonimide) radical with M11L/ωB97X-D and Cartesian coordinates (Å) are shown in FIG. 11D and Table 28. The corrections, and sum of energies are shown in Table 29. The structure was optimized using ωB97X-D/6–31+G(d).

TABLE 28

The Cartesian coordinates (Å) of an optimized structure of NFSI radical.

| Atom | X | Y | Z |
|------|---|---|---|
| C | −2.49886500 | −0.39867900 | 0.00001000 |
| C | −3.16892200 | −0.34289800 | 1.21923500 |
| H | −2.61522300 | −0.39661400 | 2.15080400 |
| C | −4.55535500 | −0.22683700 | 1.21074200 |
| H | −5.09635900 | −0.18378600 | 2.15070500 |
| C | −5.24422600 | −0.16666100 | 0.00004400 |
| H | −6.32623800 | −0.07363600 | 0.00005800 |
| C | −4.55539500 | −0.22696100 | −1.21067000 |
| H | −5.09643200 | −0.18400800 | −2.15061900 |
| C | −3.16896200 | −0.34302100 | −1.21919800 |
| H | −2.61529500 | −0.39683200 | −2.15078000 |
| C | 2.41615500 | 0.26882100 | −0.00000500 |
| C | 2.83974300 | −0.25354700 | −1.21993800 |
| H | 2.48764700 | 0.17745900 | −2.15058500 |
| C | 3.71612400 | −1.33280900 | −1.21104000 |
| H | 4.05878600 | −1.75485300 | −2.15038900 |
| C | 4.15112700 | −1.86935600 | 0.00006100 |
| H | 4.83638700 | −2.71201300 | 0.00008700 |
| C | 3.71609100 | −1.33276200 | 1.21112800 |
| H | 4.05872700 | −1.75476800 | 2.15050400 |
| C | 2.83971000 | −0.25349800 | 1.21996000 |
| H | 2.48759000 | 0.17754500 | 2.15058000 |
| N | −0.31765400 | 1.11810300 | −0.00004600 |
| O | 1.41215300 | 2.34443300 | 1.27010400 |
| O | 1.41217200 | 2.34437100 | −1.27023200 |
| O | −0.28940000 | −1.08477200 | −1.26788000 |
| O | −0.28936700 | −1.08471600 | 1.26787300 |
| S | 1.30416800 | 1.65116800 | −0.00000480 |
| S | −0.73190800 | −0.52682400 | −0.00001000 |

TABLE 29

| | |
|---|---|
| Zero-point correction= | 0.208315 |
| | (Hartree/Particle) |
| Thermal correction to Energy= | 0.225021 |
| Thermal correction to Enthalpy= | 0.225965 |
| Thermal correction to Gibbs Free Energy= | 0.160252 |
| Sum of electronic and zero-point Energies= | −1614.632297 |
| Sum of electronic and thermal Energies= | −1614.615591 |
| Sum of electronic and thermal Enthalpies= | −1614.614647 |
| Sum of electronic and thermal Free Energies= | −1614.680360 |
| CPCM (MeCN) M11L/6-311++G(d, p) with SDD+f (for Pd) E= | −1615.164493 |

(xvii) The Optimized Structure of NFSI (N-Fluorobenzenesulfonimide Reduced Radical with M06L/B3L YP and Cartesian Coordinates (Å)

Figure 12A:
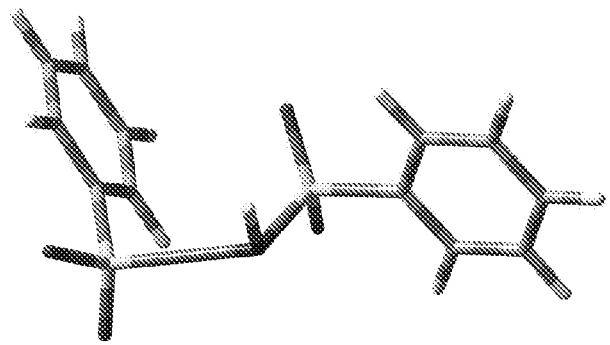
FIG. 12A shows an optimized structure of NFSI (N-fluorobenzenesulfonimide) reduced radical with M06L/B3LYP.

The optimized structure of NFSI (N-fluorobenzenesulfonimide) reduced radical with M06L/B3LYP and Cartesian coordinates (Å) are shown in FIG. 12A and Table 30. The corrections, and sum of energies are shown in Table 31. The structure was optimized using B3LYP/6–31+G(d).

TABLE 30

The Cartesian coordinates (Å) of an optimized structure of NFSI reduced radical.

| Atom | X | Y | Z |
|------|---|---|---|
| C | 2.87850700 | −0.32582600 | 0.06415800 |
| C | 3.49508400 | −0.53399300 | −1.17171400 |
| H | 2.88224500 | −0.74315600 | −2.04240800 |
| C | 4.88917800 | −0.48062200 | −1.26028100 |
| H | 5.37475800 | −0.64200600 | −2.22038200 |
| C | 5.65765300 | −0.22285800 | −0.12063100 |
| H | 6.74263000 | −0.18417200 | −0.19234300 |
| C | 5.02937400 | −0.01614800 | 1.11306900 |
| H | 5.62472500 | 0.18146000 | 2.00197300 |
| C | 3.63681800 | −0.06191500 | 1.20817200 |
| H | 3.12986700 | 0.09552200 | 2.15523200 |
| C | −2.90187300 | 0.00737400 | 0.05055300 |
| C | −2.78972500 | −0.85679700 | 1.14040900 |
| H | −2.29882800 | −0.52240200 | 2.04838700 |
| C | −3.30614400 | −2.15026000 | 1.03329600 |
| H | −3.21950600 | −2.83448900 | 1.87419300 |
| C | −3.91559800 | −2.56964000 | −0.15389300 |
| H | −4.30862300 | −3.58099000 | −0.23481100 |
| C | −4.00662300 | −1.69562900 | −1.24182200 |
| H | −4.47323900 | −2.02340300 | −2.16843500 |
| C | −3.48974900 | −0.40047700 | −1.14680200 |
| H | −3.54392100 | 0.29470200 | −1.97864900 |
| N | 0.60061100 | 1.25539800 | 0.02084700 |
| O | −2.78059000 | 2.45472600 | −0.97160900 |
| O | −2.47682400 | 2.14534600 | 1.57130700 |
| O | 0.73494100 | −0.66196100 | 1.58988100 |
| O | 0.61485800 | −1.24899500 | −0.89506900 |
| S | −2.17646000 | 1.68754500 | 0.17292900 |
| S | 1.06648800 | −0.34477300 | 0.18291900 |
| F | 0.87163000 | 1.55717800 | −1.39171300 |

TABLE 31

| | |
|---|---|
| Zero-point correction= | 0.203584 |
| | (Hartree/Particle) |
| Thermal correction to Energy= | 0.223259 |
| Thermal correction to Enthalpy= | 0.224203 |
| Thermal correction to Gibbs Free Energy= | 0.148230 |
| Sum of electronic and zero-point Energies= | −1714.850713 |
| Sum of electronic and thermal Energies= | −1714.831038 |
| Sum of electronic and thermal Enthalpies= | −1714.830094 |
| Sum of electronic and thermal Free Energies= | −1714.906067 |
| CPCM (MeCN) M06L/6-311++G(d, p) with SDD+f (for Pd) E= | −1715.259329 |

(xviii) The Optimized Structure of MeCN Reduced Radical with M06L/B3LYP and Cartesian Coordinates (Å)

Figure 12B:
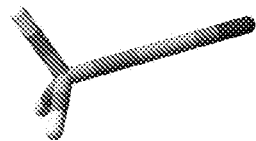
FIG. 12B shows an optimized structure of MeCN reduced radical with M06L/B3LYP.

The optimized structure of MeCN reduced radical with M06L/B3LYP and Cartesian coordinates (Å) are shown in FIG. 12B and Table 32. The corrections, and sum of energies are shown in Table 33. The structure was optimized using B3LYP/6-31+G(d).

TABLE 32

The Cartesian coordinates (Å) of an optimized structure of MeCN with M06L/B3LYP.

| Atom | X | Y | Z |
|---|---|---|---|
| C | 0.00000000 | 0.00000000 | −1.18195100 |
| H | 0.00000000 | 1.02729700 | −1.56051500 |
| H | 0.88966500 | −0.51364900 | −1.56051500 |
| H | −0.88966500 | −0.51364900 | −1.56051500 |
| C | 0.00000000 | 0.00000000 | 0.28041900 |
| N | 0.00000000 | 0.00000000 | 1.44153400 |

TABLE 33

| | |
|---|---|
| Zero-point correction= | 0.045484 |
| | (Hartree/Particle) |
| Thermal correction to Energy= | 0.049096 |
| Thermal correction to Enthalpy= | 0.050040 |
| Thermal correction to Gibbs Free Energy= | 0.022491 |
| Sum of electronic and zero-point Energies= | −132.716212 |
| Sum of electronic and thermal Energies= | −132.712601 |
| Sum of electronic and thermal Enthalpies= | −132.711656 |
| Sum of electronic and thermal Free Energies= | −132.739206 |
| CPCM (MeCN) M06L/6-311++G(d, p) with SDD+f (for Pd) E= | −132.7820383 |

VII. Evaluation of Other [Pd] Catalysts in Fluorination

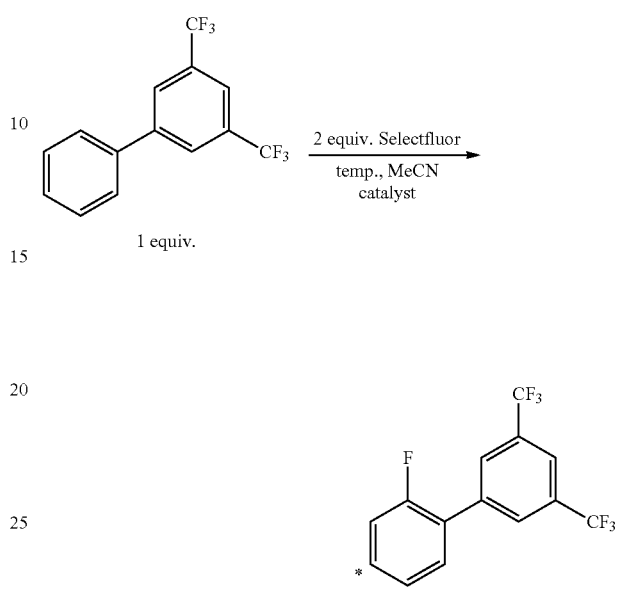

TABLE 34

| Pd catalyst (5 mol %) | ligand (mol %) | temp.[a] | yield[b] |
|---|---|---|---|
| Pd(OAc)$_2$ | none | 80° C. | 3% |
| Pd(MeCN)$_4$(BF$_4$)$_2$ | none | 80° C. | 4% |
| Pd(terpy)(MeCN)(BF$_4$)$_2$ | terpy (10%) | 80° C. | 18% |
| Pd(terpy)(MeCN)(BF$_4$)$_2$ | 4,7-(OMe)$_2$ phen (5%) | 80° C. | 5% |
| Pd(terpy)(MeCN)(BF$_4$)$_2$ | phen (5%) | 50° C. | 34% |
| Pd(terpy)(MeCN)(BF | 2-Cl phen (5%) | | 75% |

[a]Temperature listed is that which provided highest yield among reactions conducted at 23, 50 and 80° C. after 24 h.
bYields determined by $^{19}$F-NMR of reaction with internal standard.

The proposed mechanism for the Pd-catalyzed fluorination reaction suggests the possibility that the combination of a tridentate terpyridine ligand and a bidentate phenanthroline ligand in a catalyst would be competent in the fluorination reaction. Therefore, an evaluation of other potential catalysts including these ligand combinations was performed, summarized in Table 34 above. The results indicate that electron deficient phenanthroline ligands combined with terpyridine are more effective.

Results

As shown in Table 35, a wide variety of arenes can be fluorinated, including both electron-rich, electron-neutral and electron-poor arenes. A wide range of compounds of Formula (I) have been prepared using the inventive methods, including compounds where one or more $R^4$ is a halogen, alkyl, carbocyclyl, aryl, or heteroaryl.

TABLE 35
Substrate scope for the Pd-catalyzed fluorination of arenes.[a]
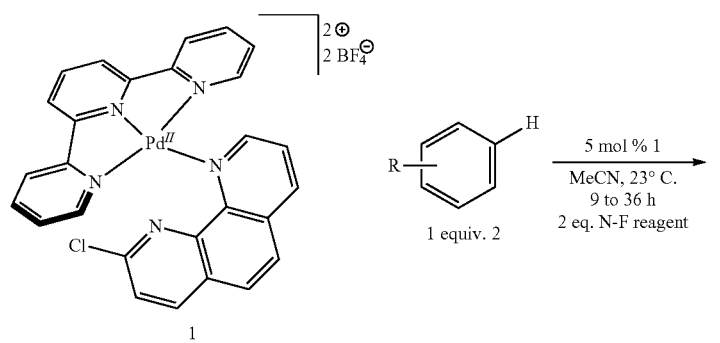
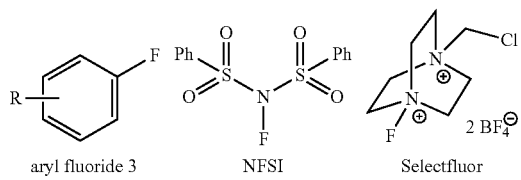
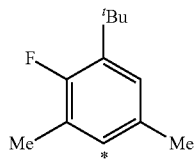
3a, 65%, 83:17[b]
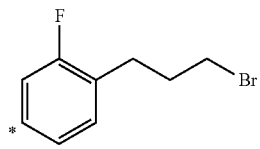
3f, 52%, 46:54[b,d]
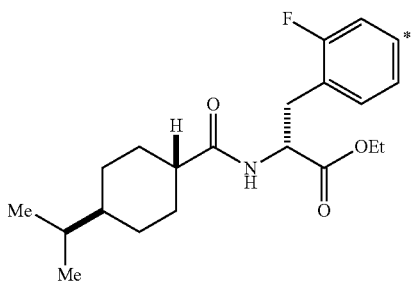
3k, F-ethyl nateglinide,
57%, 60:40[b]
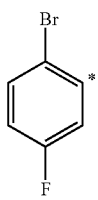
3b, 58%, 52:48[c,d]

TABLE 35-continued
Substrate scope for the Pd-catalyzed fluorination of arenes.[a]
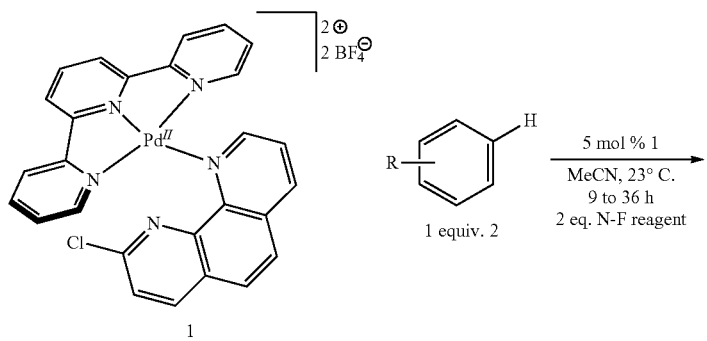
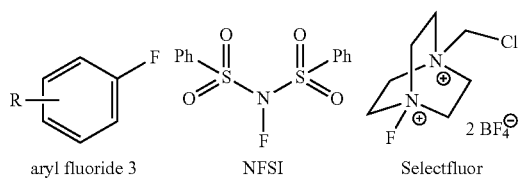
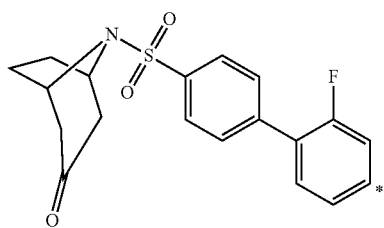
3g, 73%, 74:26[b]
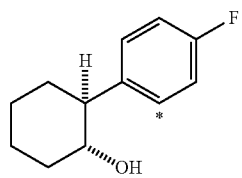
3l, 42%, 59:41[c]
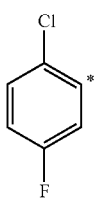
3c, 58%, 62:38[c,d]
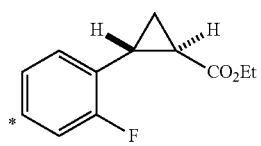
3h, 53%, 70:30[b]

TABLE 35-continued
Substrate scope for the Pd-catalyzed fluorination of arenes.[a]
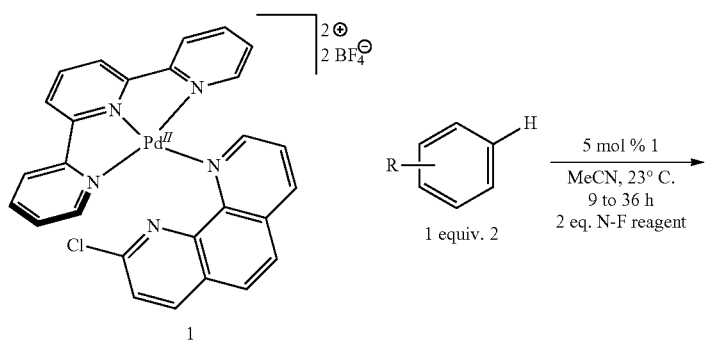
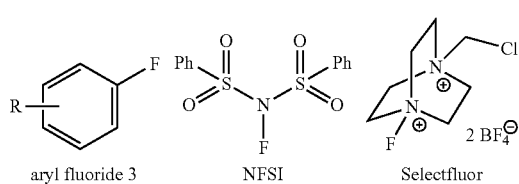
3m, 57%, 53:47[c,e]
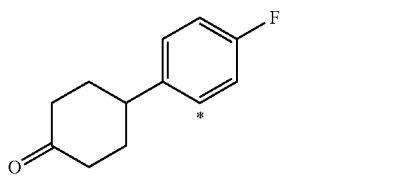
3d, 73%, 73:27[b]
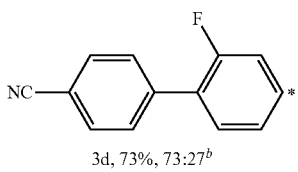 [SMILES: N#Cc1ccc(-c2ccccc2F)cc1]
3i, 58%, 52:48[c]
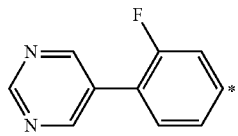
3n, 68%, 69:31[c]
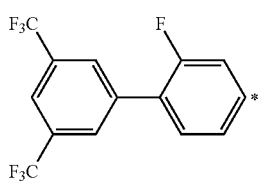
3e, 75%, 72:28[c]

TABLE 35-continued

Substrate scope for the Pd-catalyzed fluorination of arenes.[a]

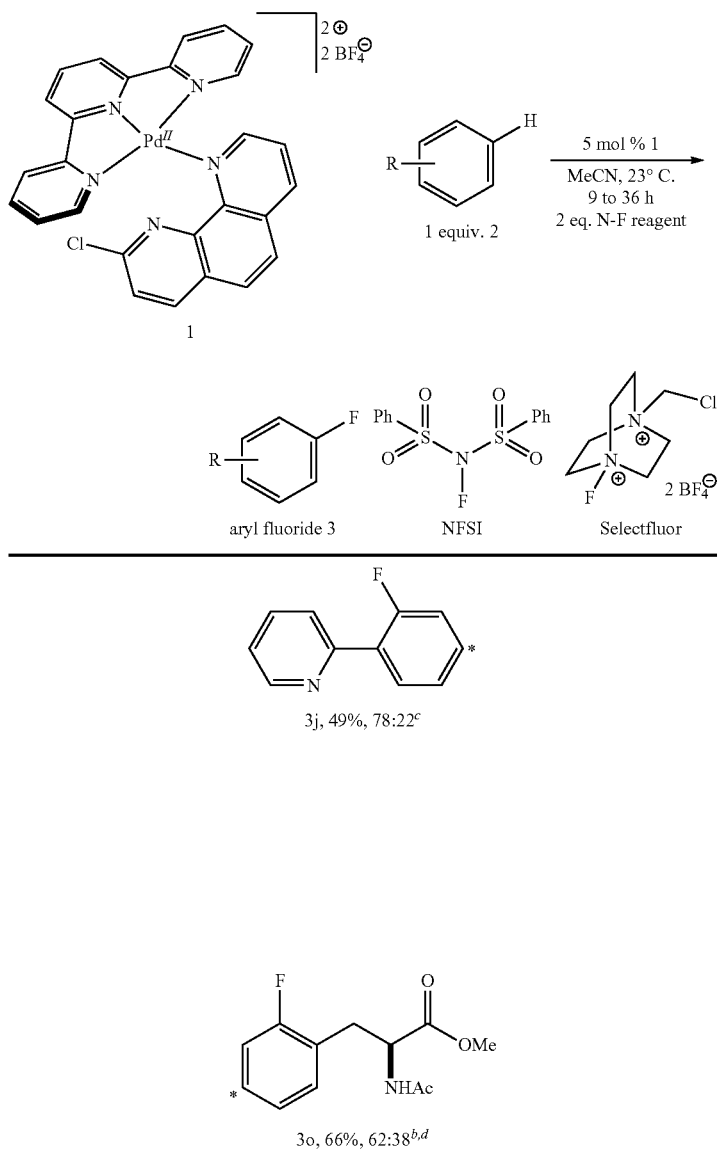

[a]Yields and the ratio of the constitutional isomers reported based on $^{19}$F-NMR of isolated mixtures with internal standard.
*denotes site of fluorination of other constitutional isomer. Catalyst 1 was preformed from 5 mol % Pd(MeCN)(terpy)(BF$_4$) and 5 mol % 2-Cl-1,10-phenanthroline in MeCN. Arene (1 mmol), catalyst 1 (5 mol %), Selectfluor or NFSI (2 equiv.), MeCN (0.1 M).
[b]Reaction performed with NFBS.
[c]Reaction performed with Selectfluor.
[d]Reaction performed at 50° C.
[e]Reaction performed at 0° C.
[f]Reaction performed with DCE and MeCN (1:1, 0.1 M).

Discussion of Potential Fluorination Mechanism

DFT calculations for catalyst 1 indicate the HOMO lies largely on the Pd with some N contribution (see DFT Calculations section). Although not bound to this theory, the Pd—N interaction may be important for facile oxidation of the Pd(II) and enables formation of the high-valent palladium species. For an example of decreased oxidation potential of a Pd complex induced by increasing the coordination capacity of linked apical ligands, see Tang, F.; Qu, F.; Khusnutdinova, J. R.; Rath, N. P.; Mirica, L. M. Dalton Trans. 2012, 41, 14046.

A previously developed catalyst capable of a single electron reduction of Selecfluor, in situ generated Pd(terpy)$_2$ (BF$_4$)$_2$, is significantly less effective than the optimized catalyst 1. See Mazzotti, A. R.; Campbell, M. G.; Tang, P.; Murphy, J. M.; Ritter, T. J. Am. Chem. Soc. 2013, 135, 14012. The lower reactivity of a known SET catalyst relative to the optimized catalyst 1 precludes initial single-electron reduction of the N—F reagents as a possible mechanism. Additionally, DFT calculations indicate the reduction of NFSI with catalyst 1 is a highly endothermic (56 kcal mol$^{-1}$, see DFT Calculations section), which effectively eliminates single electron reduction of NFSI as a viable pathway. Conversely, DFT calculations indicate oxidation of compound 1 by N—F reagents to a Pd(III)-F species are also endergonic, but significantly less so than a SET pathway (11 kcal mol$^{-1}$).

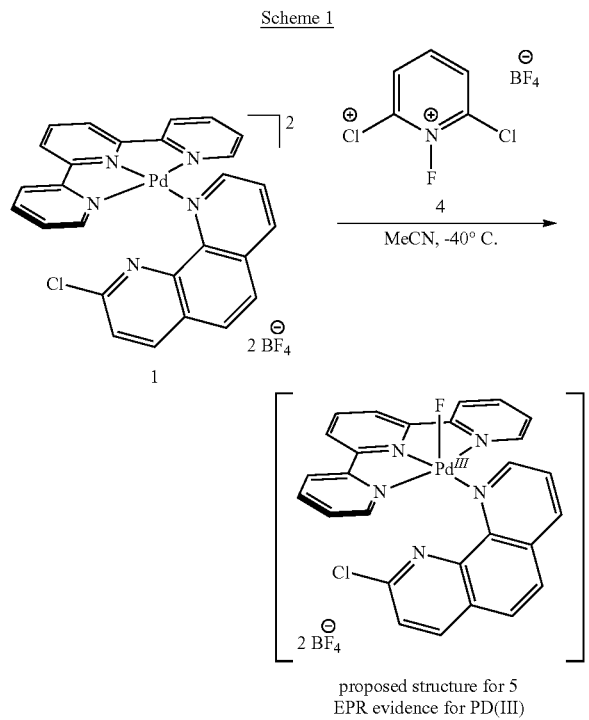

Scheme 1 proposed structure for 5
EPR evidence for PD(III)

As depicted in Scheme 1, after a cold solution of catalyst 1 was treated with N-fluoropyridinium 4 and then frozen, an EPR signal was observed with hyperfine splitting by two nitrogens.

To solution of catalyst 1 at −40° C., prepared from a mixture of palladium complex S1 (13.9 mg, 25 µmol, 1.0 equiv.) and 2-chloro-phenanthroline (5.4 mg, 25 µmol, 1.0 equiv.) in CD$_3$CN (2 mL), a solution of 2,6-dichloro-1-fluoropyridinium tetrafluoroborate (4) (6.4 mg, 25 µmol, 1.0 equiv. in 0.25 mL CD$_3$CN) at −40° C. was added in a 4 mL vial in the cold well of glovebox. The solution was stirred for 5 min and a dark purple color formed. The solution was carefully transferred to a cooled J-Young NMR tube then frozen at −60° C., sealed and removed from the glovebox. Vacuum was applied to the frozen solid and then the sample was transferred to the NMR instrument set to −40° C. After allowing 5 min in the NMR for the sample to thaw and the temperature to stabilize, the $^{19}$F NMR spectra were measured. After −40° C., the sample was warmed at 10° C. intervals up to −10° C., allowing the sample to equilibrate for 5 min before the $^{19}$F NMR were measured. The tetrafluoroborate was taken as an internal standard for $^{19}$F NMR (δ −150.1 ppm, 12 F) and used to determine oxidant consumption (δ 30.1 ppm, 1 F). The amount of oxidant remaining was determined to be: 68% at −40° C.; 63% at −30° C.; 48% at −20° C.; and 42% at −10° C. The region between δ −150 and −400 ppm contained no signals that could be attributed to formation of a Pd(IV)-F.

The hyperfine splitting is consistent with coupling from either two trans terpyridine nitrogens in 5, or from an MeCN, in place of a fluoride in 5, and the trans phenanthroline nitrogen. The observed EPR signal of a Pd(III) species in presence of an N—F oxidant may indicate the involvement of an open-shell metal species in catalysis via catalyst 1.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

All patents, patent applications, and literature references cited herein are incorporated herein by reference.

The foregoing has been a description of certain non-limiting embodiments of the invention. Those of ordinary skill in the art will appreciate that various changes and modifications to this description may be made without departing from the spirit or scope of the present invention, as defined in the following claims.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A palladium complex that comprises a moiety, wherein the moiety is represented by:

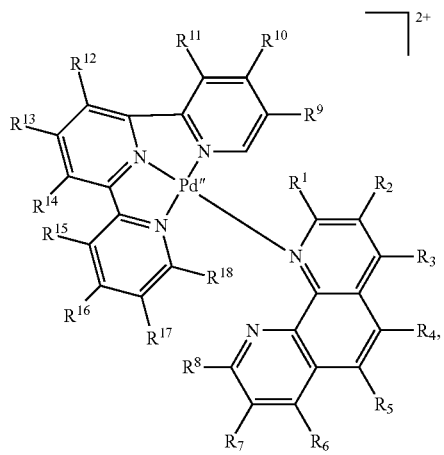

wherein:
R$^1$, R$^2$, R$^3$, R$^4$, R$^5$, R$^6$, R$^7$, and R$^8$ are independently selected from the group consisting of hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N(R)$_2$, —SR, —CN, —SCN, —C(=NR)R, —C(=NR)OR, —C(=NR)N(R)$_2$, —C(=O)R, —C(=O)OR, —C(=O)N(R)$_2$, —NO$_2$, —NRC(=O)R, —NRC(=O)OR, —NRC(=O)N(R)$_2$, —OC(=O)R, —OC(=O)OR, —OC(=O)N(R)$_2$, —SO$_3$H, and —NR$_3$$^+$Y', wherein Y' is an anionic counterion;

R$^9$, R$^{10}$, R$^{11}$, R$^{12}$, R$^{13}$, R$^{14}$, R$^{15}$, R$^{16}$, R$^{17}$, and R$^{18}$ are independently selected from the group consisting of hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N(R)$_2$, —SR, —CN, —SCN, —C(=NR)R, —C(=NR)OR, —C(=NR)N(R)$_2$, —C(=O)R, —C(=O)OR, —C(=O)N(R)$_2$, —NO$_2$, —NRC(=O)R, —NRC(=O)OR, —NRC(=O)N(R)$_2$, —OC(=O)R, —OC(=O)OR, —OC(=O)N(R)$_2$, —SO$_3$H, and —NR$_3$$^+$Y', wherein Y' is an anionic counterion; and each instance of R is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R attached to the same nitrogen atom are joined to form a substituted or unsubstituted heterocyclic or substituted or unsubstituted heteroaryl ring.

2. The palladium complex of claim 1, wherein the palladium complex is of Formula (C):

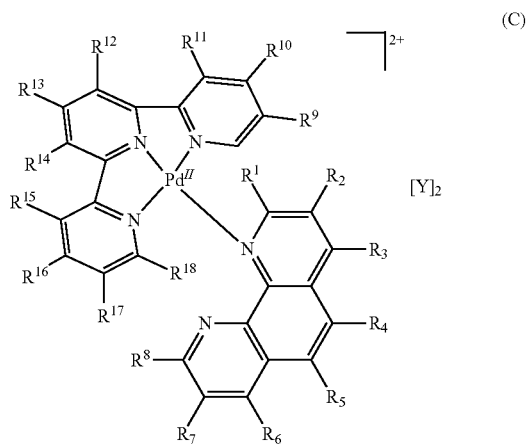

wherein Y is an anionic counterion, alkenyl, or alkynyl.

3. The palladium complex of claim 2, wherein Y is an anionic counterion.

4. The palladium complex of claim 2, wherein Y is BF$_4$$^-$ or OTf$^-$.

5. The palladium complex of claim 1, wherein each of R$^1$, R$^2$, R$^3$, R$^4$, R$^5$, R$^6$, and R$^7$ is hydrogen.

6. The palladium complex of claim 1, wherein R$^8$ is halogen, —COR, —COOR —CN, —SO$_3$H, —NO$_2$, haloalkyl, or —NR$_3$$^+$Y'.

7. The palladium complex of claim 1, wherein R$^8$ is halogen.

8. The palladium complex of claim 1, wherein R$^8$ is chloro.

9. The palladium complex of claim 1, wherein each of R$^1$, R$^2$, R$^3$, R$^4$, R$^5$, R$^6$, and R$^7$ is hydrogen, and R$^8$ is halogen.

10. The palladium complex of claim 1, wherein each of R$^9$, R$^{10}$, R$^{11}$, R$^{12}$, R$^{13}$, R$^{14}$, R$^{15}$, R$^{16}$, R$^{17}$, and R$^{18}$ is hydrogen.

11. The palladium complex of claim 1, wherein each of R$^9$, R$^{10}$, R$^{11}$, R$^{12}$, R$^{13}$, R$^{14}$, R$^{15}$, R$^{16}$, R$^{17}$, and R$^{18}$ is hydrogen; each of R$^1$, R$^2$, R$^3$, R$^4$, R$^5$, R$^6$, and R$^7$ is hydrogen; and R$^8$ is hydrogen, halogen, —COR, —COOR, —CN, —SO$_3$H, —NO$_2$, haloalkyl, or —NR$_3$$^+$Y'.

12. The palladium complex of claim 1, wherein the palladium complex is of Formula (C-1):

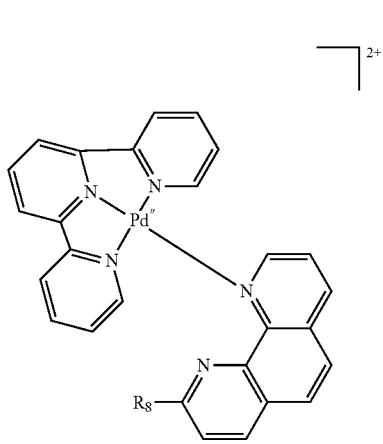

(C-1)

wherein $R^8$ is halogen, and Y is $BF_4^-$ or $OTf^-$.

13. The palladium complex of claim 1, wherein the palladium complex is of the formula:

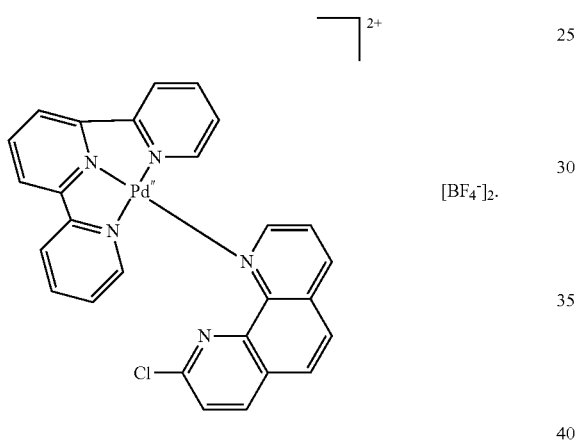

14. A composition comprising a palladium complex of claim 1.

15. A kit comprising a palladium complex of claim 1.

16. The kit of claim 15 further comprising a compound of Formula (D), (E), or (F):

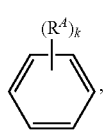

(D)

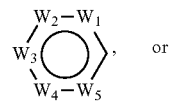

(E)

(F)

wherein:
each of $W_1$, $W_2$, $W_3$, $W_4$, and $W_5$ is independently CH, $CR^A$, or N, provided that at least one of $W_1$, $W_2$, $W_3$, $W_4$, and $W_5$ is N;
each of $W_6$, $W_7$, $W_8$, and $W_9$ is CH, $CR^A$, N, NH, $NR^A$, O, or S, provided that at least one of $W_6$, $W_7$, $W_8$, and $W_9$ is N, NH, $NR^A$, O, or S;
each instance of $R^A$ is independently halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A1}$, $-N(R^{A1})_2$, $-SR^{A1}$, $-CN$, $-SCN$, $-C(=NR^{A1})R^{A1}$, $-C(=NR^{A1})OR^{A1}$, $-C(=NR^{A1})N(R^{A1})_2$, $-C(=O)R^{A1}$, $-C(=O)OR^{A1}$, $-C(=O)N(R^{A1})_2$, $-NO_2$, $-NR^{A1}C(=O)R^{A1}$, $-NR^{A1}C(=O)OR^{A1}$, $-NR^{A1}C(=O)N(R^{A1})_2$, $-OC(=O)R^{A1}$, $-OC(=O)OR^{A1}$, or $-OC(=O)N(R^{A1})_2$, or two vicinal $R^A$ groups are joined to form a substituted or unsubstituted carbocyclic, substituted or unsubstituted heterocyclic, substituted or unsubstituted aryl, or substituted or unsubstituted heteroaryl ring;
each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1}$ attached to the same nitrogen atom are joined to form a substituted or unsubstituted heterocyclic or substituted or unsubstituted heteroaryl ring; and
k is 0, 1, 2, 3, 4, or 5.

17. The kit of claim 15 further comprising a fluorinating agent.

* * * * *